(12) United States Patent
Milton et al.

(10) Patent No.: US 7,132,419 B2
(45) Date of Patent: Nov. 7, 2006

(54) PHARMACEUTICAL COMPOUNDS

(75) Inventors: John Milton, Slough (GB); Nigel Vicker, Slough (GB); Adrian Folkes, Slough (GB); Shouming Wang, Slough (GB); William Alexander Denny, Auckland (NZ)

(73) Assignee: Xenova Limited, Slough (GB)

( * ) Notice: Subject to any disclaimer, the term of this patent is extended or adjusted under 35 U.S.C. 154(b) by 0 days.

(21) Appl. No.: 11/024,759

(22) Filed: Dec. 30, 2004

(65) Prior Publication Data
US 2005/0143383 A1 Jun. 30, 2005

Related U.S. Application Data

(63) Continuation of application No. 10/148,601, filed as application No. PCT/GB00/04609 on Dec. 1, 2000, now abandoned.

(51) Int. Cl.
C07D 241/46 (2006.01)
A61K 31/498 (2006.01)

(52) U.S. Cl. .................. 514/232.8; 544/116; 544/295; 544/343; 514/250

(58) Field of Classification Search ................ 514/250, 514/232.8; 544/343, 116, 295
See application file for complete search history.

(56) References Cited

FOREIGN PATENT DOCUMENTS

| EP | 172 744 A2 | * | 2/1986 |
| HU | 195198 | | 3/1987 |
| WO | 93/24096 A | | 12/1993 |
| WO | 98/12181 A | | 3/1998 |
| WO | WO 98/1281 | | 3/1998 |
| WO | 98/45272 A | | 10/1998 |
| WO | WO 98/45272 | | 10/1998 |

OTHER PUBLICATIONS

Cecil Textbook of Medicine, 20th Edition, vol. 2., pp. 1739-1747.*
Rewcastle et al. {Journal of Medicinal Chemistry, vol. 30, No. 5, 1987, pp. 843-851}.*
Rewcastle et al; "Potential Antitumor Agents. 51. Synthesis and Anititumor Acitivity of Substituted Phenazine-1-Carboxamides"; Journal of Medicinal Chemistry, US, American, Chemical Society. Washington, vol. 30 No. 5, 1987, pp. 843-851, XP002051604.

* cited by examiner

*Primary Examiner*—Kahsay Habte
(74) *Attorney, Agent, or Firm*—Nixon & Vanderhye P.C.

(57) ABSTRACT

A compound which is a benzo[a]phenazine-11-carboxamide derivative of formula (I)

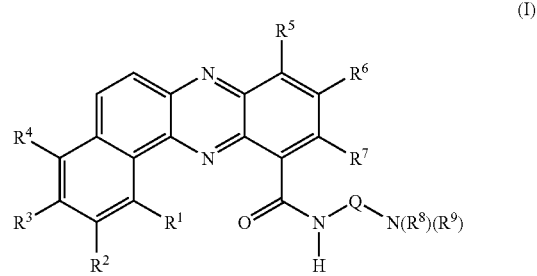

wherein each of $R^1$ to $R^4$, which are the same or different, is selected from hydrogen, halogen, hydroxyl, $C_1$–$C_6$ alkoxy which is unsubstituted or substituted, heteroaryloxy, $C_1$–$C_6$ alkyl which is unsubstituted or substituted, nitro, cyano, azido, amidoxime, $CO_2R^{10}$, $CON(R^{12})_2$, $OCON(R^{12})$, $SR^{10}$, $SOR^{11}$, $SO_2R^{11}$, $SO_2N(R^{12})_2$, $N(R^{12})_2$, $NR^{10}SO_2R^{11}$, $N(SO_2R_{11})_2$ $NR^{10}(CH_2)_nCN$, $NR^{10}COR^{11}$, $OCOR^{11}$ or $COR^{10}$;
each of $R^5$ to $R^7$, which are the same or different, is selected from hydrogen, halogen, hydroxy, $C_1$–$C_6$ alkoxy, $C_1$–$C_6$ alkyl, $SR^{10}$ and $N(R^{12})_2$;
Q is $C_1$–$C_6$ alkylene which is unsubstituted or substituted by (i) $C_1$–$C_6$ alkyl which is unsubstituted or substituted, (ii) hydroxy, provided that the hydroxy group is not α to either of the N atoms adjacent to Q in formula (I), (iii) $CO_2R^{10}$, or (iv) $CON(R^{12})$;
$R^8$ and $R^9$, which are the same or different, are each hydrogen or $C_1$–$C_6$ alkyl, or $R^8$ and $R^9$ together with the nitrogen atom to which they are attached form a saturated 5- or 6-membered N-containing heterocyclic ring which may include one additional heteroatom selected from O, N and S, or one of $R^8$ and $R^9$ is an alkylene chain optionally interrupted by O, N or S, which is attached to a carbon atom on the alkylene chain represented by Q to complete a saturated 5- or 6-membered N-containing heterocyclic ring as defined above;
$R^{10}$ is hydrogen, $C_1$–$C_6$ alkyl, $C_3$–$C_6$ cycloalkyl, benzyl or phenyl;
$R^{11}$ is $C_1$–$C_6$ alkyl, $C_3$–$C_6$ cycloalkyl, benzyl or phenyl;
each $R^{12}$, which are the same or different, is hydrogen, $C_1$–$C_6$ alkyl cycloalkyl, benzyl or phenyl, or the two $R^{12}$ groups form, together with the nitrogen atom to which they are attached a 5- or 6-membered saturated N-containing heterocyclic ring which may include 1 or 2 additional heteroatoms selected from O, N and S; and
n is 1, 2 or 3;
or a pharmaceutically acceptable salt thereof;
with the proviso that at least one of $R^1$ to $R^4$ is other than hydrogen.

These compounds are inhibitors of topoisomerase I and/or topoisomerase II and can be used to treat tumours, including tumours which express MDR.

11 Claims, No Drawings

PHARMACEUTICAL COMPOUNDS

This application is a continuation of prior application Ser. No. 10/148,601 filed Sep. 18, 2002 now abandoned, the entire content of which is hereby incorporated by reference, which application is a 371 of PCT/GB00/04609 filed Dec. 1, 2000 which designated the United States and claims benefit of GB 9928542.1 filed Dec. 2, 1999, the entire content of which is hereby incorporated by reference.

The present invention relates to substituted benzo[a] phenazine-11-carboxamides and derivatives thereof. These compounds are cytotoxic agents which have demonstrated topoisomerase I and topoisomerase II inhibition and have the ability to circumvent multidrug resistance mechanisms. They are therefore potential anticancer agents The topoisomerases are important cellular targets for a number of successful chemotherapeutic agents (Wang, Ann. Rev. Biochem, 65, 635–692, 1996) and are essential enzymes in the regulation of DNA topology which is required if cells are to divide and proliferate (Wang, loc cit). Drugs that target topoisomerase II, for example doxorubicin and etoposide, have been widely used in cancer chemotherapy (Hande, Biophys. Acta 1400, 173–184, 1998) while those that specifically target topoisomerase I, principally the camptothecin analogues, have made an important impact more recently, an example being CPT-11 for the treatment of colon cancer (Dancey et al, Br. J. Cancer 74, 327–338, 1996). More recently, topoisomerases have been shown to be therapeutic targets for antifungal, antibacterial and antiviral drugs (Chen et al, Rev. Pharmacol. Toxicol, 34, 191–218, 1994).

In addition to those compounds that specifically target topoisomerase I or II, several joint inhibitors of topoisomerase I and II have been identified and may also be beneficial in the treatment of solid tumours. These compounds include intoplicine (Riou et al, Cancer Res. 53, 5987–5993, 1993), DACA/XR5000 (Finlay et al, Eur. J. Cancer 32A, 708–714, 1996) and TAS-103 (Utsugi et al, J. Cancer Res, 88, 992–1002 1997) which are all in clinical evaluation. The advantage of joint inhibitors of topoisomerase I and II is their ability to avoid drug resistance and to target two key enzymes that affect the topology of DNA which are active at different points in the cell cycle.

It has now been found that a class of novel benzo[a] phenazine-11-carboxamides are inhibitors of topoisomerase I and topoisomerase II. Accordingly, the present invention provides a compound which is a benzo[a]phenazine-11-carboxamide derivative of formula (I)

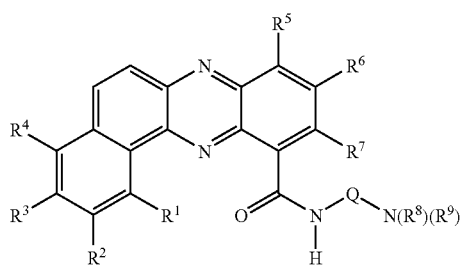

(I)

wherein each of $R^1$ to $R^4$, which are the same or different, is selected from hydrogen, halogen, hydroxyl, $C_1$–$C_6$ alkoxy which is unsubstituted or substituted, heteroaryloxy, $C_1$–$C_6$ alkyl which is unsubstituted or substituted, nitro, cyano, azido, amidoxime, $CO_2R^{10}$, $CON(R^{12})_2$, $OCON(R^{12})_2$, $SR^{10}$, $SOR^{11}$, $SO_2R^{11}$, $SO_2N(R^{12})_2$, $N(R^{12})_2$, $NR^{10}SO_2R^{11}$, $N(SO_2R^{11})_2$, $NR^{10}(CH_2)_nCN$, $NR^{10}COR^{11}$, $OCOR^{11}$ or $COR^{10}$;

each of $R^5$ to $R^7$, which are the same or different, is selected from hydrogen, halogen, hydroxy, $C_1$–$C_6$ alkoxy, $C_1$–$C_6$ alkyl, $SR^{10}$ and $N(R^{12})_2$;

Q is $C_1$–$C_6$ alkylene which is unsubstituted or substituted by (i) $C_1$–$C_6$ alkyl which is unsubstituted or substituted, (ii) hydroxy, provided that the hydroxy group is not $_\alpha$ to either of the N atoms adjacent to Q in formula (I), (iii) $CO_2R^{10}$, or (iv) $CON(R^{12})_2$;

$R^8$ and $R^9$, which are the same or different, are each hydrogen or $C_1$–$C_6$ alkyl, or $R^8$ and $R^9$ together with the nitrogen atom to which they are attached form a saturated 5- or 6-membered N-containing heterocyclic ring which may include one additional heteroatom selected from O, N and S, or one of $R^8$ and $R^9$ is an alkylene chain optionally interrupted by O, N or S, which is attached to a carbon atom on the alkylene chain represented by Q to complete a saturated 5- or 6-membered N-containing heterocyclic ring as defined above;

$R^{10}$ is hydrogen, $C_1$–$C_6$ alkyl, $C_3$–$C_{10}$ cycloalkyl, benzyl or phenyl;

$R^{11}$ is $C_1$–$C_6$ alkyl, $C_3$–$C_{10}$ cycloalkyl, benzyl or phenyl;

each $R^{12}$, which are the same or different, is hydrogen, $C_1$–$C_6$ alkyl, cycloalkyl, benzyl or phenyl, or the two $R^{12}$ groups form, together with the nitrogen atom to which they are attached, a 5- or 6-membered saturated N-containing heterocyclic ring which may include 1 or 2 additional heteroatoms selected from O, N and S; and n is 1, 2 or 3;

or a pharmaceutically acceptable salt thereof;

with the proviso that at least one of $R^1$ to $R^4$ is other than hydrogen.

In a preferred aspect of the invention the benzo[a]phenazine carboxamide-11-derivative is of formula (Ia)

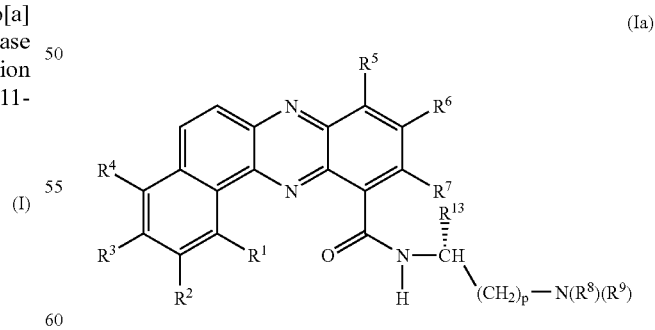

(Ia)

wherein $R^1$ to $R^9$ are as defined above;

p is 1 or 2; and $R^{13}$ is (i) hydrogen (ii) $C_1$–$C_6$ alkyl which is unsubstituted or substituted by hydroxy, aryl or $N(R^{12})_2$ in which $R^{12}$ is as defined above, (iii) $CO_2R^{10}$, (iv) $CON(R^{12})_2$, or (v) aryl.

When one of $R^8$ and $R^9$ in formula (I) is an alkylene chain which is attached to a carbon atom on Q, the compound of formula (I) has the following structure (Ib):

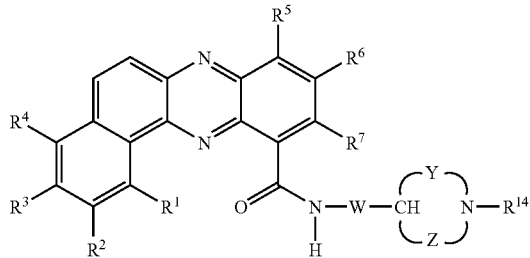

(Ib)

wherein $R^1$ to $R^7$ are as defined above for formula (I);
$R^{14}$ is hydrogen or $C_1-C_6$ alkyl;
W is a direct bond or a $C_1-C_5$ alkylene chain; and
Y and Z form, together with the N and C atoms to which they are attached, a saturated 5- or 6-membered N-containing heterocyclic ring which may include one additional O, N or S atom.

A $C_1-C_6$ alkyl group may be linear or branched. A $C_1-C_6$ alkyl group is typically a $C_1-C_4$ alkyl group, for example a methyl, ethyl, propyl, i-propyl, n-butyl, sec-butyl or tert-butyl group. A $C_1-C_6$ alkyl group is unsubstituted or substituted, typically by one or more groups selected from hydroxy-$C_1-C_6$ alkyl wherein the alkyl moiety is unsubstituted or substituted as specified herein for $C_1-C_6$ alkyl, $C_1-C_6$ alkoxy, phenyl, $N(R^{12})_2$ wherein $R^{12}$ is as defined above, and hydroxy. Examples of hydroxy-$C_1-C_6$-alkyl include, for instance, hydroxymethyl, 1-hydroxyethyl and 2-hydroxyethyl. $C_1-C_6$ alkylene is a $C_1-C_6$ alkyl group as defined above which is divalent.

An aryl group is typically an aromatic $C_6-C_{10}$ carbocyclic group, such as phenyl or naphthyl, which is unsubstituted or substituted by halogen, $C_1-C_6$ alkyl, OH, $C_1-C_6$ alkoxy, $NO_2$, $N(R^{12})_2$, $CO_2R^{10}$, CN or perhalo $C_1-C_6$ alkyl such as $CF_3$.

A halogen is F, Cl, Br or I. Preferably it is F, Cl or Br.

A $C_1-C_6$ alkoxy group may be linear or branched. It is typically a $C_1-C_4$ alkoxy group, for example a methoxy, ethoxy, propoxy, i-propoxy, n-propoxy, n-butoxy, sec-butoxy or tert-butoxy group. A $C_1-C_6$ alkoxy group is unsubstituted or substituted, typically by one or more groups selected from $N(R^{12})_2$, $CON(R^{12})_2$, hydroxy, $C_1-C_6$ alkoxy, $C_1-C_6$ alkyl, $C_2-C_6$ alkenyl, $C_2-C_6$ alkynyl, cyano, $CO_2R^{10}$, $COR^{10}$, a saturated 5- or 6-membered N-containing heterocyclic group or phenyl, the phenyl group being unsubstituted or substituted by one or more halogen atoms.

A $C_3-C_{10}$ cycloalkyl group may be cyclopropyl, cyclobutyl, cyclopentyl, cyclohexyl, or cycloheptyl. Typically it is $C_3-C_6$ cycloalkyl. A $C_2-C_6$ alkenyl group contains one or more unsaturated bonds. It may be, for instance, vinyl, propenyl, butenyl or pentenyl. A $C_2-C_6$ alkynyl group may be ethynyl, propynyl, butynyl or pentynyl. A saturated 5- or 6-membered N-containing heterocyclic ring may be, for example, piperidine, piperazine, morpholine or pyrrolidine.

A heteroaryloxy group is a group —OHet in which Het is an unsaturated 5- or 6-membered N-containing heterocyclic ring which may include one or more additional O, N or S atoms. Examples include furan, thiophene, pyrrole, indole, isoindole, pyrazole, imidazole, isoxazole, oxazole, thiazole, isothiazole, pyridine, quinoline, quinoxaline, isoquinoline, thienopyrazine, pyran, pyrimidine, pyridazine, pyrazine, purine and triazine. The aforesaid heterocyclic ring may be unsubstituted or substituted by one or more substituents, for instance one or more substituents selected from OH, halogen, $C_1-C_6$ alkyl which is unsubstituted or substituted, for example by halogen (such as $CF_3$), $C_1-C_6$ alkoxy, nitro and an amino group $N(R^{12})_2$ as defined above.

In a preferred aspect of the invention, $R^1$ to $R^3$ in formula (I), (Ia) or (Ib) are each hydrogen and $R^4$ is other than hydrogen. Typically $R^4$ is $C_1-C_6$ alkoxy, hydroxy, $C_1-C_6$ alkyl, hydroxy-$C_1-C_6$ alkyl, nitrile or halogen.

In a preferred series of compounds $R^4$ in formula (I), (Ia) or (Ib) is $C_1-C_6$ alkoxy or hydroxy, $R^7$ is hydroxy, and $R^1$ to $R^3$, $R^5$ and $R^6$ are each hydrogen. Also preferred are compounds wherein $R^4$ is $C_1-C_6$ alkoxy or hydroxy, $R_6$ is $C_1-C_6$ alkoxy, halogen or methylthio and $R^1$ to $R^3$, $R^5$ and $R^7$ are all hydrogen.

In formula (Ia) $R^{13}$ is preferably $C_1-C_6$ alkyl, more preferably methyl.

In formulae (I) and (Ia) a preferred option for Q is a $C_2$- or $C_3$-alkylene chain which is substituted α to the adjacent amide nitrogen atom by $C_1-C_6$ alkyl which is unsubstituted or substituted as defined above. Preferably the substituent on Q is unsubstituted $C_1-C_6$ alkyl or hydroxy-$C_1-C_6$ alkyl such as hydroxymethyl or hydroxyethyl. Typically the $C_2$- or $C_3$-alkylene chain is substituted a to the adjacent amide nitrogen atom by methyl, ethyl, isopropyl, hydroxymethyl, substituted hydroxymethyl or 1-hydroxyethyl.

Examples of preferred compounds of the invention are:

| Compound Name | Compound Number |
|---|---|
| 3-Methoxy-benzo[a]phenazine-11-carboxylic acid (2-dimethylamino-ethyl)-amide | 1 |
| 3-Hydroxy-benzo[a]phenazine-11-carboxylic acid (2-dimethylamino-ethyl)-amide | 2 |
| 4-Methoxy-benzo[a]phenazine-11-carboxylic acid (2-dimethylamino-ethyl)-amide | 3 |
| 4-Hydroxy-benzo[a]phenazine-11-carboxylic acid (2-dimethylamino-ethyl)-amide: hydrobromide salt | 4 |
| 2-Methoxy-benzo[a]phenazine-11-carboxylic acid (2-dimethylamino-ethyl)-amide | 5 |
| 2-Hydroxy-benzo[a]phenazine-11-carboxylic acid (2-dimethylamino-ethyl)-amide | 6 |
| 4-Nitro-benzo[a]phenazine-11-carboxylic acid (2-dimethylamino-ethyl)-amide | 7 |
| 4-Dimethylaminomethyl-3-hydroxy-benzo[a]phenazine-11-carboxylic acid (2-dimethylamino-ethyl)-amide | 8 |
| 3-Dimethylaminomethyl-4-hydroxy-benzo[a]phenazine-11-carboxylic acid (2-dimethylamino-ethyl)-amide | 9 |
| 9-Bromo-4-methoxy-benzo[a]phenazine-11-carboxylic acid (2-dimethylamino-ethyl)-amide | 10 |
| 4-Cyanomethoxy-benzo[a]phenazine-11-carboxylic acid (2-dimethylamino-ethyl)-amide | 11 |
| 4-Benzyloxy-benzo[a]phenazine-11-carboxylic acid (2-dimethylamino-ethyl)-amide | 12 |
| 4-Prop-2-ynyloxy-benzo[a]phenazine-11-carboxylic acid (2-dimethylamino-ethyl)-amide | 13 |
| 3,4-Dimethoxy-benzo[a]phenazine-11-carboxylic acid (2-dimethylamino-ethyl)-amide | 14 |
| 4-Ethoxy-benzo[a]phenazine-11-carboxylic acid (2-dimethylamino-ethyl)-amide | 15 |
| 4-Isobutoxy-benzo[a]phenazine-11-carboxylic acid (2-dimethylamino-ethyl)-amide | 16 |
| 4-(4-Chloro-benzyloxy)-benzo[a]phenazine-11-carboxylic acid (2-dimethylamino-ethyl)-amide | 17 |
| 4-(2-Methoxy-ethoxy)-benzo[a]phenazine-11-carboxylic acid (2-dimethylamino-ethyl)-amide | 18 |

-continued

| Compound Name | Compound Number |
|---|---|
| [11-(2-Dimethylamino-ethylcarbamoyl)-benzo[a]phenazin-4-yloxy]-acetic acid ethyl ester | 19 |
| 3-Bromo-4-hydroxy-benzo[a]phenazine-11-carboxylic acid (2-dimethylamino-ethyl)-amide | 20 |
| 4-(2-Hydroxy-ethoxy)-benzo[a]phenazine-11-carboxylic acid (2-dimethylamino-ethyl)-amide | 21 |
| 4-(Pyrimidin-2-yloxy)-benzo[a]phenazine-11-carboxylic acid (2-dimethylamino-ethyl)-amide | 22 |
| 4-(2-Morpholin-4-yl-ethoxy)-benzo[a]phenazine-11-carboxylic acid (2-dimethylamino-ethyl)-amide | 23 |
| 4-(3-Cyano-propoxy)-benzo[a]phenazine-11-carboxylic acid (2-dimethylamino-ethyl)-amide | 24 |
| 4-Methyl-benzo[a]phenazine-11-carboxylic acid(2-dimethylamino-ethyl)-amide | 25 |
| 4-Fluoro-benzo[a]phenazine-11-carboxylic acid(2-dimethylamino-ethyl)-amide | 26 |
| 4-(3-Dimethylamino-propoxy)-benzo[a]phenazine-11-carboxylic acid (2-dimethylamino-ethyl)-amide | 27 |
| 4-Methylsulfanyl-benzo[a]phenazine-11-carboxylic acid (2-dimethylamino-ethyl)-amide | 28 |
| 4-Carbamoylmethoxy-benzo[a]phenazine-11-carboxylic acid (2-dimethylamino-ethyl)-amide | 29 |
| 4-Methoxy-benzo[a]phenazine-11-carboxylic acid (3-amino-2-hydroxy-propyl)-amide | 30 |
| 4-Methoxy-benzo[a]phenazine-11-carboxylic acid (3-dimethylamino-propyl)-amide | 31 |
| 4-Bromo-benzo[a]phenazine-11-carboxylic acid (2-dimethylamino-ethyl)-amide | 32 |
| Acetic acid 11-(2-dimethylamino-ethylcarbamoyl)-benzo[a]phenazin-4-yl ester | 33 |
| 4-(2-Oxo-propoxy)-benzo[a]phenazine-11-carboxylic acid (2-dimethylamino-ethyl)-amide | 34 |
| 4-Methoxy-benzo[a]phenazine-11-carboxylic acid (2-dimethylamino-1-methyl-ethyl)-amide | 35 |
| 4-Cyano-benzo[a]phenazine-11-carboxylic acid (2-dimethylamino-ethyl)-amide | 36 |
| Ethyl-carbamic acid 11-(2-dimethylamino-ethylcarbamoyl)-benzo[a]phenazin-4-yl ester | 37 |
| 3-Nitro-benzo[a]phenazine-11-carboxylic acid (2-dimethylamino-ethyl)-amide | 38 |
| 4-Methanesulfonyl-benzo[a]phenazine-11-carboxylic acid (2-dimethylamino-ethyl)-amide | 39 |
| 4-Chloro-benzo[a]phenazine-11-carboxylic acid (2-dimethylamino-ethyl)-amide | 40 |
| 4-Azido-benzo[a]phenazine-11-carboxylic acid(2-dimethylamino-ethyl)-amide | 41 |
| 4-Amino-benzo[a]phenazine-11-carboxylic acid (2-dimethylamino-ethyl)-amide | 42 |
| [11-(2-Dimethylamino-ethylcarbamoyl)-benzo[a]phenazin-4-yloxy]-acetic acid trifluoro-acetate salt | 43 |
| 4-Acetylamino-benzo[a]phenazine-11-carboxylic acid (2-dimethylamino-ethyl)-amide | 44 |
| 11-(2-Dimethylamino-ethylcarbamoyl)-benzo[a]phenazine-4-carboxylic acid methyl ester | 45 |
| 4-Bis-(Methanesulfonylamino)-benzo[a]phenazine-11-carboxylic acid (2-dimethylamino-ethyl)-amide | 46 |
| 3-Amino-benzo[a]phenazine-11-carboxylic acid (2-dimethylamino-ethyl)-amide | 47 |
| 4-(N-Hydroxycarbamimidoyl)-benzo[a]phenazine-11-carboxylic acid (2-dimethylamino-ethyl)-amide | 48 |
| 4-Hydroxymethyl-benzo[a]phenazine-11-carboxylic acid (2-dimethylamino-ethyl)-amide | 49 |
| 11-(2-Dimethylamino-ethylcarbamoyl)-benzo[a]phenazine-4-carboxylic acid, trifluoroacetate salt | 50 |
| 4-Methylsulfamoyl-benzo[a]phenazine-11-carboxylic acid (2-dimethylamino-ethyl)-amide; trifluoro-acetate | 51 |
| 3-Methylsulfamoyl-benzo[a]phenazine-11-carboxylic acid (2-dimethylamino-ethyl)-amide; trifluoro-acetate | 52 |
| 3-Acetylamino-benzo[a]phenazine-11-carboxylic acid (2-dimethylamino-ethyl)-amide | 53 |
| 4-Dimethylamino-benzo[a]phenazine-11-carboxylic acid (2-dimethylamino-ethyl)-amide | 54 |
| 4-Methanesulfonylamino-benzo[a]phenazine-11-carboxylic acid (2-dimethylamino-ethyl)-amide | 55 |
| 3-Methanesulfonylamino-benzo[a]phenazine-11-carboxylic acid (2-dimethylamino-ethyl)-amide | 56 |
| 4-Dimethylsulfamoyl-benzo[a]phenazine-11-carboxylic acid (2-dimethylamino-ethyl)-amide | 57 |
| 3-Dimethylsulfamoyl-benzo[a]phenazine-11-carboxylic acid (2-dimethylamino-ethyl)-amide | 58 |
| 4-(Cyanomethyl-amino)-benzo[a]phenazine-11-carboxylic acid (2-dimethylamino-ethyl)-amide | 59 |
| 4,10-Dimethoxy-benzo[a]phenazine-11-carboxylic acid (2-dimethylamino-ethyl)-amide | 60 |
| 4-Methoxy-benzo[a]phenazine-11-carboxylic acid (2-dimethylamino-propyl)-amide | 61 |
| Benzo[a]phenazine-4,11-dicarboxylic acid 4-amide 11-[(2-dimethylamine-ethyl)-amide]; triflouroacetic acid salt | 62 |
| 1-Chloro-4,10-dimethoxy-benzo[a]phenazine-11-carboxylic acid (2-dimethylamino-ethyl)-amide | 63 |
| 3-Sulfamoyl-benzo[a]phenazine-11-carboxylic acid (2-dimethylamino-ethyl)-amide | 64 |
| 4-Methoxy-benzo[a]phenazine-11-carboxylic acid (2-dimethylamino-1,1-dimethyl-ethyl)-amide | 65 |
| 2-Nitro-benzo[a]phenazine-11-carboxylic acid (2-dimethylamino-ethyl)-amide | 66 |
| 4-Methoxy-8-methyl-benzo[a]phenazine-11-carboxylic acid (2-dimethylamino-ethyl)-amide | 67 |
| 4,10-Dihydroxy-benzo[a]phenazine-11-carboxylic acid (2-dimethylamino-ethyl)-amide | 68 |
| 3-Dimethylamino-2-[(4-methoxy-benzo[a]phenazine-11-carbonyl)-amino]-propionic acid methyl ester. Trifluoroacetic acid salt | 69 |
| 3-Dimethylamino-2-[(4-methoxy-benzo[a]phenazine-11-carbonyl)-amino]-propionic acid; hydrochloride | 70 |
| 4-Methoxy-benzo[a]phenazine-11-carboxylic acid (1-dimethylaminomethyl-propyl)-amide | 71 |
| 4,10-Dimethoxy-benzo[a]phenazine-11-carboxylic acid (2-dimethylamino-1-methyl-ethyl)-amide | 72 |
| 9-Chloro-4-methoxy-benzo[a]phenazine-11-carboxylic acid (2-dimethylamino-ethyl)-amide | 73 |
| 4-Methoxy-benzo[a]phenazine-11-carboxylic acid (1-dimethylaminomethyl-2-methyl-propyl)-amide | 74 |
| 4-Methoxy-benzo[a]phenazine-11-carboxylic acid (2-dimethylamino-1-hydroxymethyl-ethyl)-amide | 75 |
| 4-Methoxy-benzo[a]phenazine-11-carboxylic acid (1-dimethylaminomethyl-2-phenyl-ethyl)-amide | 76 |
| 4-Methoxy-benzo[a]phenazine-11-carboxylic acid (2-dimethylamino-1-(S)-methyl-ethyl)-amide | 77 |
| 4-Methoxy-benzo[a]phenazine-11-carboxylic acid (2-dimethylamino-1-(R)-methyl-ethyl)-amide | 78 |
| 4-Nitro-benzo[a]phenazine-11-carboxylic acid (2-dimethylamino-1-methyl-ethyl)-amide | 79 |
| 3-Nitro-benzo[a]phenazine-11-carboxylic acid (2-dimethylamino-1-methyl-ethyl)-amide | 80 |
| 4-Methoxy-benzo[a]phenazine-11-carboxylic acid (2-dimethylamino-1-(S)-hydroxymethyl-ethyl)-amide | 81 |
| 4-Methoxy-10-methylamino-benzo[a]phenazine-11-carboxylic acid (2-dimethylamino-ethyl)-amide | 82 |
| 10-Hydroxy-4-methoxy-benzo[a]phenazine-11-carboxylic acid (2-dimethylamino-1(R)-methyl-ethyl)-amide | 83 |
| 4-Methoxy-benzo[a]phenazine-11-carboxylic acid (1-dimethylaminomethyl-2-hydroxy-propyl)-amide | 84 |
| 10-Hydroxy-4-methoxy-benzo[a]phenazine-11-carboxylic acid (2-dimethylamino-ethyl)-amide | 85 |
| 4-Methoxy-benzo[a]phenazine-11-carboxylic acid (2-piperidin-1-yl-ethyl)-amide | 86 |
| 4-Methoxy-benzo[a]phenazine-11-carboxylic acid [1-dimethylamino-1-(2-hydroxyethyl)]-ethylamide | 87 |
| 10-Amino-4-methoxy-benzo[a]phenazine-11-carboxylic acid (2-dimethylamino-ethyl)-amide | 88 |
| 4-Methoxy-benzo[a]phenazine-11-carboxylic acid (2-morpholin-4-yl-ethyl)-amide | 89 |
| 4-Methoxy-benzo[a]phenazine-11-carboxylic acid (2-pyrrolidin-1-yl-ethyl)-amide | 90 |
| 4-Methoxy-benzo[a]phenazine-11-carboxylic acid {2-[bis-(2-hydroxy-ethyl)-amino]-ethyl}-amide | 91 |
| 4-Methoxy-benzo[a]phenazine-11-carboxylic acid (2-diethylamino-ethyl)-amide | 92 |

-continued

| Compound Name | Compound Number |
|---|---|
| 4-Methoxy-9-methylsulfanyl-benzo[a]phenazine-11-carboxylic acid (2-dimethylamino-ethyl)-amide | 93 |
| 4,9-Dimethoxy-benzo[a]phenazine-11-carboxylic acid (2-dimethylamino-ethyl)-amide | 94 |
| 4,10-Dimethoxy-benzo[a]phenazine-11-carboxylic acid (2-dimethylamino-1(S)-hydroxymethyl-ethyl)-amide | 95 |
| 4-Methoxy-benzo[a]phenazine-11-carboxylic acid (2-methylamino-ethyl)-amide | 96 |
| 10-Hydroxy-4-methoxy-benzo[a]phenazine-11-carboxylic acid (2-dimethylamino-1(S)-hydroxymethyl-ethyl)-amide | 97 |
| (R)-4-Methoxy-benzo[a]phenazine-11-carboxylic acid(1-dimethylaminomethyl-2-methyl-propyl)-amide | 98 |
| 4-Methoxy-benzo[a]phenazine-11-carboxylic acid (1-methyl-pyrrolidin-3-(R)-yl)-amide | 99 |
| 4-Methoxy-benzo[a]phenazine-11-carboxylic acid (2,3-(bis)-dimethylamino-propyl)amide | 100 |

Compounds of formula (I) may be prepared by a process which comprises:

(a) treating an activated derivative of a compound of formula (II):

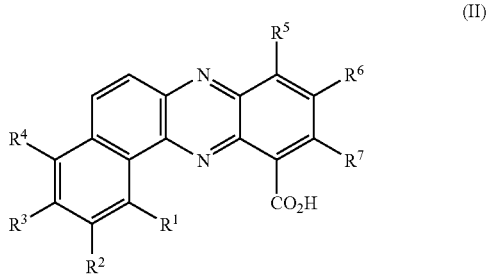

wherein $R^1$ to $R^7$ are as defined above, with an amine of formula (III):

wherein Q, $R^8$ and $R^9$ are as defined above; or (b) treating a compound of formula (IV):

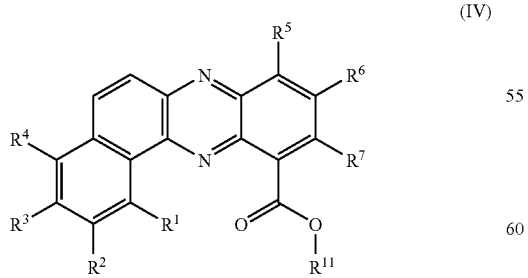

wherein $R^1$ to $R^7$ and $R^{11}$ are as defined above, with a compound of formula (III) as defined above, either in an organic solvent or neat and at an elevated temperature; and (c) if desired, converting one resulting benzo(a)phenazine-11-carboxamide derivative of formula (I) into another such derivative, and/or converting a benzo[a]phenazine-11-carboxamide derivative of formula (I) into a pharmaceutically acceptable salt thereof.

The optical purity of resulting compounds that have an optically active centre, for instance the benzo[a]phenazine-11-carboxamide derivatives of formula (Ia) and the salts thereof, may be determined by the addition of an NMR shift reagent such as 2,2,2-trifluoro-1(9-anthryl)ethanol to NMR samples of the homochiral compounds.

The starting compounds of formula (II) and their esters (the compounds of formula (IV)) are novel and thus constitute a further aspect of the present invention.

In step (a) the carboxylic acid grouping in formula (II) may be activated as the corresponding acid chloride which may be obtained by treating the free carboxylic acid of formula (II) with thionyl chloride. Alternatively the carboxylic acid grouping can be activated by treatment with an appropriate amide-coupling reagent such as 1,1'-carbonyldiimidazole.

The reaction between the activated derivative of the compound of formula (II) and the amine of formula (III) is typically conducted in an organic solvent. Suitable solvents include dimethylformamide and dichloromethane. The steps of activating the compound of formula (II) and treating the resulting activated derivative with the amine of formula (III) may take place without intermediate isolation of the activated derivative. In that case the process typically comprises combining the activating agent or coupling agent with the compound of formula (II) in an organic solvent and adding to the resulting reaction mixture the amine of formula (III).

A compound of formula (II) may be prepared by a process which comprises:

(a) treating a 1,2-naphthoquinone of formula (V):

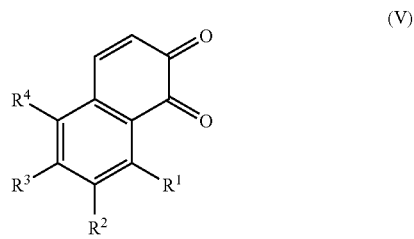

wherein $R^1$ to $R^4$ are as defined above for formula (I), with a benzoic acid of formula (VI):

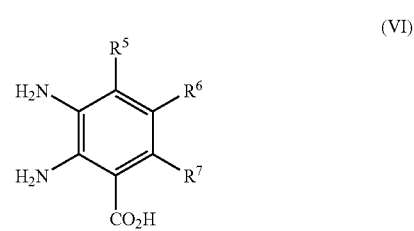

or an ester or salt thereof, wherein $R^5$, $R^6$ and $R^7$ are as defined above for formula (I), in an organic solvent, optionally in the presence of an acid. The solvent may be, for example, ethanol or acetic acid. By using 1 to 5 equivalents of mineral acid in the reaction mixture the regioselectivity of the reaction may be controlled. The use of about 2 equivalents or more of the acid, for instance from 1.5 to 5 equivalents, yields exclusively the desired regioisomer namely a benzo[a]phenazine-11-carboxylic acid of formula (II). The mineral acid is preferably hydrochloric acid, more preferably concentrated hydrochloric acid. The salt of the benzoic acid of formula (VI) is typically the acetate salt.

The 1,2-naphthoquinone of formula (V) may be prepared by treating the corresponding 1-tetralone of formula (VII):

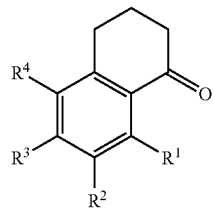

(VII)

wherein $R^1$ to $R^4$ are as defined above for formula (I), with selenium dioxide in accordance with the procedure described in Tetrahedron Letters 1997, 4219–4220. The 1-tetralones of formula (VII) are known compounds or may be prepared from known compounds by published methods, for instance as described in the reference examples which follow, adapted where necessary using conventional laboratory techniques to achieve the desired definitions of $R^1$ to $R^4$. Published methods include those described in J. Med. Chem 1997, 40, 3014–3024; J. Org. Chem. 1984, 4226; JACS. 1994, 116 pp. 4852–4857 and J. Med. Chem. 1997 p. 1049.

The benzoic acids of formula (VI) are known compounds or may be prepared from known compounds using published methods, adapted where necessary using conventional laboratory techniques to achieve the desired definitions of $R^5$ to $R^7$. Published methods include those described in J. Chem. Soc. Perkin Trans. I, 1984, p2019 and J. Med. Chem 1987, p. 843.

A compound of formula (II) may also be prepared by a process which comprises:

(a) treating a 2-halo-3-nitrobenzoic acid of formula (VIII):

(VII)

wherein Hal is Cl, Br, I or F, with a naphthylamine of formula (IX):

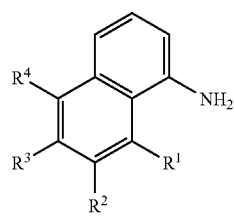

(IX)

wherein $R^1$ to $R^4$ are as defined above for formula (I); and (b) submitting the resulting compound of formula (X):

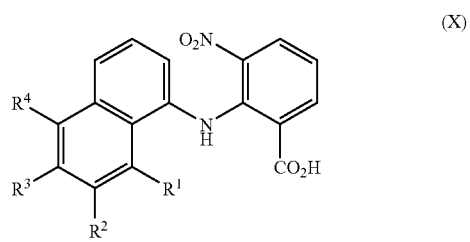

(X)

wherein $R^1$ to $R^4$ are as defined above, to reductive cyclisation.

Step (a) is typically conducted in an organic solvent. Suitable examples include butane-2,3-diol and ethylene glycol. Step (b) is generally carried out by treatment of the compound of formula (X) with $NaBH_4$ in sodium methoxide, sodium ethoxide or aqueous NaOH. The process is described in J. Med. Chem. 1987, 30, 843–851.

A compound of formula (IV) may be prepared by esterification of a corresponding compound of formula (II) under standard reaction conditions, for instance by treatment of the free carboxylic acid-compound of formula (II) with an alcohol of formula $R^{11}$—OH wherein $R^{11}$ is as defined above.

Amines of formula (III) are known and commercially available compounds or may be produced from commercially available starting materials using conventional techniques, for instance as described in reference example 2 which follows.

A compound of formula (I) may be converted into another compound of formula (I) by conventional methods. For instance, a compound of formula (I) containing an esterified hydroxy group such as —OCOMe may be converted into a compound of formula (I) containing a free hydroxy group by hydrolysis, for instance alkaline hydrolysis. A compound of formula (I) containing a free hydroxy group may be converted into a compound of formula (I) containing an esterified hydroxy group by esterification, for instance by reaction with a suitable carboxylic acid, acid halide or acid anhydride. A compound containing a free hydroxy group may also be converted to a compound containing a carbamic acid ester grouping, for instance by treatment with triethylamine and ethyl isocyanate in an aprotic polar solvent, for instance dimethylformamide.

A compound of formula (I) containing a nitro group may be converted into a compound of formula (I) containing an amino group by reduction, for instance by treatment with indium and a saturated $NH_4Cl$ solution in an organic solvent.

A compound containing a $C_1$–$C_6$ alkoxy group may be converted into a compound containing a hydroxy group, for instance by treatment with boron tribromide in a halogenated hydrocarbon solvent, for instance dichloromethane, or with sodium thioethoxide in dimethyl formamide. A compound containing a hydroxy group may be converted into a compound containing an optionally substituted $C_1$–$C_6$ alkoxy group, for instance by treatment with an appropriate alkylating agent in the presence of a base. A compound containing a carboxy group may be converted to a compound containing a hydroxymethyl group by reduction, for instance by treatment with $LiAlH_4$ in tetrahydrofuran.

A compound containing a halogen may be converted into a compound containing an alkylsulfanyl or alkoxy group, for instance by treatment with a thioalkoxide or alkoxide salt, respectively, in an organic solvent. A compound containing a nitrile group may be converted into a compound containing an N-hydroxycarbamimidoyl group, for instance by treatment with hydroxylamine (optionally in the form of a salt) in the presence of a base such as potassium carbonate.

A compound substituted by alkylaminomethyl at a benzene ring position may be prepared under Mannich reaction conditions by treating a compound that is substituted by hydroxy ortho to the (unsubstituted) ring position in question with acetic acid followed by treatment with an alkylamine and a solution of formaldehyde in water. A compound of formula (I) may be acetylated, for instance on an amine group to form an acetylamino substituent, by treatment with acetyl chloride under suitable conditions.

Benzo[a]phenazine-11-carboxamide derivatives may be converted into pharmaceutically acceptable salts, and salts may be converted into the free compound, by conventional methods. Pharmaceutically acceptable salts of the benzo[a]phenzine-11-carboxamide derivatives of formula (I) include salts of inorganic acids such as hydrochloric acid, hydrobromic acid and sulfuric acid, and salts of organic acids such as acetic acid, oxalic acid, malic acid, methanesulfonic acid, trifluoroacetic acid, benzoic acid, citric acid and tartaric acid. In the case of compounds of formula I wherein any one of $R^1$–$R^4$ and $R^{10}$ is COOH, the salts include both the above-mentioned salts and the salts of sodium, potassium, calcium and ammonium, which are prepared by treating the compound of formula 1 with or the acid salts with the corresponding metal base or ammonia.

Multi-drug resistance (MDR) is a phenomenon whereby cells which are typically sensitive to chemotherapeutic agents develop resistance to those agents and to a wide range of unrelated drugs. MDR represents a major obstacle in the successful clinical therapy of cancer. Cancer cells which exhibit MDR can display a number of diverse cellular alterations including overexpression of P-glycoprotein (P-gp), overexpression of multidrug resistance associated protein (MRP), reduction in levels of topoisomerase II (termed atypical drug resistance) and qualitative changes in expression of topoisomerase I. MDR is a very important clinical problem with many tumors developing resistance to many chemotherapeutic agents including those that specifically target topoisomerase I and/or topoisomerase II.

By simultaneously inhibiting topoisomerase I and II, compounds such as DACA (Finlay et al, Eur. J. Cancer 32A, 708–714, 1996) have shown no loss of activity when resistance develops to camptothecin or amsacrine due to alteration of either topoisomerase I or II respectively. Qualitatively different cell cycle events have been obtained with inhibitors of topoisomerase I or II. (Kaufman, Biochim. Biophys. Acta 1400, 195–212, 1998). Joint inhibitors of topoisomerases I and II appear to combine the properties of the individual specific inhibitors and act across the cell cycle (Haldane et al, Cancer Chemother. Pharmacol. 32: 463–470, 1993), resulting in a greater antitumour activity (Riou et al, Cancer Res. 53, 5987–5993, 1993).

MDR due to the overexpression of membrane transporters such as P-glycoprotein (Gottesman et al, Annu. Rev. Biochem. 62, 385–427, 1993) and MRP (Loe et al, Eur. J. Cancer 32A, 945–957, 1996) is known to reduce the clinical efficacy of chemotherapeutic agents such as paclitaxel, etoposide and doxorubicin. Agents that avoid such MDR mechanisms are predicted to show therapeutic benefit in the treatment of cancer.

Benzo[a]phenazine-11-carboxamide derivatives of formula I, their pharmaceutically acceptable salts and hydrates and solvates thereof (hereinafter referred to as "the present compounds") have been found in biological tests to have activity as inhibitors of topoisomerase I and II. In one aspect of the invention the present compounds are joint inhibitors of topoisomerase I and topoisomerase II.

The present compounds may therefore be used as inhibitors of topoisomerase I. Alternatively the present compounds may be used as inhibitors of topoisomerase II. In a further embodiment they may be used as joint inhibitors of topoisomerase I and topoisomerase II. They have been shown to kill human tumour cells and avoid MDR mechanisms. They therefore have potential in the treatment of cancer. Examples of types of cancer that the present compounds can be used to treat include leukaemias, lymphomas, sarcomas, carcinomas and adenocarcinomas. Specific examples include breast, colon, brain, lung, ovary, pancreatic, stomach and skin cancer.

A human or animal patient harbouring a tumour may be treated by a method comprising the administration thereto of one of the present compounds. In particular, a method of treating human tumours, including those which express MDR, for instance the types of MDR referred to above, comprises administering a therapeutically effective amount of one of the present compounds to a patient harbouring a tumour. All types of tumour may thus be treated, both those which express MDR and those which do not. The present compound is administered in an amount effective to reduce or eliminate the tumour. In one aspect of the invention the present compound is administered orally. In another aspect the present compound is administered by a parenteral route, for instance intravenously.

Owing to their activity as inhibitors of topoisomerase I and topoisomerase II the present compounds may also be used as antiviral, antibacterial or antifungal agents.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration when a compound of the invention is administered alone to adult humans is 0.001 to 500 mg/kg, most commonly in the range of 0.01 to 100 mg/kg body weight. Such a dosage may be given, for example, from 1 to 5 times daily by bolus infusion, infusion over several hours and/or repeated administration.

A benzo[a]phenazine-11-carboxamide derivative of formula (I) or a pharmaceutically acceptable salt thereof is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. An agent for use in the treatment of tumours, including those which express MDR, comprising one of the present compounds is therefore provided.

The present compounds may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occuring phosphatides, for example soy bean lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and polyethylene glycols;

E) Topically, in the form of creams, ointments, jellies, collyriums, solutions or suspensions.

Daily dosages can vary within wide limits and will be adjusted to the individual requirements in each particular case. In general, for administration to adults, an appropriate daily dosage is in the range of about 5 mg to about 500 mg, although the upper limit may be exceeded if expedient. The daily dosage can be administered as a single dosage or in divided dosages.

The invention will be further illustrated in the Examples which follow.

REFERENCE EXAMPLE 1

Preparation of Compounds of General Formula (II)

Reference Example 1A

4-Methoxy-benzo[a]phenazine-11-carboxylic acid (II.1)

A mixture of 5-methoxy-[1,2]naphthoquinone (prepared by treatment of 5-methoxytetralone with selenium dioxide, A. Bekaert et al Tetrahedron Letters 38, 24, 4219–4220, 1997) (1.98 g), 2,3-diamino-benzoic acid, diacetate salt, (J. Chem. Soc. Perkin. Trans I, 1984, p2019) (4.03 g) and conc. hydrochloric acid (2.2 mL) was heated to reflux in ethanol (20 mL) for 4 hours. The reaction mixture was cooled and the precipitate collected by filtration, and washed with ethanol and ether to yield the title compound as a beige solid (2.74 g).

NMR: (DMSO) 4.05 (s,3H), 7.50(1H,d), 7.84–7.87(1H, m), 7.99(1H,d), 8.08–8.10(1H,m), 8.41–8.49(3H,m), 8.63 (1H,d).

Reference Example 1B

4-Methyl-benzo[a]phenazine-11-carboxylic acid (II.2)

5-Methyl-1-tetralone was prepared from o-tolualdehyde according to the literature (J. Med Chem 1997, 40, 3014–3024). Treatment of 5-methyl-1-tetralone with selenium dioxide as described in Reference Example 1A yielded 5-methyl-[1,2]naphthoquinone. This was reacted with 2,3-diamino-benzoic acid, diacetate salt, as described in Reference Example 1A to yield the title compound.

NMR, d6-DMSO 9.02(1H,d), 8.51 (1H,dd), 8.47–8.44 (2H,m), 8.11–8.05(2H,m), 7.85–7.78(2H,m), 2.79(3H,s).

Commencing with the appropriately substituted aldehydes, the following compounds of Formula (II) were prepared in an analogous manner:

4-Fluoro-benzo[a]phenazine-11-carboxylic acid (II.3) was prepared from 2-fluorobenzaldehyde NMR, d6-DMSO, 8.97(1H,d), 8.51(1H,dd), 8.43(1H,dd), 8.38(1H,d), 8.11–8.06(2H,m), 7.95(1H,m), 7.80(1H,m);

3,4-Dimethoxy-benzo[a]phenazine-11-carboxylic acid (II.4) was prepared from 2,3-dimethoxybenzaldehyde;

NMR, CDCl3, 8.79(1H,d), 8.48(2H,d),8.37(1H,d), 8.05 (1H,t), 7.95(1H,d),7.76(1H,d), 4.04(3H,s), 3.98(3H,s).

Reference Example 1C

4-Bromo-benzo[a]phenazine-11-carboxylic acid (II.5)

2-Bromobenzyl bromide was converted into 5-bromotetralone according to the literature (J. Org. Chem. 1984, p4226). Treatment of 5-bromotetralone with selenium dioxide as described in Referene Example 1A yielded 5-bromo-[1,2]naphthoquinone, which was coupled with 2,3-diamino-benzoic acid, diacetate salt, as described in Reference Example 1A to yield the title compound.

NMR d6-DMSO, 9.24(1H,d), 8.48(2H,m), 8.33(1H,m), 8.26(1H,m), 8.20(1H,d), 8.08(1H,t), 7.87(1H,t)

Reference Example 1D

4-Cyano-benzo[a]phenazine-11-carboxylic acid (II.6)

To a solution of 5-bromotetralone (see Reference Example 1C)(5.0 g) in N,N-dimethylformamide (20 mL) was added copper (1) cyanide (6.39 g) and the reaction mixture heated to reflux for 20 hours. The reaction mixture was then cooled to 80° C. and a solution of $FeCl_3 \cdot 6H_2O$ (24 g) in water (38 mL) was added. After stirring for a further 45 minutes the reaction mixture was cooled, diluted with water, extracted into toluene, washed with water, dried ($MgSO_4$) and the solvent removed in vacuo to yield 5-cyano-1-tetralone as a yellow solid.

Treatment of 5-cyano-1-tetralone with selenium dioxide as described in Reference Example 1A yielded the corresponding 5-cyano-[1,2]naphthoquinone, which was coupled with 2,3-diamino-benzoic acid, diacetate salt, as described to yield the title compound.

NMR (d6-DMSO), 8.10–8.18(2H,m), 8.33(1H,d), 8.43 (2H,m), 8.48–8.54(2H,m), 9.48(1H,d). MS DCI/NH3 m/z 300 (MH+)

Reference Example 1E

4-Chloro-benzo[a]phenazine-11-carboxylic acid (II.7)

5-Amino-1-tetralone was prepared from α-tetralone according to the literature (J. Am. Chem. Soc. 1994, p4852). A mixture of 5-amino-1-tetralone (80 mg) and concentrated hydrochloric acid (1 mL) was cooled to 0° C. A solution of sodium nitrite (35 mg) in water (0.5 mL) was added dropwise to the stirring solution. The cold diazonium solution was then poured rapidly onto a stirring solution of copper (I) chloride (62 mg) in concentrated hydrochloric acid (1 mL). The reaction mixture was allowed to warn to ambient temperature and then stirred for 1.5 hours. The mixture was then extracted with ethyl acetate, washed with water, dried ($MgSO_4$) and the solvent removed in vacuo to yield 5-chloro-1-tetralone as a brown solid (87 mg).

Treatment of 5-chloro-tetralone with selenium dioxide as described in Reference Example 1A yielded 5-chloro-[1,2] naphthoquinone which was coupled with 2,3-diamino-benzoic acid, diacetate salt, as described in Reference Example 1A to yield the title compound.

Reference Example 1F

4-Methanesulphonyl-benzo[a]phenazine-11-carboxylic acid (II.8)

5-Methylsulphanyl-1-tetralone was prepared from 5-hydroxy-1-tetralone according to the literature (J. Med. Chem. 1997, p1049). A mixture of 5-methylsulphanyl-1-tetralone (221 mg) and 3-chloroperbenzoic acid (595 mg) was stirred at room temperature for 2 hours. The reaction mixture was then extracted with dichloromethane, washed with water, dried ($Na_2SO_4$) and the solvent removed in vacuo to yield 5-methanesulphonyl-1-tetralone as an off-white solid (210 mg).

Treatment of 5-methanesulphonyl-1-tetralone with selenium dioxide as described in Reference Example 1A yielded 5-methanesulfonyl-[1,2]naphthoquinone which was coupled with 2,3-diamino-benzoic acid, diacetate salt, as described in Reference Example 1A to yield the title compound.

NMR, d6-DMSO, 9.61(1H,d), 9.03(1H,d), 8.56(2H,m), 8.43(1H,d), 8.32(1H,m), 8.16(2H,m), 3.51 (3H,s). MS, DCI/NH3) m/z 353 (MH+).

Reference Example 1G

4-Azido-benzo[a]phenazine-11-carboxylic acid (II.9)

5-Amino-1-tetralone was prepared from α-tetralone according to the literature (J. Am. Chem. Soc. 1994, p4852). To a cold solution of 5-amino-1-tetratone (415 mg) in water (2 mL) and concentrated hydrochloric acid (5 mL) was added a solution of sodium nitrite (186 mg) in water (1.2 mL), maintaining low temperature. After 40 minutes a solution of sodium azide (184 mg) in water (1.2 mL) was added dropwise. The reaction mixture was allowed to warm to room temperature. After one further hour the reaction was quenched with water, extracted into ether, washed with sodium bicarbonate solution, dried (MgSO$_4$) and the solvent removed in vacuo to yield crude material which was purified using flash chromatography to yield 5-azido-1-tetralone (77 mg).

Treatment of 5-azido-1-tetralone with selenium dioxide as described in Reference Example 1A yielded 5-azido-[1,2] naphthoquinone which was coupled with 2,3-diamino-benzoic acid, diacetate salt, as described in Reference Example 1A to yield the title compound.

Reference Example 1H

Benzo[a]phenazine-4,11-dicarboxylic acid 4-methyl ester (II.10)

Methyl 5-oxo-5,6,7,8-tetrahydro-1-naphthoate was prepared according to the literature (J. Org. Chem. 1976, p2918) from 2-methyl-2,6,7,8-tetrahydro-chromen-5-one (Tetrahedron Letters, 1975, p3407). Treatment of methyl 5-oxo-5,6,7,8-tetrahydro-1-naphthoate with selenium dioxide as described in Reference Example 1A yielded the corresponding 1,2-naphthoquinone, 5,6-dioxo-5,6-dihydro-naphthalene-1-carboxylic acid methyl ester, which was coupled with 2,3-diamino-benzoic acid, diacetate salt, as described in Reference Example 1A to yield the title compound.

NMR, d6-DMSO, 9.47(1H,d), 9.02(1H,d), 8.53(1H,d), 8.44(2H,m), 8.20(1H,d), 8.10(2H,m), 4.03(3H,s).

Reference Example 1I

4-Ethoxy-benzo[a]phenazine-11-carboxylic acid (II.11)

A mixture of 5-hydroxy-1-tetralone (2.00 g) and sodium hydroxide (493 mg) was warmed in ethanol (40 mL) to 50° C. Ethyl iodide (3.94 mL) was then added and the reaction mixture was heated at reflux for 16 hours. The reaction mixture was diluted with 2N hydrochloric acid, extracted into ethyl acetate, dried and the solvent removed in vacuo to yield 5-ethoxy-1-tetralone as a white solid (2.06 g)

Treatment of 5-ethoxy-1-tetralone with selenium dioxide as described in Reference Example 1A yielded 5-ethoxy-[1, 2]naphthoquinone which was coupled with 2,3-diamino-benzoic acid, diacetate salt, as described to yield the title compound.

NMR: d6-DMSO. 1.52(3H,q), 4.33(2H,t), 7.50(1H,d), 7.85–7.90(1H,m), 8.00(1H,d), 8.08–8.11(1H,m), 8.45–8.55 (3H,m), 8.68(1H,d).

Reference Example 1J

4-Methylsulfanyl-benzo[a]phenazine-11-carboxylic acid (II.12)

To a stirred solution of 4-fluoro-benzo[a]phenazine-11-carboxylic acid (II.3, see Reference Example 1B (58 mg) in dry DMSO (3 mL) was added sodium thiomethoxide (55 mg) and the reaction mixture heated at 100° C. for 1.5 hours and 130° C. for 1 hour. The reaction mixture was then cooled to room temperature, quenched with acetic acid, extracted with ethyl acetate, washed with water, dried and the solvent removed in vacuo to yield the title compound as a red solid (37 mg).

NMR, d6-DMSO, 9.00(1H,d), 8.52(2H,m), 8.45(1H,d), 8.11(2H,m), 7.91(2H,m), 2.70(3H,s). MS, DCI/NH3, m/z=321(MH+, 100%)

Reference Example 1K

4-Benzyloxy-benzo[a]phenazine-11-carboxylic acid (II.13)

To a solution of 4-methoxy-benzo[a]phenazine-11-carboxylic acid (II.1, see Reference Example 1A) (441 mg) in dichloromethane (30 mL) cooled to 0° C. was added a 1.0M solution of boron tribromide in dichloromethane (7.25 mL). The reaction mixture was allowed to warm to room temperature and then stirred for 16 hours. The mixture was then poured onto ice/water yielding 4-hydroxy-benzo[a]phenazine-11-carboxylic acid as a red/brown solid which was collected by filtration and air dried (230 mg).

NMR: d6-DMSO. 7.35(1H,d), 7.75(1H,m), 7.92(1H,d), 8.08(1H,m), 8.47–8.55(4H,m), 10.72(1H,broad).

A mixture of 4-hydroxy-benzo[a]phenazine-11-carboxylic acid (80 mg), sodium hydroxide (34 mg) and benzyl bromide (100 μL) in ethanol (2 mL) was heated to reflux for 4 hours. The reaction mixture was then cooled, diluted with ethyl acetate, washed with dilute acid, dried (MgSO$_4$) and the solvent removed in vacuo to yield the crude title compound as a brown solid (50 mg).

NMR: d6-DMSO. Includes 5.35(2H,s)

The following compounds were prepared in an analogous manner from 4-hydroxy-benzo[a]phenazine-11-carboxylic acid using the appropriate alkylating reagent;

4-Prop-2-ynyloxy-benzo[a]phenazine-11-carboxylic acid (II.14) was prepared using propargyl bromide;

4-Isobutoxy-benzo[a]phenazine-11-carboxylic acid (II.15) was prepared using isobutyl bromide;

4-(4-Chloro-benzyloxy)-benzo[a]phenazine-11-carboxylic acid (II.16) was prepared using p-chlorobenzyl bromide;

4-(2-Methoxy-ethoxy)-benzo[a]phenazine-11-carboxylic acid (II.17) was prepared using 2-bromoethyl methyl ether;

4-Ethoxycarbonylmethoxy-benzo[a]phenazine-11-carboxylic acid (II.18) was prepared using ethyl bromoacetate. Sodium ethoxide in dry ethanol was used for this reaction;

4-[2-(tert-Butyl-dimethyl-silanyloxy)-ethoxy]-benzo[a] phenazine-11-carboxylic acid (II.19) was prepared using tert-butyl-(2-iodo-ethoxy)-dimethyl-silane. The tert-Butyl-(2-iodo-ethoxy)-dimethyl-silane was prepared using standard procedures from 2-iodo-ethanol.

Reference Example 1L

Benzo[a]phenazine-11-carboxylic acid (II.20)

A mixture of 1,2-naphthoquinone (commercially available, 2.0 g) and 2,3-diamino-benzoic acid, diacetate salt, (3.79 g) was heated to reflux in acetic acid (30 mL) for 2 hours. The reaction mixture was cooled and the solvent removed in vacuo to yield a gum. This was purified using flash chromatography to yield a 2:1 mixture of the desired title compound to the undesired benzo[a]phenazine-8-carboxylic acid (840 mg). The two isomers were separated after further modification (see Reference Example 3B below).

NMR d6-DMSO, includes 9.07–9.09(1H,m), 9.21–9.22 (1H,m). 2:1 ratio

Reference Example 1M

4-Methylsulfamoyl-benzo[a]phenazine-11-carboxylic acid (II.21) and 3-methylsulfamoyl-benzo[a]phenazine-11-carboxylic acid (II.22)

Benzo[a]phenazine-11-carboxylic acid methyl ester (IV.20, see Reference Example 3B, 220 mg) was heated under nitrogen chlorosulphonic acid (2 mL) for 6 hours. The reaction was then cooled, poured onto ice/water and the pale yellow solid collected by filtration to give approximately a 1:1 mixture of 4-chlorosulfonyl-benzo[a]phenazine-11-carboxylic acid and 3-chlorosulfonyl-benzo[a]phenazine-11-carboxylic acid (182 mg). NMR d6-DMSO, includes 9.41 (1H,s), 9.30(1H,d).

The mixture of 4-chlorosulfonyl-benzo[a]phenazine-11-carboxylic acid and 3-chlorosulfonyl-benzo[a]phenazine-11-carboxylic acid (182 mg) was dissolved in dichloromethane (5 mL). To this was added a 40% solution of methylamine in water (5 mL) and the reaction mixture was stirred vigorously for 4 hours. The reaction mixture was then poured onto dichloromethane, acidified (2N HCl), extracted into dichloromethane, dried (MgSO$_4$) and the solvent removed in vacuo to give a ~1:1 mixture of the title compounds (160 mg). The two isomers were separated after further chemical modification.

NMR (CDCl3+d4MeOH) includes 9.38(1H,s), 9.22(1H, d), 2.61 (3H,s), 2.55(3H,s).

4-Dimethylsulfamoyl-benzo[a]phenazine-11-carboxylic acid (II.23) and 3-dimethylsulfamoyl-benzo[a]phenazine-11-carboxylic acid (II.24) were prepared in an analogous manner by reaction of dimethylamine with the mixture of 4-chlorosulfonyl-benzo[a]phenazine-11-carboxylic acid and 3-chlorosulfonyl-benzo[a]phenazine-11-carboxylic acid. The two isomers were separated after further chemical modification. NMR (d6-DMSO) of mixture includes 9.06 (1H,d), 9.42(1H,s), 2.93(6H,s).

4-Sulfamoyl-benzo[a]phenazine-11-carboxylic acid (II.25) and 3-sulfamoyl-benzo[a]phenazine-11-carboxylic acid (II.26) were prepared in an analogous manner by reaction of ammonium hydroxide with the mixture of 4-chlorosulfonyl-benzo[a]phenazine-11-carboxylic acid and 3-chlorosulfonyl-benzo[a]phenazine-11-carboxylic acid. The two isomers were separated after further chemical modification. NMR (d6-DMSO) of mixture includes, 9.39 (1H,d), and 9.60(1H,s).

Reference Example 1N

4-Nitro-benzo[a]phenazine-11-carboxylic acid (II.27) and 3-nitro-benzo[a]phenazine-11-carboxylic acid (II.28)

Concentrated sulphuric acid (5 mL) and concentrated nitric acid (5 mL) were mixed together at 0° C. To this mixture was added benzo[a]phenazine-11-carboxylic acid (II.20) (100 mg) and the reaction mixture allowed to warm slowly to room temperature. After 24 hours the reaction mixture was poured onto water yielding a yellow precipitate. This was collected by filtration to yield a 4:1 mixture of 4-nitro-benzo[a]phenazine-11-carboxylic acid (II.27) and 3-nitro-benzo[a]phenazine-11-carboxylic acid (II.28). The two isomers were separated after further chemical modification.

NMR, d6-DMSO, includes 9.82(1H,d), 9.46(1H,d), 1:4 ratio MS MH@320

Reference Example 1O

4-Amino-benzo[a]phenazine-11-carboxylic acid (II.29) and 3-amino-benzo[a]phenazine-11-carboxylic acid (II.30)

To the 4:1 mixture of 4-nitro-benzo[a]phenazine-11-carboxylic acid (II.27) and 3-nitro-benzo[a]phenazine-11-carboxylic acid (II.28)(52 mg) in ethanol (5 mL) from Reference Example 1N was added ammonium chloride solution (3 mL) and indium (cat.) The reaction mixture was heated to reflux, then cooled and filtered through a bed of celite. The filtrate was diluted with water, extracted into dichloromethane, dried (MgSO$_4$) and the solvent removed in vacuo to yield the title compounds as a mixture (48 mg). Separated after further modification.

NMR, d6-DMSO, 6.95(1H,d), 7.55(1H,t), 7.75(2H,m), 8.05(2H,m), 8.20(1H,d), 8.65(1H,d)

Reference Example 1P

3-Bromo-4-hydroxy-benzo[a]phenazine-11-carboxylic acid (II.31)

A mixture of 4-hydroxy-benzo[a]phenazine-11-carboxylic acid (see Reference Example 1K, 102 mg) and bromine (0.04 mL) was stirred in chloroform (3 mL) at room temperature for 20 hours. The solvent was removed in vacuo and the residue was purified using flash chromatography (10% methanol in dichloromethane) to yield the title compound (24 mg) as a yellow-brown solid.

MS DCI/NH3, MH+ 369/371 (1:1) NMR (CDCl3), 7.94 (1H,d), 8.1–8.2(2H,m), 8.52–8.62(2H,m), 9.1(1H,d).

Reference Example 1Q

2-Nitro-benzo[a]phenazine-11-carboxylic acid (II.32)

7-Nitro-1-tetralone was prepared according to the literature (J. Am. Chem. Soc, 1994, 116, pp4852–4857). Treatment of 7-nitro-1-tetralone with selenium dioxide as described in Reference Example 1A yielded the corresponding 7-nitro-[1,2]naphthoquinone, which was coupled with 2,3-diamino-benzoic acid, diacetate salt, as described in Reference Example 1A to yield the title compound.

Reference Example 1R

2-Methoxy-benzo[a]phenazine-11-carboxylic acid (II.33)

8-Amino-naphthalen-2-ol was prepared from 8-amino-2-naphthalenesulphonic acid (commercially available) according to the literature (J. Org. Chem. 1949, p351). To a solution of 8-amino-naphthalen-2-ol (8.00 g) in dry N,N-dimethylformamide (80 mL) was added sodium hydride (60% dispersion in mineral oil, 3.2 g) carefully. After stirring for 4 hours the reaction mixture was cooled in an ice bath and methyl iodide (3.13 mL) was added dropwise. The reaction mixture was then stirred at room temperature for 3 days. Water (10 mL) was then added and the volatiles were removed in vacuo. The residue was dissolved in chloroform, washed with water, dried ($MgSO_4$) and the solvent removed in vacuo to yield a dark oil. This was purified using flash chromatography (chloroform) to yield 7-methoxy-naphthalen-1-ylamine as a dark brown liquid (2.92 g).

7-Methoxy-naphthalen-1-ylamine was treated with 2-bromo-3-nitro-benzoic acid according to the analogous procedure described by G. W. Rewcastle et al (J. Med. Chem. 1987, p843) to yield 2-(7-methoxy-naphthaten-1-ylamino)-3-nitro-benzoic acid. Reductive cyclisation using sodium borohydride (J. Med Chem. 1987, p843) yielded the desired title compound.

NMR, d6-DMSO, 14.44(1H,broad,s), 8.55(1H,d), 8.48 (1H,dd), 8.42(1H,dd), 8.23(1H,d), 8.10–8.04(2H,m), 7.86 (1H,d), 7.56(1H,dd), 4.02(3H,s). MH+ @1305

3-Methoxy-benzo[a]phenazine-11-carboxylic acid (II.34) was prepared in analogous manner starting with 5-amino-naphthalene-2-sulfonic acid (commercially available).

NMR, d6-DMSO, 14.60(1H,broad,s), 8.94(1H,d); 8.51 (2H,d), 8.23(1H,d), 8.10–7.96(2H,m), 7.67(1H,d), 7.55(1H, dd), 3.99(3H,s). MH+ @305

Reference Example 1S

9-Bromo-4-methoxy-benzo[a]phenazine-11-carboxylic acid (II.35)

A mixture of 4-methoxy-benzo[a]phenazine-11-carboxylic acid (II.1)(100 mg) and bromine (5 drops) in chloroform (7 mL) was stirred at room temperature for 3 days. The reaction mixture was reduced in vacuo and the desired product was isolated using flash chromatography (25 mg).

MS MH+ @383385 (1:1) NMR, $CDCl_3$, 14.47(1H,br,s), 8.86(1H,d), 8.33(1H,d), 7.95(1H,t), 7.78(1H,d), 6.97(1H,d), 6.12(1H,d), 5.75(1H,d), 3.94(3H,s)

Reference Example 1T

4,10-Dimethoxy-benzo[a]phenazine-11-carboxylic acid (II.36)

2-Amino-6-methoxy-3-nitro-benzoic acid methyl ester was prepared using a procedure analogous to that described in the literature (Kim et al, J. Med. Chem. 1993, p2335). Hydrolysis of the methyl ester was achieved using potassium hydroxide in refluxing ethanol for 2 hours to yield 2-amino-6-methoxy-3-nitro-benzoic acid. Hydrogenation of the nitro croup was performed in acetic acid/water over palladium on carbon catalyst on the Parr apparatus at 50 psi $H_2$ to yield 2,3-diamino-6-methoxy-benzoic acid. This was reacted with 5-methoxy-[1,2]naphthoquinone as described in Reference Example 1A to yield the desired title compound.

NMR, d6-DMSO, 4.05(3H,s), 4.10(3H,s), 7.45(1H,d), 7.78–7.82(1H,m), 7.92(1H,d), 8.03(1H,d),8.36–8.40(2H, m), 8.78(1H,d)

Reference Example 1U

4-Methoxy-8-methyl-benzo[a]phenazine-11-carboxylic acid (II.37)

2,3-Diamino-4-methylbenzoic acid was prepared from 4-methyl anthranilic acid according to the method described by Rewcastle et al (J. Med Chem. 1987, p843). This was reacted with 5-methoxy-[1,2]naphthoquinone as described in Reference Example 1A to yield the desired title compound.

NMR, d6-DMSO, 2.97(3H,s), 4.06(3H,s), 7.50(1H,d), 7.85–7.90(1H,m), 7.97(1H,d),8.02(1H,d), 8.45–8.50(2H,m), 8.57(1H,d).

Reference Example 1V

9-Chloro-4-methoxy-benzo[a]phenazine-11-carboxylic acid (II.38)

5-Chloro-3-nitroanthranilic acid was prepared according to the procedure described by Flippin et al (Biorg. Med. Chem. Letts 1996, p477). Hydrogenation of this material in ethyl acetate using palladium on carbon at 50 psi $H_2$ for 2 hours yielded 2,3-diamino-5-chloro-benzoic acid. This was reacted with 5-methoxy-[1,2]naphthoquinone as described in Reference Example 1A to yield the desired title compound.

NMR, d6-DMSO, 4.05(3H,s), 7.48(1H,d), 7.82–7.86(1H, m), 7.92(1H,d), 8.30(1H,d), 8.48(1H,d), 8.54(1H,d), 8.68 (1H,d), 14.1(1H,broad).

REFERENCE EXAMPLE 2

Preparation of Compounds of General Formula (III)

Reference Example 2A

4-Aza-DL-leucine methyl ester. Hydrochloride (III.1)

Methanol (150 mL) was saturated with anhydrous hydrogen chloride gas. To this was added 4-aza-DL-leucine (4.86 g)(commercially available) and the reaction mixture was stirred overnight at room temperature. The solvent was removed in vacuo to yield the title compound (quantitative yield).

Reference Example 2B

$N^1,N^1$-Dimethyl-butane-1,2-diamine (III.2)

Methyl N-(tert-butoxycarbonyl)-2-aminobutyrate was prepared as described in the literature (J. Med. Chem. 1989, p1886). Treatment of this compound with diisobutyl aluminium hydride in toluene at −78° C. for 1.5 hours yielded the corresponding aldehyde (prep see H. W. Scheeren et al, J. Org. Chem. 1990, p3998).

A mixture of the aldehyde (1.85 g), dimethylamine hydrochloride (1.61 g), sodium acetate (1.21 g) and sodium cyanoborohydride (0.83 g) in methanol was stirred at room temperature for 24 hours. The pH was adjusted to 6–7 using acetic acid and monitored during the reaction. The reaction mixture was then concentrated in vacuo, and the residue dissolved in ethyl acetate and washed with water. The organic layer was dried (MgSO4) and the solvent removed in vacuo to yield a colourless oil, which was purified using flash chromatography to yield the desired dimethylamine derivative as a pale oil (0.56 g). To this compound (260 mg) was added a 4.0M solution of HCl in dioxane (2 mL) carefully and the reaction mixture stirred for 90 minutes. The reaction mixture was then concentrated in vacuo to yield the desired title compound as an off-white solid (quantitative yield).

Reference Example 2C $3N^1,N^1$-Trimethyl-butane-1,2-diamine. Hydrochloride salt (III.3)

N-(tert-butoxycarbonyl)-DL-valine methyl ester was prepared from DL-valine using standard preparative techniques. This was converted into the desired title compound using an analogous procedure to that described in Reference Example 2B.

Enantiomerically pure $(R)-3N^1,N^1$-Trimethyl-butane-1,2-diamine. Hydrochloride salt (III.3.a) was prepared by using D-valine as the starting material.

Reference Example 2D $N^1,N^1$-Dimethyl-3-phenyl-propane-1,2-diamine. Hydrochloride Salt (III.4)

N-(tert-butoxycarbonyl)-DL-phenylalanine methyl ester was prepared from DL-phenylalanine using standard preparative techniques. This was converted into the desired title compound using an analogous procedure to that described in Reference Example 2B.

Reference Example 2E $(S)-N^1,N^1$-Dimethyl-propane-1,2-diamine. Hydrochloride salt (III.5)

2-(S)-[N-(tert-Butoxycarbonyl)amino]propanal was prepared from L-alanine according to the procedure described in the literature (Chakravarty et al, J. Med. Chem 1989, p1886). A mixture of the aldehyde (2.62 g), dimethylamine hydrochloride (2.47 g), sodium acetate (1.99 g) and sodium cyanoborohydride (1.43 g) in methanol (45 mL) was stirred at room temperature for 8 hours. The reaction mixture was dissolved in ethyl acetate, washed with water, dried (MgSO$_4$), and the solvent removed in vacuo to yield a viscous oil. This was dissolved in dichloromethane, extracted with citric acid, basified with sodium hydroxide, and re-extracted with ethyl acetate. The organic layer was reduced in vacuo to yield the dimethylamino derivative as a white solid (586 mg).

To this compound (366 mg) was added a 4.0M solution of hydrochloric acid in dioxane (5.5 mL) at room temperature. After stirring for 30 mins the volatiles were removed in vacuo to yield the desired title compound as a viscous oil (313 mg)

Reference Example 2F $(R)-N^1,N^1$-Dimethyl-propane-1,2-diamine. Hydrochloride salt (III.6)

2-(R)-[N-(tert-butoxycarbonyl)amino]propanal was prepared from D-alanine Me-ester hydrochloride according to the procedure described in the literature (Chakravarty et al, J. Med. Chem 1989, p1886).

A mixture of the aldehyde (16.21 g), dimethylamine hydrochloride (15.28 g), sodium acetate (1.53 g) and sodium cyanoborohydride (8.24 g) in methanol (250 mL) was stirred at room temperature for 18 hours maintaining pH at 6–7 with AcOH. The reaction mixture was dissolved in ethyl acetate, washed with water, dried (MgSO$_4$), and the solvent removed in vacuo to yield a viscous oil which was purified using flash chromatography to yield the dimethylamino derivative as a white solid (10.81 g).

To this compound (3.17 g) was added a 4.0 M solution of hydrochloric acid in dioxane (20 mL) at room temperature. After stirring for 1 hour the volatiles were removed in vacuo to yield the desired title compound as a viscous oil (2.79 g).

Reference Example 2G (S)-2-Amino-3-dimethylamino-propan-1-ol. Hydrochloride salt (III.7)

N-[(tert-Butoxy)carbonyl]-O-(tert-butyldimethylsilyl)-R-serine methyl ester was prepared according to the literature (H. W. Scheeren et al, J. Org. Chem. 1990, p3998) from D-serine methyl ester hydrochloride. Treatment of this compound with diisobutyl aluminium hydride in toluene at −70° C. for 2 hours yielded the correponding aldehyde (H. W. Scheeren et al, J. Org. Chem. 1990, p3998).

A mixture of the crude aldehyde (4.43 g), dimethylamine.hydrochloride (2.26 g), sodium cyanoborohydride (1.31 g) and sodium acetate (1.83 g) was stirred in methanol (55 mL) for 24 hours at room temperature. Aqueous work-up yielded the dimethylamine derivative. This was dissolved in dioxane and to this was added a 4.0 M solution of hydrochloric acid in dioxane and the mixture stirred for 20 minutes. Concentration of the mixture in vacuo yielded the crude desired title compound as a white solid.

Reference Example 2H

3(S)-Amino-4-dimethylamino-butan-2(S)-ol. Hydrochloride salt (III.8)

Hydrogen chloride gas was bubbled through a solution of D-threonine (20 g) in methanol (50 mL). The resulting solution was stirred for 5 hours at room temperature and then reduced in vacuo to yield D-threonine methyl ester hydrochloride as a white solid (quantitative yield). Treatment with di-tert-butyl dicarbonate in acetonitrile with triethylamine yielded N-(tert-butoxycarbonyl)-D-threonine methyl ester. Treatment of this compound with tert-butyldimethylsilyl chloride in dichloromethane with imidazole yielded the corresponding TBDMS protected alcohol.

Treatment of this compound with diisobutyl aluminium hydride in toluene at −78° C. for 4 hours yielded the corresponding aldehyde (prep see H. W. Scheeren et al, J. Org. Chem. 1990, p3998). Reductive amination was carried out as described in Reference Example 2G to yield the corresponding dimethylamino derivative. Deprotection using 4.0M HCl in dioxane as described in Reference Example 2 G yielded the title compound as a golden oil.

Reference Example 2I

3-Amino-4-dimethylamino-butan-1-ol. Hydrochloride salt (III.9)

DL-Homoserine was treated with hydrogen chloride gas in methanol to yield the corresponding lactone. Treatment with di-tert-butyl dicarbonate in acetonitrile with triethylamine yielded the N-tert-butoxycarbonyl protected derivative.

Treatment of this compound with diisobutyl aluminium hydride in toluene at −78° C. for 4 hours yielded the corresponding lactol (prep see H. W. Scheeren et al, J. Org. Chem. 1990, p3998).

Reductive amination was carried out as described in Reference Example 2G to yield the corresponding dimethylamino derivative, 3-[N-(tert-Butoxycarbonyl)amino]-4-dimethylamino-butan-1-ol. Deprotection using 4.0M HCl in dioxane as described in Reference Example 2G yielded the desired title compound.

Reference Example 2J

1-Methyl-3-(R)-aminopyrrolidine. Hydrochloride salt (III.10)

A solution of 3R-(−)-1-benzyl-3-aminopyrrolidine (commercially available, 847 mg) in tert-butanol (10 mL) and 1.0N sodium hydroxide solution (4.8 mL) was treated dropwise with a solution of di-tert-butyl dicarbonate (1.06 g) in tert-butanol (5 mL). After 1.5 hours tert-butanol was removed in vacuo and the residue dissolved in ethyl acetate, washed with water, dried (MgSO$_4$) and the solvent removed in vacuo to yield the desired 3N-tert-butoxycarbonyl protected derivative as a colourless gum (1.26 g).

A solution of the 3N-tert-butoxycarbonyl protected derivative (800 mg) in tetrahydrofuran was stirred over palladium hydroxide catalyst under an atmosphere of hydrogen for 24 hours. The reaction mixture was then filtered through celite and the solvent removed in vacuo to yield the desired 3N-tert-butoxycarbonyl-3-(R)-aminopyrrolidine (quantitative yield).

To a solution of N-tert-butoxycarbonyl-3-(R)-aminopyrrolidine (437 mg) in methanol (10 mL) was added 37% formaldehyde solution in H$_2$O (0.52 mL) and sodium borohydride (271 mg). The reaction mixture was stirred for 24 hours at room temperature and then reduced in vacuo. The residue was dissolved in chloroform, washed with brine and NaHCO$_3$ solution, dried (MgSO$_4$) and the solvent removed in vacuo to yield the desired 3N-tert-butoxycarbonyl-3'-(R)-amino-1-methylpyrrolidine as a gum (390 mg). Deprotection with 4.0M HCl solution in dioxane as described above yielded the desired title compound.

Reference Example 2K

N$^1$,N$^1$,N$^2$,N$^2$-Tetramethyl-propane-1,2,3-triamine trihydrochloride (III.11)

To ice cooled thionyl chloride (35 mL), 1,3-bis(dimethylamino)-propan-2-ol (4.91 g, 33.58 mmol, commercially available) was added dropwise over 45 mins with stirring. After the addition was complete the mixture was stirred for a further 4 h. Excess thionyl chloride was removed under reduced pressure to give 8.9 g of a cream solid of the product as the hydrochloride salt. The free base was obtained by treating a suspension of the hydrochloride salt in toluene (18 mL) with sodium hydroxide (2.4 eq) in water (14 mL) for 30 min. The organic layer was removed, dried over MgSO$_4$, filtered and the solvent removed in vacuo to yield 2-chloro-N,N,N$^1$,N$^1$-tetramethylpropane-1,3-diamine as a yellow liquid.

2-Chloro-N,N,N$^1$,N$^1$-tetramethylpropane-1,3-diamine (1.6 g, 9.71 mmol) as a solution in toluene (14 mL) was treated with potassium phthalimide (1.98 g, 10.68 mmol). The stirred mixture was heated at reflux for 18 h under an inert atmosphere, cooled to ambient temperature and the solvent removed under reduced pressure to yield a beige solid, recrystallisation from diethyl ether afforded a fawn solid (1.85 g). This solid (0.953, 3.46 mmol) as a solution in ethanol (10 mL) was treated with hydrazine hydrate (0.22 mL, 6.93 mmol) and the mixture stirred at ambient temperature for 18 h. The suspension was removed by filtration and the filtrate acidified with 2 mL of 2 M hydrochloric acid and the solvent removed in vacuo to give the product as a cream solid (795 mg). M.pt 126.5–128° C., MH$^+$ 432.

REFERENCE EXAMPLE 3

Preparation of Compounds of General Formula (IV)

Reference Example 3A

4-Methoxy-benzo[a]phenazine-11-carboxylic acid methyl ester (IV.1).

Acetyl chloride (4.6 mL) was added dropwise to a suspension of 4-methoxy-benzo[a]phenazine-11-carboxylic acid (II.1, see Reference Example 1A, 4.9 g) in methanol (50 mL). The mixture was heated to reflux for 4 hours. The volatiles were then removed in vacuo to yield the title compound as a dark solid (quantitative yield).

NMR, d6-DMSO, 8.76(1H,d), 8.41(2H,d), 8.26(1H,d), 8.00(1H,t), 7.90(1H,d), 7.78(1H,t), 7.43(1H,d), 4.08(3H,s), 4.03(3H,s).

Reference Example 3B

Benzo[a]phenazine-11-carboxylic acid methyl ester (IV.2)

The mixture of benzo[a]phenazine-11-carboxylic acid (II.20) and benzo[a]phenazine-8-carboxylic acid (885 mg), prepared as described in Reference Example 1L above, was heated to reflux in a mixture of methanol (40 mL) and acetyl chloride (920 µL) for 90 minutes. The reaction mixture was then cooled slowly to yield the title compound as a single isomer which was collected by filtration (377 mg).

NMR, d6-DMSO, 9.53–9.55(1H,m), 9.06(1H,d), 8.57(1H,d), 8.47(1H,d), 8.35(1H,d), 8.10–8.11(1H,m), 8.09–8.02(1H,m), 7.95–8.01(2H,m), 4.21(3H,s)

Reference Example 3C

4-Dimethylamino-benzo[a]phenazine-11-carboxylic acid methyl ester (IV.3) and 3-dimethylamino-benzo[a]phenazine-11-carboxylic acid methyl ester (IV.4)

To the 4:1 mixture of 4-amino-benzo[a]phenazine-11-carboxylic acid (II.29) and 3-amino-benzo[a]phenazine-11-carboxylic acid (II.30)(48 mg) in N,N-dimethylformamide (10 mL) from Reference Example 1N was added methyl iodide (0.5 mL) and diisopropylethylamine (2.0 mL). The reaction mixture was heated to 100° C. for 4 hours. The mixture was cooled, diluted with ethyl acetate, washed with water, dried (MgSO4) and the solvent removed in vacuo to yield the title compounds as a red solid (29 mg). Purified after further chemical modification.

Reference Example 3D

10-Fluoro-4-methoxy-benzo[a]phenazine-11-carboxylic acid methyl ester (IV.5)

Methyl 2-amino-6-fluoro-3-nitrobenzoate was prepared according to the literature (J. Med. Chem 1993, p2335). Hydrogenation over palladium on carbon in methanol yielded 2,3-diamino-6-fluoro-benzoic acid methyl ester. This compound was reacted with 5-methoxy-[1,2]naphthoquinone in cold ethanol acid with concentrated HCl to yield the desired title compound.

NMR, CDCl3, 4.08(3H,s), 4.20(3H,s), 7.20(1H,d), 7.65–7.75(2H,m), 7.92(1H,d), 8.35(1H,dd), 8.53(1H,d), 8.91(1H,d) MS m/e 337 (MH+, 100%)

Reference Example 3E

4-Methoxy-10-methylamino-benzo[a]phenazine-11-carboxylic acid methyl ester (IV.6)

A mixture of 10-fluoro-4-methoxy-benzo[a]phenazine-11-carboxylic acid methyl ester (IV.5) (100 mg) and 2.0M solution of methylamine in tetrahydrofuran was stirred at room temperature for 18 hours. The solvent was then removed in vacuo to yield the crude desired title compound as an orange solid.

Reference Example 3F

10-Amino-4-methoxy-benzo[a]phenazine-11-carboxylic acid methyl ester (IV.7)

A mixture of 10-fluoro-4-methoxy-benzo[a]phenazine-11-carboxylic acid methyl ester (IV.5) (466 mg) and sodium azide (900 mg) in N,N-dimethylformamide (10 mL) was heated at 90° C. for 18 hours. The reaction mixture was then cooled, diluted with water, and then sodium hydroxide solution was added resulting in a brown precipitate. This was collected by filtration and washed with water and ether to yield the desired title compound as a yellow solid (242 mg).

NMR, CDCl3, 4.08(3H,s), 4.20(3H,s), 7.25(1H,d), 7.70–7.72(2H,m), 7.90(1H,d), 8.36(1H,d), 8.52(1H,d), 8.85 (1H,d). MS DCI/NH3 m/z 334 (MH+, 100%)

EXAMPLE 1

Preparation of Compounds of General Formula (I)

Example 1A

4-Methoxy-benzo[a]phenazine-11-carboxylic acid (2-dimethylamino-ethyl)-amide

A mixture of 4-methoxy-benzo[a]phenazine-11-carboxylic acid (II.1) (129 mg) and 1,1'-carbonyldiimidazole (138 mg) was stirred in dry N,N-dimethylformamide (8 mL) at room temperature for 4 hours. To this mixture was added N,N-dimethylethylenediamine (commercially available)(0.5 mL) and the reaction mixture was stirred at room temperature for a further 30 minutes. The volatiles were then removed in vacuo. The residue was dissolved in dichloromethane, washed with water, dried (MgSO$_4$) and the solvent removed in vacuo to provide crude product. This was purified using flash chromatography (5% methanol in dichloromethane) to yield the title compound as a bright yellow solid (120 mg).

The following compounds of formula (I) were prepared in an analogous manner using the appropriate starting acid of formula (II) and amine of formula (III).

3-Methoxy-benzo[a]phenazine-11-carboxylic acid (2-dimethylamino-ethyl)-amide was prepared from 3-methoxy-benzo[a]phenazine-11-carboxylic acid (II.34) and N,N-dimethylethylenediamine;

2-Methoxy-benzo[a]phenazine-11-carboxylic acid (2-dimethylamino-ethyl)-amide was prepared from 2-methoxy-benzo[a]phenazine-11-carboxylic acid (II.33) and N,N-dimethylethylenediamine;

4-Nitro-benzo[a]phenazine-11-carboxylic acid (2-dimethylamino-ethyl)-amide was prepared from the mixture of 4-nitro-benzo[a]phenazine-11-carboxylic acid (II.27) and 3-nitro-benzo[a]phenazine-11-carboxylic acid (II.28), and N,N-dimethylethylenediamine and then purified using flash chromatography;

4-Benzyloxy-benzo[a]phenazine-11-carboxylic acid (2-dimethylamino-ethyl)-amide was prepared from 4-benzyloxy-benzo[a]phenazine-11-carboxylic acid (II.13) and N,N-dimethylethylenediamine;

4-Prop-2-ynyloxy-benzo[a]phenazine-11-carboxylic acid (2-dimethylamino-ethyl)-amide was prepared from 4-prop-2-ynyloxy-benzo[a]phenazine-11-carboxylic acid (II.14) and N,N-dimethylethylenediamine;

3,4-Dimethoxy-benzo[a]phenazine-11-carboxylic acid (2-dimethylamino-ethyl)-amide was prepared from 3,4-dimethoxy-benzo[a]phenazine-11-carboxylic acid (II.4) and N,N-dimethylethylenediamine;

4-Ethoxy-benzo[a]phenazine-11-carboxylic acid (2-dimethylamino-ethyl)-amide was prepared from 4-ethoxy-benzo[a]phenazine-11-carboxylic acid (II.11) and N,N-dimethylethylenediamine;

4-Isobutoxy-benzo[a]phenazine-11-carboxylic acid (2-dimethylamino-ethyl)-amide was prepared from 4-isobutoxy-benzo[a]phenazine-11-carboxylic acid (II.15) and N,N-dimethylethylenediamine;

4-(4-Chloro-benzyloxy)-benzo[a]phenazine-11-carboxylic acid (2-dimethylamino-ethyl)-amide was prepared from 4-(4-chloro-benzyloxy)-benzo[a]phenazine-11-carboxylic acid (II.16) and N,N-dimethylethylenediamine;

4-(2-Methoxy-ethoxy)-benzo[a]phenazine-11-carboxylic acid (2-dimethylamino-ethyl)-amide was prepared from 4-(2-methoxy-ethoxy)-benzo[a]phenazine-11-carboxylic acid (II.17) and N,N-dimethylethylenediamine;

[11-(2-Dimethylamino-ethylcarbamoyl)-benzo[a]phenazin-4-yloxy]-acetic acid ethyl ester was prepared from 4-ethoxycarbonylmethoxy-benzo[a]phenazine-11-carboxylic acid (II.18) and N,N-dimethylethylenediamine;

3-Bromo-4-hydroxy-benzo[a]phenazine-11-carboxylic acid (2-dimethylamino-ethyl)-amide was prepared from 3-bromo-4-hydroxy-benzo[a]phenazine-11-carboxylic acid (II.31) and N,N-dimethylethylenediamine;

4-[2-(tert-Butyl-dimethyl-silanyloxy)-ethoxy]-benzo[a] phenazine-11-carboxylic acid (2-dimethylamino-ethyl)-amide was prepared from 4-[2-(tert-butyl-dimethyl-silanyloxy)-ethoxy]-benzo[a]phenazine-11-carboxylic acid (II.19) and N,N-dimethylethylenediamine;

4-Methyl-benzo[a]phenazine-11-carboxylic acid (2-dimethylamino-ethyl)-amide was prepared from 4-methyl-benzo[a]phenazine-11-carboxylic acid (II.2) and N,N-dimethylethylenediamine;

4-Fluoro-benzo[a]phenazine-11-carboxylic acid (2-dimethylamino-ethyl)-amide was prepared from 4-fluoro-benzo[a]phenazine-11-carboxylic acid (II.3) and N,N-dimethylethylenediamine;

4-Methylsulfanyl-benzo[a]phenazine-11-carboxylic acid (2-dimethylamino-ethyl)-amide was prepared from 4-methylsulfanyl-benzo[a]phenazine-11-carboxylic acid (II.12) and N,N-dimethylethylenediamine;

4-Bromo-benzo[a]phenazine-11-carboxylic acid (2-dimethylamino-ethyl)-amide was prepared from 4-bromo-benzo[a]phenazine-11-carboxylic acid (II.5) and N,N-dimethylethylenediamine;

4-Cyano-benzo[a]phenazine-11-carboxylic acid (2-dimethylamino-ethyl)-amide was prepared from 4-cyano-benzo[a]phenazine-11-carboxylic acid (II.6) and N,N-dimethylethylenediamine;

3-Nitro-benzo[a]phenazine-11-carboxylic acid (2-dimethylamino-ethyl)-amide was prepared from the mixture of 4-nitro-benzo[a]phenazine-11-carboxylic acid (II.27) and 3-nitro-benzo[a]phenazine-11-carboxylic acid (II.28), and N,N-dimethylethylenediamine, and then purified using flash chromatography;

4-Methanesulfonyl-benzo[a]phenazine-11-carboxylic acid (2-dimethylamino-ethyl)-amide was prepared from 4-methanesulphonyl-benzo[a]phenazine-11-carboxylic acid (II.8) and N,N-dimethylethylenediamine;

4-Chloro-benzo[a]phenazine-11-carboxylic acid (2-dimethylamino-ethyl)-amide was prepared from 4-chloro-benzo[a]phenazine-11-carboxylic acid (II.7) and N,N-dimethylethylenediamine;

4-Azido-benzo[a]phenazine-11-carboxylic acid (2-dimethylamino-ethyl)-amide was prepared from 4-azido-benzo[a]phenazine-11-carboxylic acid (II.9) and N,N-dimethylethylenediamine; 11-(2-Dimethylamino-ethylcarbamoyl)-benzo[a]phenazine-4-carboxylic acid methyl ester was prepared from benzo[a]phenazine-4,11-dicarboxylic acid 4-methyl ester (II.10) and N,N-dimethylethylenediamine;

4-Methylsulfamoyl-benzo[a]phenazine-11-carboxylic acid (2-dimethylamino-ethyl)-amide; trifluoro-acetate was prepared from the mixture of 4-methylsulfamoyl-benzo[a]phenazine-11-carboxylic acid (II.21) and 3-methylsulfamoyl-benzo[a]phenazine-11-carboxylic acid (II.22), and N,N-dimethylethylenediamine. The two isomers were separated using preparative HPLC;

3-Methylsulfamoyl-benzo[a]phenazine-11-carboxylic acid (2-dimethylamino-ethyl)-amide; trifluoro-acetate was prepared from the mixture of 4-methylsulfamoyl-benzo[a]phenazine-11-carboxylic acid (II.21) and 3-methylsulfamoyl-benzo[a]phenazine-11-carboxylic acid (II.22), and N,N-dimethylethylenediamine. The two isomers were separated using preparative HPLC;

4-Dimethylsulfamoyl-benzo[a]phenazine-11-carboxylic acid (2-dimethylamino-ethyl)-amide was prepared from the mixture of 4-dimethylsulfamoyl-benzo[a]phenazine-11-carboxylic acid (II.23) and 3-dimethylsulfamoyl-benzo[a]phenazine-11-carboxylic acid (II.24), and N,N-dimethylethylenediamine. The two isomers were separated using flash chromatography;

3-Dimethylsulfamoyl-benzo[a]phenazine-11-carboxylic acid (2-dimethylamino-ethyl)-amide was prepared from the mixture of 4-dimethylsulfamoyl-benzo[a]phenazine-11-carboxylic acid (II.23) and 3-dimethylsulfamoyl-benzo[a]phenazine-11-carboxylic acid (II.24), and N,N-dimethylethylenediamine. The two isomers were separated using flash chromatography;

3-Sulfamoyl-benzo[a]phenazine-11-carboxylic acid (2-dimethylamino-ethyl)-amide was prepared from the mixture of 4-sulfamoyl-benzo[a]phenazine-11-carboxylic acid (II.25) and 3-sulfamoyl-benzo[a]phenazine-11-carboxylic acid (II.26), and N,N-dimethylethylenediamine. 3-Sulfamoyl-benzo[a]phenazine-11-carboxylic acid (2-dimethylamino-ethyl)-amide was purified using flash chromatography;

2-Nitro-benzo[a]phenazine-11-carboxylic acid (2-dimethylamino-ethyl)-amide was prepared from 2-nitro-benzo[a]phenazine-11-carboxylic acid (III.32) and N,N-dimethylethylenediamine;

9-Bromo-4-methoxy-benzo[a]phenazine-11-carboxylic acid (2-dimethylamino-ethyl)-amide was prepared from 9-bromo-4-methoxy-benzo[a]phenazine-11-carboxylic acid (II.35) and N,N-dimethylethylenediamine;

4-Nitro-benzo[a]phenazine-11-carboxylic acid (2-dimethylamino-1-methyl-ethyl)-amide was prepared from the mixture of 4-nitro-benzo[a]phenazine-11-carboxylic acid (II.27) and 3-nitro-benzo[a]phenazine-11-carboxylic acid (II.28), and 1-dimethylamino-2-propylamine, and then purified using flash chromatography;

3-Nitro-benzo[a]phenazine-11-carboxylic acid (2-dimethylamino-1-methyl-ethyl)-amide was prepared from the mixture of 4-nitro-benzo[a]phenazine-11-carboxylic acid (II.27) and 3-nitro-benzo[a]phenazine-11-carboxylic acid (II.28), and 1-dimethylamino-2-propylamine, and then purified using flash chromatography;

Example 1B

4-Methoxy-benzo[a]phenazine-11-carboxylic acid (2-dimethylamino-1-methyl-ethyl)-amide A mixture of 4-methoxy-benzo[a]phenazine-11-carboxylic acid methyl ester (IV.1) (350 mg) and 1-dimethylamino-2-propylamine (2 mL)(commercially available) was heated to 110° C. under $N_2$ for 4 hours. The reaction mixture was then cooled and the excess amine was removed in vacuo. The residue was then purified using flash chromatography (silica, ethyl acetate and then 25% methanol in ethyl acetate) to yield the title compound as a yellow solid (164 mg).

The following compounds of formula (I) were prepared in an analogous manner using the appropriate starting ester of formula (IV) and the appropriate amine of Formula (III):

4-Methoxy-benzo[a]phenazine-11-carboxylic acid (3-dimethylamino-propyl)-amide was prepared from 4-methoxy-benzo[a]phenazine-11-carboxylic acid methyl ester (IV.1) and 3-(dimethylamino) propylamine (commercially available);

4-Methoxy-benzo[a]phenazine-11-carboxylic acid (3-amino-2-hydroxy-propyl)-amide was prepared from 4-methoxy-benzo[a]phenazine-11-carboxylic acid methyl ester (IV.1) and 1,3-diamino-2-hydroxypropane (commercially available);

4-Methoxy-benzo[a]phenazine-11-carboxylic acid (2-dimethylamino-propyl)-amide was prepared from 4-methoxy-benzo[a]phenazine-11-carboxylic acid methyl ester (IV.1) and $N^2,N^2$-dimethyl-propane-1,2-diamine (commercially available);

4-Dimethylamino-benzo[a]phenazine-11-carboxylic acid (2-dimethylamino-ethyl)-amide was prepared from the mixture of 4-dimethylamino-benzo[a]phenazine-11-carboxylic acid methyl ester (IV.3) and 3-dimethylamino-benzo[a]phenazine-11-carboxylic acid methyl ester (IV.4), and N,N-dimethylethylenediamine, followed by flash chromatography purification to remove the minor isomer;

4-Methoxy-10-methylamino-benzo[a]phenazine-11-carboxylic acid (2-dimethylamino-ethyl)-amide was prepared from 4-methoxy-10-methylamino-benzo[a]phenazine-11-carboxylic acid methyl ester (IV.6) and N,N-dimethylethylenediamine;

10-Amino-4-methoxy-benzo[a]phenazine-11-carboxylic acid (2-dimethylamino-ethyl)-amide was prepared from 10-amino-4-methoxy-benzo[a]phenazine-11-carboxylic acid methyl ester (IV.7 and N,N-dimethylethylenediamine; and 4-Methoxy-benzo[a]phenazine-11-carboxylic acid (2-methylamino-ethyl)-amide was prepared from 4-methoxy-benzo[a]phenazine-11-carboxylic acid methyl ester (IV.1) and N-methylethylenediamine;

Example 1C

4-Methoxy-benzo[a]phenazine-11-carboxylic acid (2-dimethylamino-1,1-dimethyl-ethyl)-amide A mixture of 4-methoxy-benzo[a]phenazine-11-carboxylic acid (II.1) and thionyl chloride was heated to reflux for 6 minutes. Thionyl chloride was then removed in vacuo. The residue was dissolved in dry dichloromethane at 0° C. and 1-dimethylamino-2-methyl-2-aminopropane (commercially available) was added. After stirring for 2 hours the reaction mixture was dissolved in dichloromethane, washed with sodium bicarbonate solution, dried ($MgSO_4$) and the solvent removed in vacuo to provide crude product. This was purified using flash chromatography to yield the title compound.

The following compounds of formula (I) were prepared in an analogous manner using the appropriate starting acid of formula (II) and the appropriate amine of Formula (III)

3-Dimethylamino-2-[(4-methoxy-benzo[a]phenazine-11-carbonyl)-amino]-propionic acid methyl ester was prepared from 4-methoxy-benzo[a]phenazine-11-carboxylic acid (II.1) and 4-aza-DL-leucine methyl ester, hydrochloride (III.1) in the presence of pyridine. This was purified using preparative HPLC (isocratic 60% water/40% MeCN) to yield the trifluoroacetate salt of the desired compound;

4,10-Dimethoxy-benzo[a]phenazine-11-carboxylic acid (2-dimethylamino-ethyl)-amide was prepared from 4,10-dimethoxy-benzo[a]phenazine-11-carboxylic acid (II.36) and N,N-dimethylethylenediamine;

Lengthened reaction times (over 1 hour) with thionyl chloride results in chlorination of the phenazine nucleus. Hence 1-Chloro-4,10-dimethoxy-benzo[a]phenazine-11-carboxylic acid (2-dimethylamino-ethyl)-amide was prepared from 4,10-dimethoxy-benzo[a]phenazine-11-carboxylic acid (II.36) and N,N-dimethylethylenediamine;

4-Methoxy-8-methyl-benzo[a]phenazine-11-carboxylic acid (2-dimethylamino-ethyl)-amide was prepared from 4-methoxy-8-methyl-benzo[a]phenazine-11-carboxylic acid (II.37) and N,N-dimethylethylenediamine;

9-Chloro-4-methoxy-benzo[a]phenazine-11-carboxylic acid (2-dimethylamino-ethyl)-amide was prepared from 9-chloro-4-methoxy-benzo[a]phenazine-11-carboxylic acid (II.38) and N,N-dimethylethylenediamine;

4,10-Dimethoxy-benzo[a]phenazine-11-carboxylic acid (2-dimethylamino-1-methyl-ethyl)-amide was prepared from 4,10-dimethoxy-benzo[a]phenazine-11-carboxylic acid (II.36) and 1-dimethylamino-2-propylamine (commercially available);

4-Methoxy-benzo[a]phenazine-11-carboxylic acid (1-dimethylaminomethyl-propyl)-amide was prepared from 4-methoxy-benzo[a]phenazine-11-carboxylic acid (II.1) and $N^1,N^1$-dimethyl-butane-1,2-diamine.hydrochloride (III.2) in the presence of triethylamine;

4-Methoxy-benzo[a]phenazine-11-carboxylic acid (1-dimethylaminomethyl-2-methyl-propyl)-amide was prepared from 4-methoxy-benzo[a]phenazine-11-carboxylic acid (II.1) and $3N^1,N^1$-trimethyl-butane-1,2-diamine. Hydrochloride salt (III.3) in the presence of triethylamine;

4-Methoxy-benzo[a]phenazine-11-carboxylic acid (1-dimethylaminomethyl-2-phenyl-ethyl)-amide was prepared from 4-methoxy-benzo[a]phenazine-11-carboxylic acid (II.0.1) and $N^1,N^1$-dimethyl-3-phenyl-propane-1,2-diamine. Hydrochloride salt (III.4) in the presence of triethylamine;

4-Methoxy-benzo[a]phenazine-11-carboxylic acid (2-dimethylamino-1-(S)-methyl-ethyl)-amide was prepared from 4-methoxy-benzo[a]phenazine-11-carboxylic acid (II.1) and (S)-$N^1,N^1$-dimethyl-propane-1,2-diamine. Hydrochloride salt (III.5) in the presence of triethylamine;

4-Methoxy-benzo[a]phenazine-11-carboxylic acid (2-dimethylamino-1(R)-methyl-ethyl)-amide was prepared from 4-methoxy-benzo[a]phenazine-11-carboxylic acid (II.1) and (R)-$N^1,N^1$-dimethyl-propane-1,2-diamine. Hydrochloride salt (III.6) in the presence of triethylamine;

4-Methoxy-benzo[a]phenazine-11-carboxylic acid (2-dimethylamino-1(S)-hydroxymethyl-ethyl)-amide was prepared from 4-methoxy-benzo[a]phenazine-11-carboxylic acid (II.1) and (S)-2-Amino-3-dimethylamino-propan-1-ol. Hydrochloride salt (III.7) in the presence of triethylamine;

4-Methoxy-benzo[a]phenazine-11-carboxylic acid (1(S)-dimethylaminomethyl-2(S)-hydroxy-propyl)-amide was prepared from 4-methoxy-benzo[a]phenazine-11-carboxylic acid (II.1) and 3(S)-Amino-4-dimethylamino-butan-2(S)-ol. Hydrochloride salt (III.8) in the presence of triethylamine;

4-Methoxy-benzo[a]phenazine-11-carboxylic acid [1-dimethylamino-1-(2-hydroxyethyl)]-ethylamide was prepared from 4-methoxy-benzo[a]phenazine-11-carboxylic acid (II.1) and 3-Amino-4-dimethylamino-butan-1-ol. Hydrochloride salt (III.9) in the presence of triethylamine;

4-Methoxy-benzo[a]phenazine-11-carboxylic acid (2-piperidin-1-yl-ethyl)-amide was prepared from 4-methoxy-benzo[a]phenazine-11-carboxylic acid (II.1) and 1-(2-aminoethyl)piperidine (commercially available);

4-Methoxy-benzo[a]phenazine-11-carboxylic acid (2-morpholin-4-yl-ethyl)-amide was prepared from 4-methoxy-benzo[a]phenazine-11-carboxylic acid (II.1) and 4-(2-aminoethyl)morpholine (commercially available);

4-Methoxy-benzo[a]phenazine-11-carboxylic acid (2-pyrrolidin-1-yl-ethyl)-amide was prepared from 4-methoxy-benzo[a]phenazine-11-carboxylic acid (II.1) and 1-(aminoethyl)pyrrolidine (commercially available);

4-Methoxy-benzo[a]phenazine-11-carboxylic acid (2-diethylamino-ethyl)-amide was prepared from 4-methoxy-benzo[a]phenazine-11-carboxylic acid (II.1) and N,N-diethylethylenediamine (commercially available);

4-Methoxy-benzo[a]phenazine-11-carboxylic acid {2-[bis-hydroxy-ethyl)-amino]-ethyl}-amide was prepared from 4-methoxy-benzo[a]phenazine-11-carboxylic acid (II.1) and N,N-bis(2-hydroxyethyl)ethylenediamine (commercially available);

4,10-Dimethoxy-benzo[a]phenazine-11-carboxylic acid (2-dimethylamino-1(S)-hydroxymethyl-ethyl)-amide was prepared from 4,10-dimethoxy-benzo[a]phenazine-11-carboxylic acid (II.36) and (S)-2-amino-3-dimethylamino-propan-1-ol. Hydrochloride salt (III.7) in the presence of aqueous sodium carbonate;

4-Methoxy-benzo[a]phenazine-11-carboxylic acid (1-methyl-pyrrolidin-3-(R)-yl)-amide was prepared from 4-methoxy-benzo[a]phenazine-11-carboxylic acid (II.1) and 1-methyl-3-(R)-aminopyrrolidine. Hydrochloride salt (III.10) in the presence of triethylamine;

(R)-4-Methoxy-benzo[a]phenazine-11-carboxylic acid (1-dimethylaminomethyl-2-methyl-propyl)-amide was prepared from 4-methoxy-benzo[a]phenazine-11-carboxylic acid (II.1) and (R)-3$N^1,N^1$-trimethyl-butane-1,2-diamine. Hydrochloride salt (III.3.a) in the presence of triethylamine;

trihydrochloride (III.11) in the presence of triethylamine;

4-Methoxy-benzo[a]phenazine-11-carboxylic acid (2,3-bis-dimethylamino-propyl)amide was prepared from 4-methoxy-benzo[a]phenazine-11-carboxylic acid (II.1) and $N^1,N^1,N^2,N^2$-tetramethyl-propane-1,2,3-triamine.

EXAMPLE 2

Interconversion of Compounds of Formula (I)

Compounds of Formula (I) prepared as described in Example 1 were converted into other compounds of Formula (I) as described below.

Example 2i

4-Hydroxy-benzo[a]phenazine-11-carboxylic acid (2-dimethylamino-ethyl)-amide: Hydrobromide Salt To a solution of 4-methoxy-benzo[a]phenazine-11-carboxylic acid (2-dimethylamino-ethyl)-amide (I.1) (727 mg) in dry dichloromethane (15 mL) cooled to −5° C. was added a 1.0M solution of boron tribromide in dichloromethane (13.6 mL). After stirring for 4 hours the reaction mixture was poured onto ice/water yielding a precipitate which was collected by filtration. This was triturated from a hot methanol/ethyl acetate mixture to yield the title compound as a beige solid (505 mg).

Example 2ii

3-Hydroxy-benzo[a]phenazine-11-carboxylic acid (2-dimethylamino-ethyl)-amide

To a solution of 3-methoxy-benzo[a]phenazine-11-carboxylic acid (2-dimethylamino-ethyl)-amide (170 mg) in dry N,N-dimethylformamide (3 mL) was added sodium thioethoxide (380 mg). The reaction mixture was then heated to reflux under argon for 3 hours. The reaction mixture was cooled, acidified (dilute HCl) and volatiles removed in vacuo. The residue was purified using column chromatography (20% methanol in dichloromethane) to yield the title compound as a red solid (142 mg).

2-Hydroxy-benzo[a]phenazine-11-carboxylic acid (2-dimethylamino-ethyl)-amide was prepared in an analogous manner from 2-methoxy-benzo[a]phenazine-11-carboxylic acid (2-dimethylamino-ethyl)-amide.

Example 2iii

4-Cyanomethoxy-benzo[a]phenazine-11-carboxylic acid (2-dimethylamino-ethyl)-amide To a suspension of 4-hydroxy-benzo[a]phenazine-11-carboxylic acid (2-dimethylamino-ethyl)-amide: hydrobromide salt (230 mg) in dry N,N-dimethylformamide (3 mL) was added potassium tert-butoxide (175 mg) and then bromoacetonitrile (47 µL). The reaction mixture was heated to 100° C. for 1 hour. The reaction mixture was then cooled, diluted with ethyl acetate, washed with sodium carbonate solution and brine, dried (MgSO$_4$) and the solvent removed in vacuo to provide crude product. This was purified using flash chromatography (silica, 25% MeOH in ethyl acetate) to yield the title compound as a yellow solid (74 mg).

The following compounds of formula (I) were prepared in an analogous manner using 4-hydroxy-benzo[a]phenazine-11-carboxylic acid (2-dimethylamino-ethyl)-amide:hydrobromide salt and the appropriate alkylating reagent;

4-(Pyrimidin-2-yloxy)-benzo[a]phenazine-11-carboxylic acid (2-dimethylamino-ethyl)-amide was prepared using 2-bromopyridine;

4-(2-Morpholin-4-yl-ethoxy)-benzo[a]phenazine-11-carboxylic acid (2-dimethylamino-ethyl)-amide was prepared using N-(2-chloroethyl)morpholine hydrochloride;

4-(3-Cyano-propoxy)-benzo[a]phenazine-11-carboxylic acid (2-dimethylamino-ethyl)-amide was prepared using 4-bromobutyronitrile;

4-(3-Dimethylamino-propoxy)-benzo[a]phenazine-11-carboxylic acid (2-dimethylamino-ethyl)-amide was prepared using 3-dimethylaminopropyl chloride hydrochloride;

4-Carbamoylmethoxy-benzo[a]phenazine-11-carboxylic acid (2-dimethylamino-ethyl)-amide was prepared using 2-bromoacetamide;

4-(2-Oxo-propoxy)-benzo[a]phenazine-11-carboxylic acid (2-dimethylamino-ethyl)-amide was prepared using chloroacetone; and

[11-(2-Dimethylamino-ethylcarbamoyl)-benzo[a]phenazin-4-yloxy]-acetic acid tertbutyl ester was prepared using tert-butyl bromoacetate.

Example 2iv

Ethyl-carbamic acid 11-(2-dimethylamino-ethylcarbamoyl)-benzo[a]phenazin-4-yl ester A mixture of 4-hydroxy-benzo[a]phenazine-11-carboxylic acid (2-dimethylamino-ethyl)-amide: hydrobromide salt (540 mg), triethylamine (0.51 mL) and ethyl isocyanate (0.29 mL) was stirred in dry N,N-dimethylformamide (3 mL). The product slowly precipitated from the reaction mixture and was collected by filtration and washed with ether to yield the title compound as a yellow solid (210 mg).

Example 2v

Acetic acid 11-(2-dimethylamino-ethylcarbamoyl)-benzo[a]phenazin-4-yl ester

A mixture of 4-hydroxy-benzo[a]phenazine-11-carboxylic acid (2-dimethylamino-ethyl)-amide: hydrobromide salt (45 mg), triethylamine (71 µL) and acetyl chloride (20 µL) in dichloromethane (1.4 mL) was stirred at room temperature for 2 hours. All volatiles were removed in vacuo and the residue was purified using column chromatography (10% methanol in dichloromethane) to yield the title compound as a yellow solid (27 mg).

Example 2vi

[11-(2-dimethylamino-ethylcarbamoyl)-benzo[a]phenazin-4-yloxy]-acetic acid trifluoracetate salt To a solution of [11-(2-dimethylamino-ethylcarbamoyl)-benzo[a]phenazin-4-yloxy]-acetic acid tert-butyl ester (18 mg) in dry dichloromethane (1 mL) was added trifluoroacetic acid (1 mL). After stirring for 4 hours the solvent was removed in vacuo to yield crude product. This was triturated with ether to yield the title compound as a yellow solid (10 mg).

Example 2vii

Benzo[a]phenazine-4,11-dicarboxylic acid 4-amide 11-[(2-dimethylamine-ethyl)-amide]; triflouroacetic acid salt 11-(2-Dimethylamino-ethylcarbamoyl)-benzo[a]phenazine-4-carboxylic acid methyl ester (200 mg) was sonicated in methanol (20 mL) to give a fine suspension. To this was added sodium cyanide (22 mg). The mixture was then sparged with anhydrous ammonia for 15 mins. The reaction mixture was stirred at room temperature for 10 days and on each day the mixture was sparged with ammonia. After 10 days the volatiles were removed in vacuo and the residue was purified using flash chromatography to yield crude product. This was further purified using preparative HPLC (isocratic; 80:20H$_2$O/acetonitrile) to yield the title compound as a yellow solid (10 mg).

Example 2viii 11-(2-Dimethylamino-ethylcarbamoyl)-benzo[a]phenazine-4-carboxylic acid, trifluoroacetate salt 11-(2-Dimethylamino-ethylcarbamoyl)-benzo[a]phenazine-4-carboxylic acid methyl ester (200 mg) was sonicated in a mixture of methanol (4 mL) and ammonium hydroxide (20 mL). The suspension was then heated to 50° C. for 92 hours. All volatiles were then removed in vacuo to yield crude product, which was purified using preparative HPLC to yield the title compound (20 mg).

Example 2ix

4-Hydroxymethyl-benzo[a]phenazine-11-carboxylic acid (2-dimethylamino-ethyl)-amide To a solution of 11-(2-dimethylamino-ethylcarbamoyl)-benzo[a]phenazine-4-carboxylic acid methyl ester (317 mg) in tetrahydrofuran (18 mL) and 2-propanol (10 mL) at 0° C. was added lithium borohydride (2.0M solution in tetrahydrofuran, 1.97 mL) The reaction mixture was stirred at room temperature overnight, and then quenched with ammonium chloride solution. The reaction mixture was extracted with ethyl acetate, dried (MgSO$_4$) and concentrated in vacuo. The residue was purified using flash chromatography (10% MeOH in dichloromethane) to yield the title compound as a yellow solid (98 mg).

Example 2x 4-(N-Hydroxycarbamimidoyl)-benzo[a]phenazine-11-carboxylic acid (2-dimethylamino-ethyl)-amide A mixture of 4-cyano-benzo[a]phenazine-11-carboxylic acid (2-dimethylamino-ethyl)-amide (20 mg), potassium carbonate (37 mg) and hydroxylamine hydrochloride (19 mg) was heated to reflux in ethanol (5 mL) for 18 hours. The reaction mixture was filtered, and the filtrate was collected and the solvent removed in vacuo to yield the title compound (20 mg).

Example 2xi

4-Dimethylaminomethyl-3-hydroxy-benzo[a]phenazine-11-carboxylic acid (2-dimethylamino-ethyl)-amide 3-Hydroxy-benzo[a]phenazine-11-carboxylic acid (2-dimethylamino-ethyl)-amide (26 mg) was sonicated in acetic acid (2 mL) to give a fine suspension. To this was added a 40% solution of dimethylamine in water (3 mL) and a 37% solution of formaldehyde in water (3 mL). The reaction mixture was left stirring for 2 days. The volatiles were then removed in vacuo to yield the title compound (29 mg).

3-Dimethylaminomethyl-4-hydroxy-benzo[a]phenazine-11-carboxylic acid (2-dimethylamino-ethyl)-amide was prepared in an analogous manner from 4-hydroxy-benzo[a]phenazine-11-carboxylic acid (2-dimethylamino-ethyl)-amide.

Example 2xii 4-(2-Hydroxy-ethoxy)-benzo[a]phenazine-11-carboxylic acid (2-dimethylamino-ethyl)-amide To a solution of 4-[2-(tert-butyl-dimethyl-silanyloxy)-ethoxy]-benzo[a]phenazine-11-carboxylic acid (2-dimethylamino-ethyl)-amide (125 mg) in tetrahydrofuran (5 mL) was added a 1.0M solution of tetrabutyl ammonium fluoride (1.2 mL). After stirring for 1.5 hours the reaction mixture was diluted with ethyl acetate, washed with water, dried (MgSO$_4$) and the solvent removed in vacuo to yield crude product which was purified using flash chromatography to yield the title compound as an orange solid (24 mg).

Example 2xiii

4-Amino-benzo[a]phenazine-11-carboxylic acid (2-dimethylamino-ethyl)-amide

A mixture of 4-nitro-benzo[a]phenazine-11-carboxylic acid (2-dimethylamino-ethyl)-amide (176 mg), indium (154 mg) and saturated ammonium chloride solution (5 mL) in ethanol (20 mL) was heated to reflux for 3 hours. The reaction mixture was cooled, quenched with water and then filtered through celite. The filtrate was concentrated in vacuo, and the residue was treated with sodium bicarbonate solution, extracted into chloroform, dried (MgSO$_4$) and the solvent removed in vacuo to yield the title compound as a red solid (163 mg) 3-Amino-benzo[a]phenazine-11-carboxylic acid (2-dimethylamino-ethyl)-amide was prepared in an analogous manner from 3-nitro-benzo[a]phenazine-11-carboxylic acid (2-dimethylamino-ethyl)-amide.

Example 2xiv

4-Acetylamino-benzo[a]phenazine-11-carboxylic acid (2-dimethylamino-ethyl)-amide

To a solution of 4-amino-benzo[a]phenazine-11-carboxylic acid (2-dimethylamino-ethyl)-amide (20 mg) in tetrahydrofuran (5 mL) was added pyridine (0.1 mL) and acetyl chloride (20 µL). After stirring for 1 hour the reaction mixture was extracted into ethyl acetate, washed with sodium bicarbonate solution, dried (MgSO$_4$) and the solvent removed in vacuo The residue was triturated with ether to yield the title compound as a yellow solid (10 mg).

3-Acetylamino-benzo[a]phenazine-11-carboxylic acid (2-dimethylamino-ethyl)-amide was prepared in an analogous manner from 3-amino-benzo[a]phenazine-11-carboxylic acid (2-dimethylamino-ethyl)-amide and acetyl chloride;

4-Methanesulfonylamino-benzo[a]phenazine-11-carboxylic acid (2-dimethylamino-ethyl)-amide was prepared in an analogous manner from 4-amino-benzo[a]phenazine-11-carboxylic acid (2-dimethylamino-ethyl)-amide and methanesulphonyl chloride;

3-Methanesulfonylamino-benzo[a]phenazine-11-carboxylic acid (2-dimethylamino-ethyl)-amide was prepared in an analogous manner from 3-amino-benzo[a]phenazine-11-carboxylic acid (2-dimethylamino-ethyl)-amide and methanesulphonyl chloride;

4-Bis-(Methanesulfonylamino)-benzo[a]phenazine-11-carboxylic acid (2-dimethylamino-ethyl)-amide was prepared in a similar manner from 4-amino-benzo[a]phenazine-11-carboxylic acid (2-dimethylamino-ethyl)-amide using excess methanesulphonyl chloride, and triethylamine as base.

Example 2xv

4-(Cyanomethyl-amino)-benzo[a]phenazine-11-carboxylic acid (2-dimethylamino-ethyl)-amide

To a solution of 4-amino-benzo[a]phenazine-11-carboxylic acid (2-dimethylamino-ethyl)-amide (69 mg) in methanol (10 mL) was added formaldehyde (37% solution, 11.0 mL), potassium cyanide (102 mg) and 2N HCl (1.0 mL). The reaction mixture was heated to 50° C. for 3 hours. The reaction mixture was then cooled, diluted with water and sodium bicarbonate solution, extracted into dichloromethane, dried (MgSO$_4$) and the solvent removed in vacuo to yield crude product. This was purified using flash chromatography (10% methanol in dichloromethane) to yield the title compound as a violet coloured solid (13 mg).

Example 2xvi

3-Dimethylamino-2-[(4-methoxy-benzo[a]phenazine-11-carbonyl)-amino]-propionic acid; hydrochloride

A mixture of 3-dimethylamino-2-[(4-methoxy-benzo[a]phenazine-11-carbonyl)-amino]-propionic acid methyl ester (150 mg) and 1M HCl (50 mL) was heated to reflux for 1 hour. After cooling, all volatiles were removed in vacuo to yield the title compound as a red solid (quantitative yield).

Example 2xvii

4,10-Dihydroxy-benzo[a]phenazine-11-carboxylic acid (2-dimethylamino-ethyl)-amide

To a cold solution of 4,10-dimethoxy-benzo[a]phenazine-11-carboxylic acid (2-dimethylamino-ethyl)-amide (96 mg) in dichloromethane (2 mL) was added a 11.0M solution of boron tribromide in dichloromethane (2.14 mL, 9 equivalents). The reaction mixture was stirred for 16 hours and then ice was added with sodium carbonate and sodium chloride. The organics were extracted into dichloromethane, dried (MgSO$_4$), and the solvent removed in vacuo to yield an orange compound which was recrystallised from dichloromethane/methanol/hexane to yield the title compound (6 mg).

Example 2xviii

10-Hydroxy-4-methoxy-benzo[a]phenazine-11-carboxylic acid (2-dimethylamino-ethyl)-amide

To a cold solution of 4,10-dimethoxy-benzo[a]phenazine-11-carboxylic acid (2-dimethylamino-ethyl)-amide (300 mg) in dichloromethane (25 mL) was added a 1.0M solution of boron tribromide in dichloromethane (1.63 mL, 2.2 equivalents). The reaction mixture was stirred for 6 hours and then ice was added with sodium carbonate and sodium chloride. The organics were extracted into dichloromethane, dried (MgSO$_4$), and the solvent removed in vacuo to yield a yellow solid which was purified using flash chromatography to yield the title compound (61 mg)

10-Hydroxy-4-methoxy-benzo[a]phenazine-11-carboxylic acid (2-dimethylamino-1(R)-methyl-ethyl)-amide was prepared in an analogous manner from 4,10-dimethoxy-benzo[a]phenazine-11-carboxylic acid (2-dimethylamino-1(R)-methyl-ethyl)-amide; and 10-Hydroxy-4-methoxy-benzo[a]phenazine-11-carboxylic acid (2-dimethylamino-1(S)-hydroxymethyl-ethyl)-amide was prepared in an analogous manner from 4,10-dimethoxy-benzo[a]phenazine-11-carboxylic acid (2-dimethylamino-1(S)-hydroxymethyl-ethyl)-amide.

Example 2xix

4-Methoxy-9-methylsulfanyl-benzo[a]phenazine-11-carboxylic acid (2-dimethylamino-ethyl)-amide

A mixture of 9-chloro-4-methoxy-benzo[a]phenazine-11-carboxylic acid (2-dimethylamino-ethyl)-amide (85 mg) and sodium thiomethoxide (43 mg) in N,N-dimethylformamide (1 mL) was heated to 120° C. for 6 hours and 60° C. for 16 hours. The reaction mixture was then cooled, diluted with ethyl acetate, washed with water, dried (MgSO$_4$) and the solvent removed in vacuo to yield a yellow solid which was purified using flash chromatography to yield the desired title compound (37 mg).

Example 2xx

4,9-Dimethoxy-benzo[a]phenazine-11-carboxylic acid (2-dimethylamino-ethyl)-amide

A mixture of 9-chloro-4-methoxy-benzo[a]phenazine-11-carboxylic acid (2-dimethylamino-ethyl)-amide (85 mg) and a 25% solution of sodium methoxide in methanol (4 mL) was heated to reflux for 6 hours. The reaction mixture was then cooled, diluted with ethyl acetate, washed with water, dried (MgSO$_4$) and the solvent removed in vacuo to yield a yellow solid which was purified using flash chromatography to yield the desired title compound (42 mg).

Example 2xxi

4-Methoxy-benzo[a]phenazine-11-carboxylic acid (2-dimethylamino-1-hydroxymethyl-ethyl)-amide A mixture of 3-dimethylamino-2-[(4-methoxy-benzo[a]phenazine-11-carbonyl)-amino]-propionic acid methyl ester (335 mg) and lithium borohydride (72 mg) in tetrahydrofuran (10 mL) and isopropanol (10 mL) was stirred at room temperature for 18 hours. Another 5 equivalents of lithium borohydride were added and the mixture stirred for another 18 hours. The reaction was quenched with ammonium chloride solution and extracted with ethyl acetate, dried (MgSO$_4$) and the solvent removed in vacuo to yield a brown gum. Purification using flash chromatography and trituration with ether yielded the desired title compound as an orange powder.

EXAMPLE 3

Biological Testing of Compounds of Formula (I)

The cytotoxicity of compounds of formula (I) was measured using the H69 parental (H69/P) human small cell lung carcinoma cell line and the drug resistant human small cell lung carcinoma cell line H69/LX4 which overexpresses P-glycoprotein (Pgp). The cytotoxicity, as measured by the IC$_{50}$ (concentration required to give 50% cell kill) in the H69/LX4 cell line divided by the cytotoxicity in the H69/P cell line gives an indication of the degree to which a compound is affected by Pgp-dependent MDR and is termed the resistance factor (Rf) of the compound.

H69/P and H69/LX4 cells were pipetted into 96-well tissue culture plates and then allowed to incubate at 37° C. for 4 h. A range of concentrations from 0.01 nM to 5 μM of compounds of formula (I) or the standards TAS-103, Doxorubicin and Topotecan were then added. The plates were incubated for 5–6 days before adding AlamarBlue to each well and returning the plates to the incubator for 5–8 h to allow colour development. The cell numbers in the plates at the end of this period were directly proportional to the absorbance measured at a wavelength of 570 nm (reference wavelength 600 nm).

The compounds of formula (I) were active in the range 5 nM to 5 μM. Specific results for selected compounds are listed in table 1.

TABLE 1

| Compound | H69/P IC$_{50}$(nM) | H69/LX4 IC$_{50}$(nM) | Rf |
|---|---|---|---|
| TAS-103 | 21 | 22 | 1.1 |
| Doxorubicin | 27.3 | 3700 | 135 |
| Topotecan | 15.9 | 61.5 | 3.9 |
| 4 | 35 | 48 | 1.4 |
| 3 | 35 | 49 | 1.4 |
| 11 | 28 | 24 | 0.9 |
| 94 | 19 | 25 | 1.3 |
| 68 | 19 | 25 | 1.3 |
| 75 | 23 | 28 | 1.2 |
| 81 | 20 | 25 | 1.2 |
| 78 | 24 | 31 | 1.3 |
| 98 | 21 | 20 | 1 |
| 84 | 19 | 19 | 1 |

The cytotoxicity of the compounds described herein was also measured using the COR-L23 parental (COR-L23/P) human non-small cell lung carcinoma cell line and also the drug resistant human non-small cell lung carcinoma cell line COR-L23/R which overexpresses multidrug resistance associated protein (MRP). The cytotoxicity, as measured by the IC$_{50}$ (concentration required to give 50% cell kill) in the L23/R cell line divided by the cytotoxicity in the L23/P cell line gives an indication of the degree to which a compound may be affected by MRP-dependant MDR and is termed the resistance factor (Rf) of the compound.

L23/P and L23/R cells were pipetted into 96-well tissue culture plates and then allowed to incubate at 37° C. for 4 h. A range of concentrations from 0.01 nM to 5 μM of compounds of formula (I) or the standards TAS-103, Doxorubicin and Topotecan were then added. The plates were incubated for 5–6 days before proliferation was assessed using the sulphurhodamine B (SRB) assay as described by Skehan et al, J Natl Cancer Inst 1990, 82, pp 1107–1112.

Compounds were active in the range 1 nM to 5 μM. Specific examples are listed in Table 2.

TABLE 2

| Compound | L23/P IC$_{50}$(nM) | L23/R IC$_{50}$(nM) | Rf |
|---|---|---|---|
| TAS-103 | 16.3 | 22 | 1.3 |
| Doxorubicin | 20.3 | 326.8 | 16.1 |
| Topotecan | 13.6 | 20.8 | 1.5 |
| 4 | 14.7 | 16.8 | 1.1 |
| 3 | 14.4 | 19.9 | 1.4 |
| 11 | 6.1 | 17.7 | 2.9 |
| 94 | 5.7 | 3.8 | 0.7 |
| 68 | 13.1 | 44.4 | 3.4 |
| 75 | 13.0 | 17.2 | 1.3 |
| 81 | 4 | 12.4 | 3.1 |
| 78 | 7.6 | 8.9 | 1.2 |
| 98 | 9.6 | 8.8 | 0.9 |

The cytotoxicity of the compounds described herein was also measured using the Jurkat human leukaemia cell line (JL$_C$) and also the amsacrine-resistant Jurkat human leukaemia cell line (JL$_A$) and the doxorubicin-resistant Jurkat human leukaemia cell line (JL$_D$). The cytotoxicity, as measured by the IC$_{50}$ (concentration required to give 50% cell kill) in the JL$_A$ or JL$_D$ cell line divided by the cytotoxicity in the JL$_C$ cell line gives an indication of the degree to which a compound may be affected by atypical drug resistance and is termed the resistance factor (Rf) of the compound. The method used has been described previously (Finlay et al, Eur J. Cancer 32A, 708–714, 1996). Compounds were active in the range 1 nM to 5 μM. Specific examples are listed in Table 3.

TABLE 3

| Compound | JL$_C$ IC$_{50}$ (nM) | JL$_A$ IC$_{50}$ (nM) | Rf (JL$_A$/JL$_C$) | JL$_D$ IC$_{50}$ (nM) | Rf (JL$_D$/JL$_C$) |
|---|---|---|---|---|---|
| TAS-103 | 5.4 | 302 | 55.9 | 384 | 71.1 |
| Doxorubicin | 7.0 | 25.9 | 3.7 | 109 | 15.6 |
| 4 | 19.0 | 26.6 | 1.4 | 22.8 | 1.2 |
| 3 | 27.0 | 21.6 | 0.8 | 24.3 | 0.9 |
| 2 | 37 | 96 | 2.6 | 107 | 2.9 |
| 35 | 28 | 19 | 0.7 | 25 | 0.9 |
| 78 | 21 | 14 | 0.7 | 17 | 0.8 |
| 81 | 8.7 | 9.2 | 1.1 | 9.3 | 1.1 |
| 84 | 4.4 | 9.8 | 2.2 | 7.2 | 1.6 |
| 87 | 16 | 16 | 1.0 | 17 | 1.0 |
| 94 | 9.2 | 16 | 1.8 | 14 | 1.6 |
| 98 | 8.6 | 18 | 2.1 | 14 | 1.6 |

Compounds were also studied for their ability to stabilize cleavable complexes in the presence of either topoisomerase I or II essentially as described previously (Finlay et al, Eur J. Cancer 32A, 708–714, 1996). Presence of cleavable complexes was indicated by an increase in the number and intensity of bands observed after electrophoresis and autoradiography. The results are expressed as the effective concentration range where an increase in cleavable complexes was observed relative to controls in the absence of drug. A number of compounds described herein were tested using these protocols and compounds showed poisoning of topoisomerases I and II in the range 0.01–20 μM. Specific examples are listed in Table 4.

TABLE 4

| Compound | Effective concentration range (μM) | |
| --- | --- | --- |
| | Topoisomerase I | Topoisomerase II |
| TAS-103 | 0.3–10.0 | 0.3–10.0 |
| 3 | 0.1–3.0 | 0.1–3.0 |
| 4 | 0.1–3.0 | 0.1–3.0 |
| 35 | 0.03–1.0 | 0.03–1.0 |
| 78 | 0.03–1.0 | 0.03–1.0 |
| 84 | 0.03–1.0 | 0.03–1.0 |

EXAMPLE 4

Pharmaceutical Composition

Tablets, each weighing 0.15 g and containing 25 mg of a compound of the invention can be manufactured as follows:

Composition for 10,000 Tablets
Compound of the invention (250 g)
lactose (800 g)
corn starch (415 g)
talc powder (30 g)
magnesium stearate (5 g)

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

EXAMPLE 5

Characterisation of Compounds of Formula (I)

The compounds prepared in Example 3 were characterised by proton N.M.R. spectroscopy and mass spectrometry. All proton NMR was performed at 400 MHz. Characterisation by mass spectrometry was performed using desorption chemical ionisation or electrospray ionisation. The results are set out in the following Table.

| Compound Number | Molecular Formula | Mass spec data | $^1$H N.M.R. data |
| --- | --- | --- | --- |
| 1 | C22H22N4O2 | MH+ @375 | DMSO; 10.39(t, 1 H), 9.32(d, J = 8.9 Hz, 1 H), 8.74(dd, J = 1.4, 7.6 Hz, 1 H), 8.40(dd, 1.49, 8.2 Hz, 1 H), 8.24(d, J = 9.3 Hz, 1 H), 8.03–7.95(m, 2 H), 7.64(d, J = 2.6 Hz, 1 H), 7.44(dd, J = 2.65, 8.9 Hz, 1 H), 4.02(s, 3 H), 3.72(q, J = 5.5 Hz, 2 H), 2.61(t, J = 5.5 Hz, 2 H), 2.36(s, 6 H) |
| 2 | C21H20N4O2 | MH+ @361 | DMSO; 10.58(s, 1 H), 10.40(br, 1 H), 9.14(br, 1 H), 8.66(m, 1 H), 8.42(dd, J = 1.51, 8.4 Hz, 1 H), 8.13(d, J = 9.4 Hz, 1 H), 8.03(m, 1 H), 7.89(d, J = 9.4 Hz, 1 H), 7.41(m, 2 H), 3.88(br, 2 H), 2.58(br, 2 H), 2.50(s, 6 H) |
| 3 | C22H22N4O2 | MH+ @ 375 | DMSO; 10.27(br, 1 H), 8.96(d, J = 8.19 Hz, 1 H), 8.71(dd, J = 7.20, 1.48 Hz, 1 H), 8.47(d, J = 9.5 Hz, 1 H), 8.41(dd, J = 8.19, 1.46 Hz, 1 H), 8.10(dd, J = 7.14, 1.24 Hz, 1 H), 7.93(d, J = 9.63 Hz, 1 H), 7.85(t, J = 8.14 Hz, 1 H), 7.46(d, J = 7.99 Hz, 1 H), 4.08(s, 3 H), 3.71(q, J = 5.56 Hz, 2 H), 2.63(t, J = 5.95 Hz, 2 H), 2.34(s, 6 H) |
| 4 | C21H20N4O2.HBr | M+ @360 | DMSO; 2.91(6 H, s), 3.45(2 H, t), 3.97–4.02(2 H, m), 7.37(1 H, d), 7.72–7.78(1 H, m), 7.92(1 H, d), 8.08–8.12(1 H, m), 8.45–8.51(2 H, m), 8.54–8.61(2 H, m), 9.42(1 H, br.), 10.13(1 H, t), 10.67(1 H, s). |
| 5 | C22H22N4O2 | MH+ at 375 | DMSO; 9.97(br. t., 1 H), 8.55(m, 2 H), 8.41(d, J = 7.48 Hz, 1 H), 8.18(d, J = 9.24 Hz, 1 H), 8.04(m, 2 H), 7.81(d, J = 9.20 Hz, 1 H), 7.56(m, 1 H), 4.06(s, 3 H), 3.79(q, J = 6.8 Hz, 2 H), 2.90(t, J = 2.91 Hz, 2 H), 2.47(s, 6 H). |
| 6 | C21H20N4O2 | MH+ at 361 | DMSO; 10.56(s, 1 H), 10.13(br. t, 1 H), 8.56(m, 1 H), 8.49(m, 2 H), 8.18(d, J = 9.2 Hz, 1 H), 8.10(m, 1 H), 8.02(d, J = 8.5 Hz, 1 H), 7.81(d, J = 9.2 Hz, 1 H), 7.40(m, 1 H), 4.07(q, J = 6.0 Hz, 2 H), 3.46(t, J = 6.0 Hz, 2 H), 2.89(s, 6 H) |
| 7 | C21H19N5O3 | DCI + NH3, MH+, 390 | (CDCL3), 2.50(6 H, s, 2×CH3), 2.75(2 H, t, CH2), 3.95(2 H, q, CH2), 7.95(1 H, t, ArH), 8.10(1 H, t, ArH), 8.30(1 H, d, ArH), 8.45(1 H, d, ArH), 8.50(1 H, d, ArH), 8.70(1 H, d, ArH), 9.10(1 H, dd, ArH), 9.90(1 H, d, ArH), 10.50(1 H, Br., NH). |
| 8 | C24H27N5O2 | MH+ at 418 | (CDCl3): 11.10(t, 1 H), 9.16(d, 1 H), 8.91(dd, 1 H), 8.38(dd, 1 H), 8.19(d, 1 H), 7.99–7.87(m, 2 H), 7.44(d, 1 H), 4.24(s, 2 H), 4.05(q, 2 H), 3.06(t, 2 H), 2.60(s, 6 H), 2.51(s, 6 H) OH not visible |
| 9 | C24H27N5O2 | MH+ 418 (small) | (d6-DMSO): 2.20(6 H, s), 2.35(6 H, s), 2.95(2 H, br), 3.85(2 H, br), 6.04(2 H, s), 7.45(1 H, br. s), 7.70–7.80(1 H, m), 7.90–8.00(2 H, m), 8.25–8.30(1 H, m), 8.45–8.60(2 H, m). |
| 10 | C22H21BrN4O2 | MH+ 453/455 (1:1) | (Chloroform): 10.73(br. t., 1 H), 8.92(dd, 1 H), 8.55(t, 1 H), 8.38(dd, 1 H), 8.04–7.90(m, 3 H), 7.10(d, 1 H), 4.09(s, 3 H), 3.85(q, 2 H), 2.74(t, 2 H), 2.33(s, 6 H) |
| 11 | C23H21N5O2 | MS DCI/NH3 m/e 400 (MH+, 100%) | CDCl3; 2.36(6 H, s), 2.68(2 H, t, J = 5.9 Hz), 3.81–3.84(2 H, m), 5.02(2 H, s), 7.30(1 H, d= 8.1 Hz), 7.71–7.75(1 H, m), 7.92–7.98(2 H, m), 8.36–8.41(2 H, m), 8.96(1 H, dd, J = 7.2, 1.5 Hz), 9.15(1 H, d, J = 8.3 Hz), 10.70(1 H, broad). |

-continued

| Compound Number | Molecular Formula | Mass spec data | ¹H N.M.R. data |
|---|---|---|---|
| 12 | C28H26N4O2 | MS DCI/NH3 m/e 451 (MH+, 100%) | CDCl3; 2.42(6 H, s), 2.75(2 H, t, J = 6.0 Hz), 3.89–3.93(2 H, m), 5.35(2 H, s), 7.33–7.49(4 H, m), 7.55(2 H, d, J = 7.2 Hz), 7.73–7.77(1 H, m), 7.95–8.0(2 H, m), 8.40(1 H, dd, J = 8.6, 1.5 Hz), 8.63(1 H, d, J = 9.4 Hz), 9.00–9.07(2 H, m), 10.90(1 H, broad). |
| 13 | C24H22N4O2 | MS DCI/NH3 m/e 399 (MH+, 100%) | CDCl3; 2.37(6 H, s), 2.55(1 H, t, J = 2.4 Hz), 2.70(2 H, t, J = 6.0 Hz), 3.82–3.87(2 H, m), 4.95(2 H, d, J = 2.4 Hz), 7.32(1 H, d, J = 8.3 Hz), 7.70–7.74(1 H, m), 7.90–7.95(2 H, m), 8.35(1 H, dd, J = 8.50, 1.6 Hz), 8.50(1 H, d, J = 9.8 Hz), 8.95(1 H, dd, J = 7.30, 1.5 Hz), 9.01(1 H, d, J = 8.2 Hz), 10.80(1 H, broad). |
| 14 | C23H24N4O3 | [M + H] + 405 | CDCl3; 10.82(1 H, br, s), 9.11(1 H, d, J8.9), 8.91(1 H, d, J7.3), 8.40–8.30(2 H, m), 7.90–7.81(2 H, m), 7.40(1 H, d, J9.0), 4.04(3 H, s), 4.01(3 H, s), 3.84(2 H, q, J, 6.0), 2.70(2 H, t, J, 6.0), 2.40(6 H, s) |
| 15 | C23H24N4O2 | MS DCI/NH3 m/e 389 (MH+, 100%) | d6-DMSO; 1.52(3 H, t, J = 6.9 Hz), 2.35(6 H, s), 2.65(2 H, t, J = 5.9 Hz), 3.72–3.75(2 H, m), 4.30(2 H, q, J = 6.9 Hz), 7.43(1 H, d, J = 7.9 Hz), 7.80–7.84(1 H, m), 7.92(1 H, d, J = 9.5 Hz), 8.05–8.10(1 H, m), 8.42(1 H, dd, J = 8.6, 1.6 Hz), 8.45(1 H, d, J = 9.5 Hz), 8.72(1 H, dd, J = 7.1, 1.5 Hz), 8.94(1 H, d, J = 8.2 Hz), 10.25(1 H, t, J = 5.0 Hz). |
| 16 | C25H28N4O2 | EI+ m/z 416 (M+, 12%); 346 (100%); 329 (58%); | CDCl3; 10.87(1 H, br); 8.93(1 H, d, J = 9.5 Hz); 8.54(1 H, d, J = 9.5 Hz); 8.35(1 H, dd, J = 8.4, 1.5 Hz); 7.89(2 H, m); 7.69(1 H, d, J = 8.0 Hz); 7.19(1 H, m); 3.93(2 H, d, J = 6.4 Hz); 3.87(2 H, m); 2.75(2 H, m); 2.40(6 H, s); 2.24(1 H, m); 1.11(6 H, d, J = 6.8 Hz). |
| 17 | C28H25ClN4O2 | DEI m/e 484/486 3:1 (M+, 100) | d6-DMSO; 2.38(6 H, s); 2.62–2.70(2 H, m); 3.70–3.77(2 H, m); 5.44(2 H, s); 7.52(2 H, d, J = 8.3 Hz); 7.58(1 H, d, J = 8.0 Hz); 7.64(2 H, d, J = 8.3 Hz); 7.88(1 H, t, J = 8.1 Hz); 8.01(1 H, d, J = 9.5 Hz); 8.10(1 H, t, J = 7.8 Hz); 8.46(1 H, d, J = 8.4 Hz); 8.56(1 H, d, J = 9.5 Hz); 8.73(1 H, d, J = 7.0 Hz); 9.03(1 H, d, J = 8.0 Hz); 10.22–10.30(1 H, broad peak). |
| 18 | C24H26N4O3 | DCI + NH3 m/e 419(M+, 100) | CDCl3; 2.69(6 H, s); 2.92–3.10(2 H, m); 3.49(3 H, s); 3.83–3.93(2 H, t, J = 4.4 Hz); 3.94–4.10(2 H, m); 4.28–4.40(2 H, t, J = 4.4 Hz); 7.22(1 H, d, J = 8.0 Hz); 7.80(1 H, t); 7.84–7.96(2 H, m, J = 4.7 Hz, 8.3 Hz); 8.37(1 H, d, J = 8.2 Hz); 8.54(1 H, d, J = 9.4 Hz); 8.82(1 H, d, J = 7.4 Hz); 8.90(1 H, d, J = 6.9 Hz); 11.10(1 H, broad peak). |
| 19 | C25H26N4O4 | CI+ (NH3) m/z 447 (MH+, 100%) | CDCl3; 10.76(1 H, br); 9.01(1 H, d, J = 8.2 Hz); 8.94(1 H, dd, J = 7.3, 1.5 Hz); 8.58(1 H, d, J = 9.5 Hz); 8.34(1 H, dd, J = 8.4, 1.5 Hz); 7.91(2 H, m); 7.66(1 H, t, J = 8.1 Hz); 7.08(1 H, d, J = 8.0 Hz); 4.83(2 H, s); 4.27(2 H, q, J = 7.1 Hz); 3.83(2 H, m); 2.69(2 H, m); 2.36(6 H, s); 1.27(3 H, t, J = 7.1 Hz). |
| 20 | C21H19BrN4O2 | DCI + NH3: m/z 439/441 1:1 (MH+) | (CDCl3): 2.44(6 H, s), 2.76(2 H, t, J = 6.0), 3.89(2 H, q, J = 6.0), 7.84(1 H, d, J = 8.7), 7.90–8.00(2 H, m), 8.39(1 H, d, J = 8.6), 8.58(1 H, d, J = 9.6), 8.85(1 H, d, J = 8.8), 8.99(1 H, d, J = 7.2) |
| 21 | C23H24N4O3 | CI+ (NH3) m/z 405 (MH+, 100%) | CDCl3; 10.69(1 H, br); 8.93(1 H, dd, J = 7.3, 1.5 Hz); 8.80(1 H, d, J = 8.3 Hz); 8.47(1 H, d, J = 9.6 Hz); 8.32(1 H, dd, J = 8.3, 1.5 Hz); 7.91(1 H, m); 7.85(1 H, d, J = 9.6 Hz); 7.57(1 H, t, J = 8.1 Hz); 7.11(1 H, d, J = 7.9 Hz); 4.27(2 H, m); 4.11(2 H, m); 3.83(2 H, q, J = 5.7 Hz); 2.68(2 H, t, J = 6.0 Hz); 2.35(6 H, s). |
| 22 | C25H22N6O2 | DCI/NH3 m/z 439 (MH+, 100%) | CDCl3; 2.40(6 H, s), 2.72(2 H, t, J = 5.90 Hz), 3.85–3.89(2 H, m), 7.05(1 H, t, J = 4.80 Hz), 7.63(1 H, d, J = 7.75 Hz), 7.80–7.95(3 H, m), 8.18(1 H, d, J = 9.5 Hz), 8.36(1 H, dd, J = 8.4, 1.4 Hz), 8.55(2 H, d, J = 4.80 Hz), 9.00(1 H, dd, J = 7.2, 1.3 Hz), 9.40(1 H, d, J = 8.1 Hz), 10.70 (1 H, broad). |
| 23 | C27H31N5O3 | DCI/NH3 m/z 474 (MH+, 100%) | CDCl3; 2.45(6 H, s), 2.68–2.71(4 H, m), 2.75(2 H, t, J = 6.0 Hz), 3.01(2 H, t, J = 5.6 Hz), 3.75–3.79(4 H, m), 3.88–3.92(2 H, m), 4.36(2 H, t, J = 5.6 Hz), 7.25–7.27(1 H, m), 7.71–7.75(1 H, m), 7.95–8.01(2 H, m), 8.41(1 H, dd, J = 8.5, 1.5 Hz), 8.55(1 H, d, J = 9.5 Hz), 9.01–9.05(2 H, m), 10.8(1 H, broad). |
| 24 | C25H25N5O2 | DCI/NH3 m/z 428 (MH+, 100%) | CDCl3; 2.35–2.38(2 H, m), 2.45(6 H, s), 2.73–2.75(4 H, m), 3.89–3.93(2 H, m), 4.37(2 H, J = 5.7 Hz), 7.28–7.30(1 H, m), 7.78–7.80(1 H, m), 7.98–8.01(2 H, m), 8.45(1 H, dd, J = 8.4, 1.5 Hz), 8.56(1 H, d, J = 9.7 Hz), 9.05(1 H, dd, J = 7.2, 1.5 Hz), 9.08(1 H, d, J = 8.2 Hz), 10.8(1 H, broad). |
| 25 | C22H22N4O | [M + H] + 359 | (CDCl3)10.88(1 H, br, s), 9.34(1 H, d, J7.9), 9.02(1 H, dd, J7.3, 1.5), 8.42(1 H, dd, J8.4, 1.5), 8.31(1 H, d, J9.4), 8.02(1 H, d, J9.6), 7.98(1 H, d, J7.3), 7.73(1 H, t, J7.6), 7.69(1 H, J, 6.9), 3.91(2 H, q, J5.7), 2.75(3 H, s), 2.60(2 H, t, J5.7), 2.44(6 H, s) |
| 26 | C21H19FN4O | [M + H] + 363 | (CDCl3)10.67(1 H, s, br), 9.22(1 H, d, J8.1), 8.97(1 H, dd, J7.3, 1.5), 8.36(1 H, dd, J8.4, 1.5), 8.29(1 H, d, J9.5), 7.97(1 H, d, J9.5), 7.93(1 H, dd, J8.5, 7.2), 7.71(1 H, m), 7.47(1 H, m), 3.83(2 H, q, J5.5), 2.68(2 H, t, J5.8), 2.37(6 H, s), |
| 27 | C26H31N5O2 | DCI/NH3 m/z 446 (MH+, 100%) | CDCl3; 2.15–2.21(2 H, m), 2.34(6 H, s), 2.44(6 H, s), 2.63(2 H, t, J = 7.2 Hz), 2.79(2 H, t, J = 6.0 Hz), 3.90–3.95(2 H, m), 4.30(2 H, t, J = 6.3 Hz), 7.25–7.27(1 H, m), 7.71–7.74(1 H, m), 7.95–8.01 (2 H, m), 8.40(1 H, dd, J = 8.40, 1.5 Hz), 8.55(1 H, d, J = 9.5 Hz), 8.99–9.03(2 Hm), 10.89(1 H, broad). |
| 28 | C22H22N4OS | EI+ m/z 390 (M+, 14%); 320 (100%). | CDCl3; 10.79(1 H, br); 9.32(1 H, m); 9.02(1 H, dd, J = 7.2, 1.5 Hz); 8.63(1 H, d, J = 9.7 Hz); 8.42(1 H, dd, J = 8.4, 1.5 Hz); 8:05(1 H, d, J = 9.7 Hz); 7.99(1 H, m); 7.76(2 H, m); 3.90(2 H, m); 2.75(2 H, m); 2.66(3 H, m); 2.43(6 H, s) |
| 29 | C23H23N5O3 | DCI/NH3 m/z 418 (MH+, 100%) | CDCl3 and two drops of D4-MeOH 2.32(6 H, s), 2.68(2 H, t, J = 6.2 Hz), 3.78(2 H, t, J = 6.2 Hz), 4.68(2 H, s), 7.20(1 H, d, J = 7.8 Hz), 7.70–7.72(1 H, m), 7.90–7.95(2 H, m), 8.35(1 H, dd, J = 1.5, 8.5 Hz), 8.53(1 H, d, J = 9.8 Hz), 8.86(1 H, d, J = 7.2, 1.5 Hz), 8.95(1 H, d, J = 8.3 Hz). 3 exchangeable protons not visible due to presence of methanol (d4). |
| 30 | C21H20N4O3 | DCI/NH3 m/z 377 (MH+, 100%) | CDCl3; 2.81(1 H, dd, J = 12.6, 7.5 Hz), 2.97(1 H, dd, J = 12.6, 3.7 Hz), 3.70–3.75(1 H, m), 3.90–4.00(2 H, m), 4.01(3 H, s), 7.15(1 H, d, J = 8.0 Hz), 7.65–7.71(1 H, m), 7.81(1 H, d, J = 9.5 Hz), 7.85–7.90(1 H, m), 8.31(1 H, d, J = 7.5 Hz), 8.42(1 H, d, J = 9.6 Hz), 8.80(1 H, d, J = 8.2 Hz), 8.88(1 H, d, J = 6.1 Hz), 11.2(1 H, broad). OH and NH2 not visible in NMR |

-continued

| Compound Number | Molecular Formula | Mass spec data | ¹H N.M.R. data |
|---|---|---|---|
| 31 | C23H24N4O2 | DCI + NH3 389 (MH+) | DMSO; 1.92(2 H, t, J = 7.03 Hz), 2.2(6 H, s), 2.48(2 H, t, J =Hz), 3.62(2 H, q, J = 6.74 Hz), 4.07(3 H, s), 7.3(1 H, d, J = 8.03 Hz), 7.85(1 H, t, J = 8.06), 7.98(1 H, d, J = 9.48), 8.05(1 H, t, J = 7.25 Hz), 8.42(1 H, d, J = 8.64 Hz), 8.49(1 H, d, J = 9.6 Hz), 8.52(1 H, d, J = 6.9 Hz), 8.72(1 H, d, J = 8.06 Hz), 9.95(1 H, broad) |
| 32 | C21H19BrN4O | CI+ m/z 423:425 (1:1, MH+, 98%) | CDCl3; 10.61(1 H, br); 9.41(1 H, d, J = 8.0 Hz); 8.97(1 H, dd, J = 7.3, 1.6 Hz); 8.47(1 H, d, J = 9.8 Hz); 8.36(1 H, dd, J = 8.4, 1.5 Hz); 8.02(2 H, m); 7.94(1 H, m); 7.61(1 H, t, J = 7.9 Hz); 3.84(2 H, m); 2.69(2 H, br t, J = 5.9 Hz); 2.37(6 H, s). |
| 33 | C23H22N4O3 | m/z 403 (MH+) | d6-DMSO: 2.37(6 H, s), 2.52(3 H, s), 2.65(2 H, t, J = 6.0), 3.72(2 H, q, J = 6.0), 7.74(1 H, d, J = 7.0), 7.99(1 H, t, J = 8.0), 8.08(1 H, d, J = 9.6), 8.12(1 H, t, J = 7.8), 8.31(1 H, d, J = 9.6), 8.47(1 H, d, J = 8.0), 8.75(1 H, d, J = 7.0), 9.38(1 H, d, J = 8.0) |
| 34 | C24H24N4O3 | MS DCI/NH3 m/z 417 (MH+, 100%) | CDCl3; 2.42(6 H, s), 2.45(3 H, s), 2.75(2 H, t, J = 5.9 Hz), 3.88–3.91(2 H, m), 4.83(2 H, s), 7.12(1 H, d, J = 7.8 Hz), 7.71–7.76(1 H, m), 7.95–8.02(2 H, m), 8.45(1 H, d, J = 8.4, 1.4Mz), 8.63(1 H, d, J = 9.6 Hz), 9.03(1 H, dd, J = 7.2, 1.6 Hz), 9.15(1 H, d, J = 8.1 Hz), 10.80(1 H, broad). |
| 35 | C23H24N4O2 | DCI/NH3 m/z 389 (MH+, 100%) | CDCl3; 1.53(3 H, d, J = 6.5 Hz), 2.37(6 H, s), 2.55(1 H, dd, J = 12.2, 6.2 Hz), 2.84(1 H, dd, J = 12.2, 7.8 Hz), 4.10(3 H, s), 4.55–4.65(1 H, m), 7.28–7.30(1 H, m), 7.75–7.80(1 H, m), 7.95–8.02 (2 H, m), 8.42(1 H, dd, J = 8.4, 1.5 Hz), 8.57(1 H, d, J = 9.5 Hz), 8.81(1h, d, J = 8.2 Hz), 9.02 (1 H, dd, J = 7.3, 1.6 Hz), 10.9(1 H, d, J = 7.2 Hz). |
| 36 | C22H19N5O | MH+ at 370 | DMSO; 9.99(t, 1 H), 9.62(d, 1 H), 8.74(dd, 1 H), 8.41(m, 2 H), 8.35(d, 1 H), 8.24(d, 1 H), 8.10–8.00(m, 2 H), 3.72(q, 2 H), 2.62(t, 2 H), 2.35(s, 6 H). |
| 37 | C24H25N5O3 | DCI + NH3 432(MH+) | d6-DMSO; 0.9(3 H, t, J = 7.4 Hz), 2.4(6 H, s), 2.75(2 H, broad), 3.37(2 H, t, J = 6.42 Hz), 5.3(2 H, broad), 7.57(1 H, d, J = 7.21 Hz), 7.75(1 H, t, J = 7.4 Hz), 7.91(2 H, t, J = 7.14 Hz), 8.13(1 H, d, J = 9.58 Hz), 8.3(1 H, d, J = 8.43 Hz), 8.95(1 H, d, J = 6.72 Hz), 9.21(1 H, d, J = 7.64 Hz), 10.76(1 H, broad) One NH not visible |
| 38 | C21H19N5O3 | DCI + NH3; MH+, 390 | (CDCL3), 2.50(6 H, s, 2×CH3), 3.10(2 H, t, CH2), 4.05(2 H, q, CH2), 8.10(1 H, dd, ArH), 8.15(2 H, dd, ArH), 8.20(1 H, d, ArH), 8.45(1 H, d, ArH), 8.60(1 H, dd, ArH), 9.0(1 H, dd, ArH), 9.90(1 H, d, ArH), 10.40(1 H, br., NH) |
| 39 | C22H22N4O3S | CI+ (NH3) m/z 423 (MH+, 100%) | d6-DMSO: 9.79(1 H, br m); 9.64(1 H, d, J = 8.0 Hz); 9.10(1 H, d, J = 9.8 Hz); 8.65(1 H, m); 8.59(2 H, m); 8.40(1 H, d, J = 9.8 Hz); 8.24(2 H, m); 4.04(2 H, br m); 3.57(3 H, s); 3.53 (2 H, br t, J = 6.3 Hz); 2.99(6 H, s). |
| 40 | C21H19ClN4O | DCI + NH3 m/e 379 (MH+, 100) | CDCl3; 2.38(6 H, s); 2.62–2.70(2 H, t, J = 8.0 Hz); 3.78–3.86(2 H, m, J = 5.4, 3.0 Hz); 7.69(1 H, t, J = 8.0 Hz); 7.72(1 H, d, J = 0.9, 6.8 Hz); 7.94(1 H, t, J = 1.3, 7.2 Hz); 8.04(1 H, d, J = 9.5 Hz); 8.37(1 H, d, J = 1.5, 6.9 Hz); 8.51(1 H, d, J = 9.4 Hz); 8.98(1 H, d, J = 1.5, 5.6 Hz); 9.99(1 H, d, J = 8.0 Hz); 10.60(1 H, broad peak). |
| 41 | C21H19N7O | [M + H] + 386 | (CDCl3); 10.75(1 H, br), 9.30(1 H, d, J8.2), 9.04(1 H, d, J7.3), 8.42(2 H, t, J8.4), 8.00(2 H. t. J7.8), 7.85(1 H, t, J9.1), 7.63(1 H, d, J7.8), 3.90(2 H, q, br), 2.76(2 H, t, br), 2.45(6 H, s) |
| 42 | C21H21N5O | DCI + NH3, MH+, 360 | (CDCL3), 2.50(6 H, s, 2×CH3), 2.90(2 H, t, CH2), 3.95(2 H, m, CH2), 7.10(1 H, dd, ArH) 7.65(1 H, t, ArH), 7.90(2 H, m. ArH), 8.05(1 H, d, ArH), 8.35(1 H, d, ArH), 8.70(1 H, d, ArH), 8.95(1 H, d, ArH), 11.0(1 H, br., NH) |
| 43 | C25H23F3N4O6 | DCI/NH3 m/z 419 (MH+, 100%) | d6-DMSO: 2.70(6 H, s), 3.18(2 H, t), 3.89–3.95(2 H, m), 5.00(2 H, s), 7.42(1 H, d, J = 8.0 Hz), 7.81–7.86(1 H, m), 8.00(1 H, d, J = 8.0 Hz), 8.08–8.12(1 H, m), 8.46(1 H, d, J = 7.8 Hz), 8.55–8.62(1 H, d, J = 8.1 Hz), 8.85(1 H, d, J = 8.1 Hz), 10.1(1 H, broad). 2 acidic OH not visible |
| 44 | C23H23N5O2 | MH+, 402 | (CDCl3), 2.35(6 H, s, 2×CH3), 2.40(3h, s, CH3), 2.65(2 H, t, CH2), 3.80(2 H, q, CH2), 7.45(1 H, t, ArH), 7.70(2 H, m, ArH), 7.90(2 H, m, ArH), 8.20(1 H, s, NH), 8.25(1 H, d, ArH), 8.70(1 H, d, ArH), 8.80(1 H, d, ArH), 10.10(1 H, br, NH) |
| 45 | C23H22N4O3 | m/z 403 (MH+) | (CDCl3): 2.38(6 H, s), 2.70(2 H, t, J = 5.8), 3.87(2 H, q, J = 5.8), 4.03(3 H, s), 7.81(1 H, t, J = 7.9), 7.96(1 H, t, J = 7.8), 8.07(1 H, d, J = 9.8), 8.35–8.40(2 H, m), 9.00(1 H, d, J = 7.2), 9.13(1 H, d, J = 9.8), 9.68(1 H, d, J = 8.1), 10.65(1 H, br) |
| 46 | C23H25N5O5S2 | DCI + NH3, MH+ 516 | (CDCL3), 2.45(6 H, s, 2×CH3), 2.75(2 H, t, CH2), 3.60(6 H, s, 2×CH3), 3.90(2 H, q, CH2), 7.85(1 H, d, ArH), 7.95(1 H, t, ArH), 8.05(1 H, d, ArH), 8.20(1 H, d, ArH), 8.35(1 H, d, ArH), 8.45(1 H, d, ArH), 9.08(1 H, d, ArH), 9.75(1 H, d, ArH), 10.65(1 H, br. NH) |
| 47 | C21H21N5O | DCI + NH3; MH+, 360 | (CDCl3), 2.45(6 H, s, 2×CH3), 2.90(2 H, t, CH2), 3.95(2 H, q, CH2), 4.45(2 H, br. NH2), 7.10(1 H, dd, ArH), 7.65(1 H, d, ArH), 7.70(1 H, d, ArH), 7.90(2 H, m, ArH), 8.30(1 H, d, ArH), 8.35(1 H, d, ArH), 8.85(1 H, d, ArH), 11.05(1 H, br, NH) |
| 48 | C22H22N6O2 | MH+ 403 | d6-DMSO; 2.33(6 H, s), 2.63(2 H, t, J = 5.91 Hz), 3.69–3.78(2 H, m), 6.16(1 H, s), 7.8(1 H, broads), 7.93–8.12(4 H, m), 8.22(1 H, broads), 8.42–8.49(1 H, m), 8.58(1 H, d, J = 11.82 Hz), 8.72(1 H, d, J = 7.22 Hz), 9.48–9.52(1 H, m), 10.16–10.25(1 H, broadm) |
| 49 | C22H22N4O2 | CI+ m/z 375 (MH+, 100%) | CDCl3; 10.64(1 H, br); 8.92(1 H, dd, J = 7.1, 1.5 Hz); 8.80(1 H, d, J = 7.1, 1.5 Hz); 8.24 (2 H, m); 7.86(1 H, m); 7.69(3 H, m); 5.09(2 H, s); 3.83(2 H, m); 2.85(2 H, br m); 2.50(6 H, br s) |
| 50 | C24H21F3N4O5 | m/z 389 (MH+) | (d6-DMSO): 2.94(6 H, d, J = 3.7), 3.49(2 H, m), 4.00(2 H, q, J = 6.2), 8.05(1 H, t, J = 7.9), 8.12–8.22(2 H, m), 8.48–8.58(3 H, m), 9.17(1 H, d, J = 9.8), 9.41(1 H, d, J = 8.2), 9.82(1 H, t) |
| 51 | C24H24F3N5O5S | DCI/NH3 m/z 438 (MH+), 100% | CDCl3/d4-MeOD 2.67(3 H, s), 3.05(6 H, s), 3.62(2 H, t), 4.25(2 H, t), 8.00–8.10(3 H, m), 8.45–8.50(1 H, m), 8.88(1 H, d), 8.99(1 H, d), 9.35(1 H, d). 2NH not visible due to presence of MeOD |
| 52 | C24H24F3N5O5S | DCI/NH3 m/e 438 (MH+), 100% | CDCL3 and MeOD 2.62(3 H, s), 3.01(6 H, s), 3.66(2 H, t), 4.13(2 H, t), 7.92–7.99(1 H, m), 8.02–8.08(3 H, m), 8.15(1 H, dd), 8.39(1 H, dd), 8.80(1 H, dd), 9.49(1 H, d). No NHs visible due to presence of MeOD |
| 53 | C23H23N5O2 | DCI + NH3, MH+ 402 | (CDCl3), 2.32(3 H, s, CH3), 2.40(6 H, s, 2×CH3), 2.80(2 H, t, CH2), 4.05(2 H, q, CH2), 7.75–8.0(5 H, m, ArH), 8.10(1 H, br., NH), 8.35(1 H, dd, ArH), 8.95(1 H, dd, ArH), 9.30(1 H, d, ArH), 10.75(1 H, t, NH). |
| 54 | C23H25N5O | DCI + NH3, MH+ 388 | (CDCL3), 2.40(6 H, s, 2×CH3), 2.70(2 H, t, CH2), 2.90(6 H, s, 2×CH3), 3.85(2 H, q, CH2), 7.40(1 H, d, ArH), 7.70(1 H, t, ArH), 7.90(2 H, dd, ArH), 8.40(1 H, dd, ArH), 8.53(1 H, d, ArH), 8.95(1 H, dd, ArH), 9.10(1 H, d, ArH), 10.85(1 H, br. NH) |

-continued

| Compound Number | Molecular Formula | Mass spec data | ¹H N.M.R. data |
|---|---|---|---|
| 55 | C22H23N5O3S | m/z 438 (MH+) | (d4-MeOH)d8.98(1 H), 8.79(1 H), 8.65(1 H), 8.42(1 H), 8.09(1 H), 8.02–7.92(3 H, m), 4.22(2 H, t), 3.70(2 H, t), 3.24(3 H, s), 3.18(6 H, s) 2NH not visible |
| 56 | C22H23N5O3S | m/z 438 (MH+) | (d4-MeOH); 9.22(1 H, br. s), 8.91(1 H, dd, 7.3, 1.3), 8.49(1 H, d, 8.5), 8.19(1 H, d, 9.3), 8.13(1 H, dd, 7.4, 7.3), 8.07(1 H, d, 8.4), 7.92(1 H, d, 9.2), 7.60(1 H, dd, 8.4, 2.2), 4.29(2 H, t, 6.2), 3.71(2 H, t, 6.2), 3.25(3 H, s), 3.18(6 H, s) |
| 57 | C23H25N5O3S | DCI + NH3 MH+ (452) | CDCl3; 2.42(6 H, s), 2.73(2 H, t, J = 5.69 Hz), 2.89(6 H, s), 3.85–3.92(2 H, m), 7.91(1 H, t, J = 7.91 Hz), 8.02(1 H, t, J = 7.34 Hz), 8.16(1 H, d, J = 9.83 Hz), 8.41–8.51(2 H, m), 9.05(1 H, d, J = 9.84 Hz), 9.85(1 H, d, J = 8.1 Hz), 10.54(1 H, broad) |
| 58 | C23H25N5O3S | DCI + NH3 MH+ (452) | CDCl3; 2.31(6 H, s), 2.79(6 H, s), 2.8–2.9(2 H, m), 3.85–3.92(2 H, m), 7.96(1 H, t, J = 7.19 Hz), 8.05–8.15(4 H, m), 8.38(1 H, dd, J = 8.51 Hz, J = 1.53 Hz), 8.93(1 H, dd, J = 7.29 Hz, 1.53 Hz), 9.46(1 H, s), 10.32(1 H, broad) |
| 59 | C23H22N6O | DCI + NH3, MNH4+, 416 | (CDCl3), 2.45(6 H, s, 2×CH3), 2.80(2 H, t, CH2), 3.10(2 H, s, CH2), 3.90(2 H, q, CH2), 7.03(1 H, m, ArH), 7.75(1 H, t, ArH), 7.95(2 H, m, ArH), 8.12(1 H, d, ArH), 8.40(1 H, d, ArH), 8.80(1 H, d, ArH), 9.05(1 H, d, ArH), 10.95(1 H, NH). One NH not visible |
| 60 | C23H24N4O3 | DCI/NH3 m/z 405 (MH+, 100%) | 400 MHz, CDCl3. 2.25(6 H, s), 2.80(2 H, t, J = 6.1 Hz), 3.82–3.87(2 H, m), 4.06(3 H, s), 4.10(3 H, s), 6.78(1 H, broad), 7.19(1 H, d, J = 7.7 Hz), 7.63–7.70(2 H, m), 7.85(1 H, d, J = 9.5 Hz), 8.28(1 H, d, J = 9.4 Hz), 8.45(1 H, d, J = 9.4 Hz), 8.95(1 H, d, J = 8.2 Hz). |
| 61 | C23H24N4O2 | DCI + NH3, MH+ 389 | CDCl3; 10.76(1 H, br s); 8.97(2 H, m); 8.52(1 H, m); 8.40(1 H, m); 7.95(2 H, m); 7.75(1 H, m); 7.23(1 H, m); 4.05(3 H, m); 3.93(1 H, m); 3.70(1 H, m); 3.08(1 H, m); 2.45(6 H, s)1.18(3 H, dJ = 6.51 Hz) |
| 62 | C24H22F3N5O4 | m/z 388 (MH+) | (d6-MeOH): 3.19(6 H, s), 3.71(2 H, t, J = 6.0), 4.25(2 H, t, J = 6.0), 8.01–8.16(4 H, m), 8.51(1 H, dd, J = 8.7 and 1.4), 8.65(1 H, d, J = 9.8), 8.82(1 H, dd, J = 6.9 and 0.5), 9.27(1 H, d, J = 8.0). 3NH not visible |
| 63 | C23H23ClN4O3 | DCI/NH3 m/e 439/441 (MH+, 100%/30%) | 400 MHz, CDCl3 2.25(6 H, s), 2.62(2 H, t, J = 6.0 Hz), 3.75–3.80(2 H, m), 4.09(3 H, s), 4.13(3 H, s), 6.60(1 H, 7.11(1 H, d, J = 8.7 Hz), 7.73–7.78(2 H, m), 7.92(1 H, d, J = 9.5 Hz), 8.26(1 H, d, 9.5 Hz), 8.49(1 H, d, J = 9.5 Hz). |
| 64 | C21H21N5O3S | DCI + NH3 (MH+) 424 | CDCL3; 2.43(6 H, s), 2.95–3.1(2 H, m), 3.94–4.1(2 H, m), 7.93(1 H, t, J = 7.88 Hz), 8.06–8.1(3 H, m), 8.35(2 H, t, J = 8.65 Hz), 8.9(1 H, d, J = 5.87 Hz), 9.59(1 H, s), 10.98(1 H, broad). NH2 not seen |
| 65 | C24H26N4O2 | MH+ at 403 (100%) | (d6-DMSO): 9.67(br, 1 H), 8.95(d, 1 H), 8.56(d, 1 H), 8.50(d, 1 H), 8.43(1 H), 8.07(m, 1 H), 7.98(d, 1 H), 7.86(m, 1 H), 7.48(d, 1 H), 4.07(s, 3 H), 2.78(s, 2 H), 2.30(s, 6 H), 1.56(s, 6 H). |
| 66 | C21H19N5O3 | m/z 390 (MH+) | (CDCl3)10.72(1 H, br. t), 9.98(1 H, d, 2.2), 8.80(1 H, dd, 6.6, 1.4), 8.56(1 H, dd, 8.5, 2.3), 8.41(1 H, dd, 8.0, 1.4), 8.13(1 H, d, 9.3), 8.10–8.03(2 H, m), 7.98(1 H, d, 7.3, 8.5), 4.26(2 H, q, 6.1), 3.59(2 H, q, 5.6), 2.92(6 H, d, 5.0) |
| 67 | C23H24N4O2 | DCI/NH3 m/z 389 (MM+, 100%) | CDCl3, 400 MHz. 2.42(6 H, s), 2.76(2 H, t, J = 6.0 Hz), 3.00(3 H, s), 3.88–3.92(2 H, m), 4.10(3 H, s), 7.30(1 H, d), 7.75–7.79(1 H, m), 7.82(1 H, d, J = 9.4 Hz), 8.03(1 H, d, J = 9.7 Hz), 8.55(1 H, d, J = 9.7 Hz), 8.90(1 H, d, J = 7.4 Hz), 9.03(1 H, d, J = 8.0 Hz), 10.95(1 H, broad). |
| 68 | C21H20N4O3 | DCI/NH3 m/z 377 (MH+, 100%) | 400 MHz, d6-DMSO 2.33(6 H, s), 2.67(2 H, t, J = 5.7 Hz), 3.75–3.80(2 H, m), 7.32(1 H, d, J = 7.3 Hz), 7.64(1 H, d, J = 9.4 Hz), 7.70–7.74(1 H, m), 7.85(1 H, d, J = 9.4 Hz), 8.3(1 H, d, J = 9.4 Hz), 8.40(1 H, d, J = 9.4 Hz), 8.78(1 H, d, J = 8.1 Hz), 10.55(1 H, broad), 11.4(1 H, broad). one exchangeable proton not visible |
| 69 | C24H24N4O4 | MH+ at 433 (100%) | d6-DMSO: 11.93(1 H, br. d), 8.94(2 H, m), 8.60(1 H, d, J = 9.52 Hz), 8.52(1 H, dd, J = 8.6, 1.5 Hz), 7.97(2 H, m), 7.88(1 H, t, J = 8.15 Hz), 7.34(1 H, d, J = 7.95 Hz), 5.61(1 H, m), 4.10(3 H, s), 3.96(3 H, s), 3.90–3.70(2 H, m), 3.04(6 H, s) |
| 70 | C23H23ClN4O4 | MH+ at 419 | d6-DMSO: 10.74(1 H, br. d), 9.01(1 H, d, J = 8.19 Hz), 8.69(1 H, d, J = 7.06 Hz), 8.55(2 H, m), 8.14(1 H, t, J = 7.25 Hz), 8.03(1 H, d, J = 9.49 Hz), 7.86(1 H, t, J = 8.19 Hz), 7.54(1 H, d, 8.00 Hz), 5.39(1 H, m), 4.10(3 H, s), 3.80–3.60(2 H, m), 2.95(6 H, br. s). |
| 71 | C24H26N4O2 | m/z 403 (MH+) | (400 MHz, CDCl3): 1.11(3 H, t, 7.5), 1.78–1.89(1 H, m), 1.98–2.08(1 H, m), 2.36(6 H, s, NMe2), 2.59(1 H, dd, J = 12.5 and 6.1), 2.82(1 H, dd, J = 12.5 and 7.6), 4.10(3 H, s, OMe), 4.46–4.54(1 H, m, N—CH—), 7.27(1 H, d, J = 9.0), 7.76(1 H, t, J = 8.1), 7.94–8.01(2 H, m), 8.41(1 H, d, J = 8.5), 8.57(1 H, d, J = 9.4), 8.79(1 H, d, J = 8.2), 9.01(1 H, d, J = 7.1), 10.92(1 H, d, J = 8.3, NH) |
| 72 | C24H26N4O3 | DCI/NH3 m/e 419 (MH+, 100%) | 400 MHz, CDCl3 1.55(3 H, d, J = 6.4 Hz), 2.31(6 H, s), 2.39(1 H, dd, J = 12.2, 6.3 Hz), 2.61(1 H, dd, J = 12.2, 8.6 Hz), 4.07(3 H, s), 4.10(3 H, s), 4.40–4.50(1 H, m), 6.51(1 H, broad d, J = 6.1 Hz), 7.20(1 H, d, J = 7.7 Hz), 7.65–7.71(2 H, m), 7.88(1 H, d, J = 9.6 Hz), 8.28(1 H, dJ = 9.6 Hz), 8.45(1 H, d, J = 9.7 Hz), 8.98(1 H, d, J = 8.0 Hz). |
| 73 | C22H21ClN4O2 | DCI/NH3 m/e 411/409 (MH+, 30, 100%) | 400 MHz, CDCl3 2.42(6 H, s), 2.75(2 H, t, J = 5.9 Hz), 3.86–3.90(2 H, m), 4.08(3 H, s), 7.25(1 H, d, J = 7.8 Hz), 7.72–7.77(1 H, m), 7.89(1 H, d, J = 9.3 Hz), 8.36(1 H, d, J = 2.5 Hz), 8.56(1 H, d, J = 9.6 Hz), 8.92(1 H, d, J = 2.5 Hz), 8.95(1 H, d, J = 8.1 Hz), 10.75(1 H, broad). |
| 74 | C25H28N4O2 | [M + H] + 417 | (400 MHz, CDCl3)10.90(1 H, d, br), 8.95(1 H, dd, J 7.3, 1.4), 8.71(1 H, d, J8.2), 8.48(1 H, d, J9.6), 8.33(1 H, dd, J8.6, 1.5), 7.90(2 H, m), 7.68(1 H, t, J8.1), 7.18(1 H, d, J9.6), 4.49(1 H, m), 4.01(3 H, s), 2.83(1 H, dd, J12.6, 9.1), 2.59(1 H, dd, J12.6, 4.8), 2.28(6 H, s), 2.16(1 H, m), 1.04(3 H, d, J2.6), 1.03(3 H, d, J 2.6) |
| 75 | C23H24N4O3 | DCI + NH3, MH+ at 405 | CDCl3: 11.05, (1 H, d)8.91, (1 H, dd, J = 1.47 Hz, 7.29 Hz)8.85, (1 H, d, J = 8.17 Hz)8.50, (1 H, d, J = 9.55 Hz)8.35, (1 H, dd, J = 1.48, 8.47)7.88, (2 H, m)7.71, (1 H, t, J = 8.14)7.20(1 H, s) 4.55, (1 H, m)4.05(5 H, m)2.87, (2 H, m)2.35, (6 H, s). One exchangeable proton not visible. |

-continued

| Compound Number | Molecular Formula | Mass spec data | ¹H N.M.R. data |
|---|---|---|---|
| 76 | C29H28N4O2 | [M + H] + 465 | (400 MHz, CDCl3)11.0(1 H, d, br), 9.02(1 H, dd, J7.2, 1.5), 8.55(1 H, d, J9.4), 8.42(1 H, dd, 8.5, 1.6), 8.24(1 H, d, J8.2), 7.99(1 H, d, J8.3), 7.96(1 H, t, J9.2), 7.55(1 H, t, J8.1), 7.32(2 H, d, J7.1), 7.22(1 H, d, J8.0), 7.16(2 H, t, J7.5), 7.04(1 H, t, J7.3), 4.83(1 H, m), 4.09(3 H, s), 3.27(1 H, dd, J13.7, 5.9), 3.21(1 H, dd, J13.7, 5.5), 2.76(1 H, dd, J12.4, 8.3), 2.60(1 H, dd, J12.5, 6.1), 2.31(6 H, s) |
| 77 | C23H24N4O2 | DCI/NH3 m/z 389 (MH+, 100%) | 400 MHz, CDCl3 1.53(3 H, d, J = 6.5 Hz), 2.37(6 H, s), 2.55(1 H, dd, J = 12.2, 6.2 Hz), 2.84(1 H, dd, J = 12.2, 7.8 Hz), 4.10(3 H, s), 4.55–4.65(1 H, m), 7.28–7.30(1 H, m), 7.75–7.80(1 H, m), 7.95–8.02(2 H, m), 8.42(1 H, dd, J = 8.4, 1.5 Hz), 8.57(1 H, d, J = 9.5 Hz), 8.81(1h, d, J = 8.2 Hz), 9.02(1 H, dd, J = 7.3, 1.6 Hz), 10.9(1 H, d, J = 7.2 Hz). |
| 78 | C23H24N4O2 | m/z 389 (MH+) | (400 MHz, CDCl3): 1.53(3 H, d, J = 6.5, Me), 2.38(6 H, s, NMe2), 2.51–2.60(1 H, m), 2.82–2.90(1 H, m), 4.11(3 H, s, MeO), 4.56–4.65(1 H, m, CH), 7.29(1 H, d, J = 8.2), 7.78(1 H, t, J = 8.1), 7.96–8.02(2 H, m), 8.43(1 H, d, J = 8.4), 8.58(1 H, d, J = 9.5), 8.82(1 H, d, J = 8.4), 9.03(1 H, d, J = 7.3) |
| 79 | C22H21N5O3 | DCI + NH3, MH+, 404 | 400 MHz(CDCL3), 1.50(3 H, d, ), 2.35(6 H, s), 2.55(1 H, dd), 2.80(1 H, dd), 4.60(1 H, m), 7.90(1 H, t), 8.10(1 H, t, ), 8.25(1 H, d, ), 8.45(2 H, m.., ), 8.70(1 H, d), 9.05(1 H, dd), 9.65(1 H, d, ), 10.45(1 H, d, NH). |
| 80 | C22H21N5O3 | DCI + NH3, MH+ 404 | 400 MHz(CDCL3), 1.60(3 H, d.), 2.30(6 H, s), 2.65(1 H, m), 3.05(1 H, m), 4.70(1 H, m), 8.05(1 H, dd), 8.70(1 H, d), 8.75(1 H, d), 8.45(2 H, m, ), 8.70(1 H, d), 9.10(1 H, d, ), 10.00(1 H, d), 10.45(1 H, br). |
| 81 | C23H24N4O3 | DCI+ m/z 405 (MH+, 100%) | 400 MHz in CDCl3 10.97(1 H, br); 8.91(1 H, dd, J = 7.2&1.5 Hz); 8.76(1 H, d, J = 8.2 Hz); 8.41(1 H, d, J = 9.5 Hz); 8.35(1 H, dd, J = 8.6&1.5 Hz); 7.90(1 H, m); 7.86(1 H, d, J = 9.5 Hz); 7.72(1 H, t, J = 8.0 Hz); 7.21(1 H, d, J = 8.0 Hz); 5.32(1 H, br); 4.63(1 H, m); 4.17(2 H, m); 4.06(3 H, s); 2.96(1 H, dd, J = 12.4&6.7 Hz); 2.88(1 H, dd, J = 12.4 & 6.0 Hz); 2.39(6 H, s). |
| 82 | C23H25N5O2 | MH+ at 404 | CDCl3: 11.92, (1 H, m)11.12, (1 H, m)8.80, (1 H, d, J = 8.33 Hz)8.40, (1 H, d, J = 9.53 Hz)8.12, (1 H, d, J = 9.62 Hz)7.90, (1 H, d, J = 9.45 Hz)7.70, (1 H, t, J = 8.09 Hz)7.56, (1 H, d, J = 9.59 Hz) 7.20, (1 H, d, J = 7.83 Hz)4.10, (3 H, s)3.83, (2 H, q, J = 6.16 Hz)3.18, (3 H, d, J = 5.11 Hz)2.77, (2 H, t, J = 6.51 Hz)2.40, (6 H, s) |
| 83 | C23H24N4O3 | DCI/NH3 MH+ 405 (100%) | 400 MHz, CDCl3 1.52(3 H, d, J = 6.6 Hz), 2.37(6 H, s), 2.56(1 H, dd, J = 12.4, 6.0 Hz), 2.85(1 H, dd, J = 12.4, 8.1 Hz), 4.10(3 H, s), 4.52–4.62(1 H, m), 7.25(1 H, d, J = 7.8 Hz), 7.57(1 H, d, J = 9.4 Hz), 7.75–7.78 (1 H, m), 7.96(1 H, d, J = 9.5HZ), 8.21(1 H, d, J = 9.4 Hz), 8.49(1 H, d, J = 9.3 Hz), 8.68(1 H, d, J = 9.2 Hz), 11.70(1 H, d, broad), 16.2(1 H, s). |
| 84 | C24H26N4O3 | m/z CI+ 419 (MH+, 100%); 305 (55%) | 400 MHz in CDCl3 11.21(1 H, br); 9.27(1 H, d, J = 8.2 Hz); 9.02(1 H, dd, J = 7.3&1.5 Hz); 8.53(1 H, d, J = 9.6 Hz); 8.42(1 H, dd, J = 8.6&1.5 Hz); 7.99–7.91(2 H, m); 7.75(1 H, t, J = 8.2 Hz); 7.35(1 H, d, J = 8.0 Hz); 4.43(2 H, m); 4.06(3 H, s); 3.48(1 H, s); 3.06(1 H, dd, J = 13.1&5.2 Hz); 2.88(1 H, dd, J = 13.1&4.8 Hz); 2.36(6 H, s); 1.37(3 H, d, J = 6.4 Hz). |
| 85 | C22H22N4O3 | DCI/NH3 MH + 391 (100%) | 400 MHz, CDCl3 2.42(6 H, s), 2.78(2 H, t, J = 6.0 Hz), 3.86–3.90(2 H, m), 4.10(3 H, s), 7.25(1 H, d, J = 7.8 Hz), 7.57(1 H, d, J = 9.4 Hz), 7.70–7.75(1 H, m), 7.95(1 H, d, J = 9.4 Hz), 8.22(1 H, d, J = 9.4 Hz), 8.51(1 H, d, J = 9.6 HzO, 8.81(1 H, d, J = 8.2 Hz), 11.65(1 H, br), 16.17(1 H, s). |
| 86 | C25H26N4O2 | DCI/NH3 m/e 414.4 (MH+, 100%) | 400 MHz, CDCl3 1.35(2 H, m), 1.45(4 H, m), 2.47(4 H, m), 2.7(2 H, t), 3.7(2 H, m), 4.07(3 H, s), 7.5(1 H, d) 7.83(1, m), 7.95(1 H, d), 8.07(1 H, m), 8.43(1 H, m), 8.5(1 H, m), 8.62(1 H, m), 8.73(1 H, m), 10.05(1 H, broad) |
| 87 | C24H26N4O3 | [M + H] + 419 | (400 MHz, CDCl3)11.05(1 H, d), 8.92(1 H, dd, J7.2, 1.5), 8.53(1 H, d, J8.2), 8.48(1 H, d, J9.5), 8.35(1 H, dd, J8.5, 1.5), 7.94–7.86(2 H, m), 7.69(1 H, t, J8.1), 7.19(1 H, d, J7.7), 4.59(1 H, q, J7.1), 4.02(3 H, m), 3.80–3.67(2 H, m), 3.44(1 H, dd, J12.2, 6.0), 2.63(1 H, dd, J12.2, 2.1)2.35(6 H, s), 2.10(1 H, m), 1.99(1 H, m). One exchangeable proton not visible |
| 88 | C22H23N5O2 | MH+ at 390 | CDCl3-11.75, (m, 1 H)8.80, (d, 1 H, J = 8.24 Hz), 8.43, (1 H, d, J = 9.29 Hz)8.01, (d, 1 H, J = 9.32 Hz)7.91, (d, 1 H, J = 9.48 Hz)7.72, (t, 1 H, J = 8.10 Hz)7.23, (d, 1 H, J = 9.34 Hz)7.20, (d, 1 H, J = 7.74 Hz)4.09, (s, 3 H)3.87, (q, 2 H, J = 6.10)2.70, (t, 2 H J = 6.43 Hz)2.42;(s, 6 H). NH2 not visible. |
| 89 | C24H24N4O3 | DCI/NH3 m/e 417.2 (MH+) | 400 MHz, CDCl3 2.62(4 H, t), 2.9(2 H, t), 3.65(4 H, t), 3.93(2 H, m), 4.20(3 H, s), 7.25(1 H, m), 7.7(1 H, t), 8.00(2 H, m), 8.45(1 H, m), 8.60(1 H, d), 8, 75(1 H, d), 9.0(1 H, d), 10.9(1 H, broad) |
| 90 | C24H24N4O2 | DCI/NH3 m/e 401 (MH+) | 400 MHz, CDCl3 1.82(4 H, t), 2.75(4 H, t), 3.2(2 H, t), 3.90–3.99(2 H, m), 4.11(3 H, 3), 7.26–7.31(1 H, m), 7.78(1 H, m), 7.95–7.98(1 H, m), 7.98–8.03(1 H, m)8.4–8.46(1 H, m), 8.55–8.61(1 H, m), 8.78–8.83(1 H, m), 8.98–9.3(1 H, m) NH not visible |
| 91 | C24H26N4O4 | DCI/NH3 m/e 435.3 (MH+) | 400 MHz, CDCl3 2.75(4 H, t), 3.00(2 H, t), 3.56(4 H, t), 3.80–3.89(2 H, m), 4.40(3 H, s), 7.16–7.22(1 H, m), 7.69–7.75(1 H, m), 7.85–7.89(1 H, m), 7.89–7.93(1 H, m), 8.33–8.39(1 H, m), 8.47–8.51(1 H, m), 8.51–8, 55(1 H, m), 8.89–8.95(1 H, m), 11.29(1 H, broad). 2×OH not visible |
| 92 | C24H26N4O2 | DCI/NH3 m/e 403.3 (MH+) | 400 MHz, DMSO 0.99(6 H, t), 2.65(4 H, q), 2.79(2 H, t), 3.65–3.72(2 H, m), 4.07(3 H, s), 7.49–7.53(1 H, m), 7.8–7.87(1 H, m), 7.98(1 H, m), 8.04–8.11(1 H, m), 8.45(1 H, m), 8.51(1 H, m), 8.67(1 H, m), 8.89(1 H, m), 10.15–10.25(1 H, broad). |
| 93 | C23H24N4O2S | ESI + ve m/e 421 (MH+, 100%) | 400 MHz, CDCl3 2.42(6 H, s), 2.70(3 H, s), 2.75(2 H, t, J = 6.0 Hz), 3.85–3.90(2 H, m), 4.10(3 H, s), 7.24(1 H, d, J = 8.0 Hz), 7.72–7.77(1 H, m), 7.91(1 H, d, J = 9.5 Hz), 8.00(1 H, d, J = 2.4 Hz), 8.55(1 H, d, J = 9.7 Hz), 8.85(1 H, d, J = 2.4 Hz), 8.99(1 H, d, J = 8.0 Hz), 10.85(1 H, broad). |

-continued

| Compound Number | Molecular Formula | Mass spec data | $^1$H N.M.R. data |
|---|---|---|---|
| 94 | C23H24N4O3 | ESI + ve m/e 405 (MH+, 100%) | CDCl3, 400 MHz<br>2.42(6 H, s), 2.75(2 H, t, J = 6.0 Hz), 3.85–3.90(2 H, m), 4.07(3 H, s),<br>4.10(3 H, s), 7.22(1 H, d, J = 8.0 Hz), 7.64(1 H, d, J = 3.0 Hz), 7.72–7.77(1 H, m),<br>7.91(1 H, d, J = 9.4 Hz), 8.55(1 H, d, J = 9.6 Hz), 8.70(1 H, d, J = 3.0 Hz),<br>8.99(1 H, d, J = 8.0 Hz), 10.92(1 H, broad). |
| 95 | C24H26N4O4 | DCI/NH3 m/e 435 (MH+, 100%) | 400 MHz, CDCl3<br>2.32(6 H, s), 2.65(1 H, dd, J = 12.3, 6.7 Hz), 2.75(1 H, dd, J = 12.3, 8.1 Hz), 3.98(1 H, dd,<br>J = 11.3, 4.1 Hz), 4.05(3 H, s), 4.09(3 H, s), 1 H under 2 methoxy peaks, 4.41–4.48(1 H, m),<br>6.91(1 H, d, J = 5.3 Hz), 7.20(1 H, d, J = 7.9 Hz), 7.67–7.71(2 H, m), 7.86(1 H, d, J = 9.6 Hz),<br>8.29(1 H, d, J = 9.4 Hz), 8.45(1 H, d, J = 9.7 Hz), 8.91(1 H, d, J = 8.2 Hz).<br>one exchangable proton not visible |
| 96 | C21H20N4O2 | DCI/NH3 m/e 361.0 (MH+) | 400 MHz, CDCl3<br>2.64(3 H, s), 3.12(2 H, t), 3.90–3.96(2 H, m), 4.11(3 H, s), 7.29(1 H, s), 7.63–7.71(1 H, m),<br>7.92–7.95(1 H, m), 7.95–8.01(1 H, m), 8.38–8.45(1 H, m), 8.55–8.61(1 H, m), 8.89–8.95(1 H, m),<br>8.95–9.02(1 H, m), 11.08(1 H, broad) |
| 97 | C23H24N4O4 | DCI/NH3 m/z 421 (MH+, 100%) | 400 MHz, CDCl3<br>2.40(6 H, s), 2.92(1 H, dd, J = 12.4, 7.6 Hz), 2.99(1 H, dd, J = 12.4, 5.9 Hz), 4.07(3 H, s),<br>4.18–4.20(2 H, m), 4.58–4.68(1 H, m), 7.21(1 H, d, J = 7.9 Hz), 7.53(1 H, d, J = 9.5 Hz),<br>7.70–7.73(1 H, m), 7.86(1 H, d, J = 9.4Mz), 8.15(1 H, d, J = 9.4 Hz), 8.37(1 H, d, J = 9.3 Hz), 8.65<br>(1 H, d, J = 8.3 Hz), 11.70(1 H, d), 15.82(1 H, s) One exchangable proton not visible |
| 98 | C25H28N4O2 | [M + H] + 417 | (400 MHz, CDCl3)11.0(1 H, br, d), 9.03(1 H, dd, J7.3, 1.6), 8.80(1 H, d, J8.3),<br>8.56(1 H, d, J9.5), 8.41(1 H, dd, J8.5, 1.5), 7.97(2 H, m), 7.75(1 H, t, J8.1),<br>7.26(1 H, d, J7.7), 4.56(1 H, m), 4.09(3 H, s), 2.89(1 H, dd, J12.6, 9.0), 2.64(1 H,<br>dd, J12.6, 5.1), 2.34(6 H, s), 2.22(1 H, m), 1.12(3 H, d, J2.5), 1.10(3 H, d, J 2.4) |
| 99 | C23H22N4O2 | DCI/NH3 m/z 387 (MH+, 100%) | CDCl3/400 MHz,<br>2.02–2.10(1 H, m), 2.40–2.46(1 H, m), 2.52–2.61(1 H, m), 2.58(3 H, s), 2.75–2.79(1 H, m),<br>2.99–3.02(1 H, m), 3.13–3.18(1 H, m), 4.10(3 H, s), 4.90–4.98(1 H, m), 7.26(1 H, d),<br>7.75–7.80(1 H, m), 7.95–8.00(2 H, m), 8.42(1 H, dd, J = 8.4, 1.5 Hz), 8.58(1 H, d, J = 9.6 Hz),<br>8.99–9.03(2 H, m), 11.32(1 H, d). |
| 100 | C25H29N5O2 | MH+ 432 | (400 MHz, CDCl3): 2.25(6 H, s), 2.32–2.38(1 H, m), 2.52(6 H, s), 2.56–2.62(1 H, m),<br>3.00–3.09(1 H, m), 3.65–3.74(1 H, m), 4.01–4.09(1 H, m), 4.11(3 H, s), 7.28(1 H, d, J = 7.7),<br>7.78(1 H, t, J = 8.0), 7.96–8.01(2 H, m), 8.42(1 H, d, J = 8.5), 8.58(1 H, d, J = 9.6),<br>8.98–9.03(2 H, m) |

The invention claimed is:

1. A compound which is a benzo[a]phenazine-11-carboxamide derivative of formula (I)

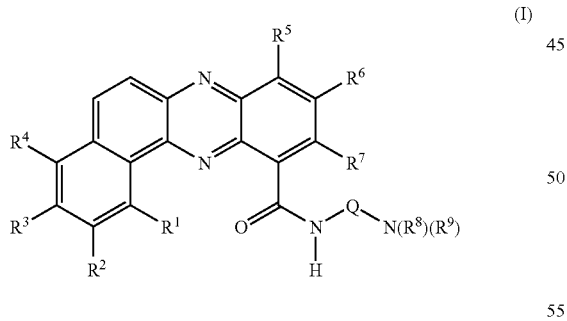

wherein each of $R^1$ to $R^3$, is from hydrogen, and $R^4$ is selected from halogen, hydroxyl, $C_1$–$C_6$ alkoxy which is unsubstituted or substituted, heteroaryloxy, nitro, cyano, azido, amidoxime, $CO_2R^{10}$, $CON(R^{12})_2$, $OCON(R^{12})_2$, $SR^{10}$, $SOR^{11}$, $SO_2R^{11}$, $SO_2N(R^{12})_2$, $N(R^{12})_2$, $NR^{10}SO_2R^{11}$, $N(SO_2R_{11})_2 NR^{10}(CH_2)_n CN$, $NR^{10}COR^{11}$, $OCOR^{11}$ or $COR^{10}$;

each of $R^5$ to $R^7$, which are the same or different, is selected from hydrogen, halogen, hydroxy, $C_1$–$C_6$ alkoxy, $C_1$–$C_6$ alkyl, $SR^{10}$ and $N(R^{12})_2$;

Q is $C_1$–$C_6$ alkylene which is unsubstituted or substituted by (i) $C_1$–$C_6$ alkyl which is unsubstituted or substituted, (ii) hydroxy, provided that the hydroxy group is not α to either of the N atoms adjacent to Q in formula (I), (iii) $CO_2R^{10}$, or (iv) $CON(R^{12})_2$;

$R^8$ and $R^9$, which are the same or different, are each hydrogen or $C_1$–$C_6$ alkyl, or $R^8$ and $R^9$ together with the nitrogen atom to which they are attached form a saturated 5- or 6-membered N-containing heterocyclic ring which may include one additional heteroatom selected from O, N and S, or one of $R^8$ and $R^9$ is an alkylene chain optionally interrupted by O, N or S, which is attached to a carbon atom on the alkylene chain represented by Q to complete a saturated 5- or 6-membered N-containing heterocyclic ring as defined above;

$R^{10}$ is hydrogen, $C_1$–$C_6$ alkyl, $C_3$–$C_6$ cycloalkyl, benzyl or phenyl;

$R^{11}$ is $C_1$–$C_6$ alkyl, $C_3$–$C_6$ cycloalkyl, benzyl or phenyl;

each $R^{12}$, which are the same or different, is hydrogen, $C_1$–$C_6$ alkyl cycloalkyl, benzyl or phenyl, or the two $R^{12}$ groups form, together with the nitrogen atom to which they are attached a 5- or 6-membered saturated N-containing heterocyclic ring which may include 1 or 2 additional heteroatoms selected from O, N and S; and n is 1, 2 or 3;

or a pharmaceutically acceptable salt thereof.

2. A compound according to claim 1 wherein the benzo[a]phenazine-11-carboxamide derivative is of formula (Ia):

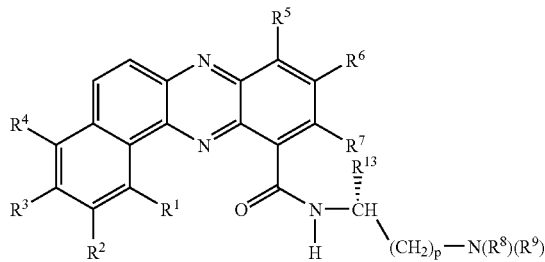

wherein $R^1$ to $R^9$ are as defined in claim 1;
p is 1, 2 or 3; and
$R^{13}$ is (i) hydrogen, (ii) $C_1$–$C_6$ alkyl which is unsubstituted or substituted by hydroxy, aryl or $N(R^{12})_2$ in which $R^{12}$ is as defined in claim 1, (iii) $CO_2R^{10}$, (iv) $CON(R^{12})_2$ or (v) aryl.

3. A compound according to claim 1 wherein $R^4$ is $C_1$–$C_6$ alkoxy, hydroxy, hydroxy-$C_1$–$C_6$ alkyl, nitrile or halogen.

4. A compound according to claim 1 wherein $R^7$ is hydroxyl.

5. A compound as defined in claim 1 which is selected from:
- 4-Methoxy-benzo[a]phenazine-11-carboxylic acid (2-dimethylamino-ethyl)-amide;
- 4-Hydroxy-benzo[a]phenazine-11-carboxylic acid (2-dimethylamino-ethyl)-amide hydrobromide salt;
- 4-Nitro-benzo[a]phenazine-11-carboxylic acid (2-dimethylamino-ethyl)-amide;
- 4-Dimethylaminomethyl-3-hydroxy-benzo[a]phenazine-11-carboxylic acid (2-dimethylamino-ethyl)-amide,
- 9-Bromo-4-methoxy-benzo[a]phenazine-11-carboxylic acid (2-dimethylamino-ethyl)-amide;
- 4-Cyanomethoxy-benzo[a]phenazine-11-carboxylic acid (2-dimethylamino-ethyl)-amide;
- 4-Benzyloxy-benzo[a]phenazine-11-carboxylic acid (2-dimethylamino-ethyl)-amide;
- 4-Prop-2-ynyloxy-benzo[a]phenazine-11-carboxylic acid (2-dimethylamino-ethyl)-amide;
- 4-Ethoxy-benzo[a]phenazine-11-carboxylic acid (2-dimethylamino-ethyl)-amide;
- 4-Isobutoxy-benzo[a]phenazine-11-carboxylic acid (2-dimethylamino-ethyl)-amide;
- 4-(4-Chloro-benzyloxy)-benzo[a]phenazine-11-carboxylic acid (2-dimethylamino-ethyl)-amide;
- 4-(2-Methoxy-ethoxy)-benzo[a]phenazine-11-carboxylic acid (2-dimethylamino-ethyl)-amide;
- [11-(2-Dimethylamino-ethylcarbamoyl)-benzo[a]phenazin-4-yloxy]-acetic acid ethyl ester;
- 4-(2-Hydroxy-ethoxy)-benzo[a]phenazine-11-carboxylic acid (2-dimethylamino-ethyl)-amide;
- 4-(Pyrimidin-2-yloxy)-benzo[a]phenazine-11-carboxylic acid (2-dimethylamino-ethyl)-amide;
- 4-(2-Morpholin-4-yl-ethoxy)-benzo[a]phenazine-11-carboxylic acid (2-dimethylamino-ethyl)-amide;
- 4-(3-Cyano-propoxy)-benzo[a]phenazine-11-carboxylic acid (2-dimethylamino-ethyl)-amide;
- 4-Fluoro-benzo[a]phenazine-11-carboxylic acid(2-dimethylamino-ethyl)-amide;
- 4-(3-Dimethylamino-propoxy)-benzo[a]phenazine-11-carboxylic acid (2-dimethylamino-ethyl)-amide;
- 4-Methylsulfanyl-benzo[a]phenazine-11-carboxylic acid (2-dimethylamino-ethyl)-amide;
- 4-Carbamoylmethoxy-benzo[a]phenazine-11-carboxylic acid (2-dimethylamino-ethyl)-amide;
- 4-Methoxy-benzo[a]phenazine-11-carboxylic acid (3-amino-2-hydroxy-propyl)-amide;
- 4-Methoxy-benzo[a]phenazine-11-carboxylic acid (3-dimethylamino-propyl)-amide;
- 4-Bromo-benzo[a]phenazine-11-carboxylic acid (2-dimethylamino-ethyl)-amide;
- Acetic acid 11-(2-dimethylamino-ethylcarbamoyl)-benzo[a]phenazin-4-yl ester;
- 4-(2-Oxo-propoxy)-benzo[a]phenazine-11-carboxylic acid (2-dimethylamino-ethyl)-amide;
- 4-Methoxy-benzo[a]phenazine-11-carboxylic acid (2-dimethylamino-1-methyl-ethyl)-amide;
- 4-Cyano-benzo[a]phenazine-11-carboxylic acid (2-dimethylamino-ethyl)-amide;
- Ethyl-carbamic acid 11-(2-dimethylamino-ethylcarbamoyl)-benzo[a]phenazin-4-yl ester;
- 4-Methanesulfonyl-benzo[a]phenazine-11-carboxylic acid (2-dimethylamino-ethyl)-amide;
- 4-Chloro-benzo[a]phenazine-11-carboxylic acid (2-dimethylamino-ethyl)-amide;
- 4-Azido-benzo[a]phenazine-11-carboxylic acid (2-dimethylamino-ethyl)-amide;
- 4-Amino-benzo[a]phenazine-11-carboxylic acid (2-dimethylamino-ethyl)-amide;
- [11-(2-Dimethylamino-ethylcarbamoyl)-benzo[a]phenazin-4-yloxy]-acetic acid trifluoro-acetate salt;
- 4-Acetylamino-benzo[a]phenazine-11-carboxylic acid (2-dimethylamino-ethyl)-amide;
- 11-(2-Dimethylamino-ethylcarbamoyl)-benzo[a]phenazine-4-carboxylic acid methyl ester;
- 4-Bis-(Methanesulfonylamino)-benzo[a]phenazine-11-carboxylic acid (2-dimethylamino-ethyl)-amide;
- 4-(N-Hydroxycarbamimidoyl)-benzo[a]phenazine-11-carboxylic acid (2-dimethylamino-ethyl)-amide;
- 4-Hydroxymethyl-benzo[a]phenazine-11-carboxylic acid (2-dimethylamino-ethyl)-amide;
- 4-Methylsulfamoyl-benzo[a]phenazine-11-carboxylic acid (2-dimethylamino-ethyl)-amide trifluoro-acetate salt;
- 4-Dimethylamino-benzo[a]phenazine-11-carboxylic acid (2-dimethylamino-ethyl)-amide;
- 4-Methanesulfonylamino-benzo[a]phenazine-11-carboxylic acid (2-dimethylamino-ethyl)-amide;
- 4-Dimethylsulfamoyl-benzo[a]phenazine-11-carboxylic acid (2-dimethylamino-ethyl)-amide;
- 4-(Cyanomethyl-amino)-benzo[a]phenazine-11-carboxylic acid (2-dimethylamino-ethyl)-amide;
- 4,10-Dimethoxy-benzo[a]phenazine-11-carboxylic acid (2-dimethylamino-ethyl)-amide;
- 4-Methoxy-benzo[a]phenazine-11-carboxylic acid (2-dimethylamino-propyl)-amide;
- Benzo[a]phenazine-4,11-dicarboxylic acid 4-amide 11-[(2-dimethylamine-ethyl)-amide]trifluoroacetic acid salt;
- 4-Methoxy-benzo[a]phenazine-11-carboxylic acid (2-dimethylamino-1,1-dimethyl-ethyl)-amide;
- 4-Methoxy-8-methyl-benzo[a]phenazine-11-carboxylic acid (2-dimethylamino-ethyl)-amide;
- 4,10-Dihydroxy-benzo[a]phenazine-11-carboxylic acid (2-dimethylamino-ethyl)-amide;

4-Methoxy-benzo[a]phenazine-11-carboxylic acid (1-dimethylaminomethyl-propyl)-amide;
4,10-Dimethoxy-benzo[a]phenazine-11-carboxylic acid (2-dimethylamino-1-methyl-ethyl)-amide;
9-Chloro-4-methoxy-benzo[a]phenazine-11-carboxylic acid (2-dimethylamino-ethyl)-amide;
4-Methoxy-benzo[a]phenazine-11-carboxylic acid (1-dimethylaminomethyl-2-methyl-propyl)-amide;
4-Methoxy-benzo[a]phenazine-11-carboxylic acid (2-dimethylamino-1-hydroxymethyl-ethyl)-amide;
4-Methoxy-benzo[a]phenazine-11-carboxylic acid (1-dimethylaminomethyl-2-phenyl-ethyl)-amide;
4-Methoxy-benzo[a]phenazine-11-carboxylic acid (2-dimethylamino-1-(S)-methyl-ethyl)-amide;
4-Methoxy-benzo[a]phenazine-11-carboxylic acid (2-dimethylamino-1-(R)-methyl-ethyl)-amide;
4-Nitro-benzo[a]phenazine-11-carboxylic acid (2-dimethylamino-1-methyl-ethyl)-amide;
4-Methoxy-benzo[a]phenazine-11-carboxylic acid (2-dimethylamino-1-(S)-hydroxymethyl-ethyl)-amide;
4-Methoxy-10-methylamino-benzo[a]phenazine-11-carboxylic acid (2-dimethylamino-ethyl)-amide;
10-Hydroxy-4-methoxy-benzo[a]phenazine-11-carboxylic acid (2-dimethylamino-1(R)-methyl-ethyl)-amide;
4-Methoxy-benzo[a]phenazine-11-carboxylic acid (1-dimethylaminomethyl-2-hydroxy-propyl)-amide;
10-Hydroxy-4-methoxy-benzo[a]phenazine-11-carboxylic acid (2-dimethylamino-ethyl)-amide;
4-Methoxy-benzo[a]phenazine-11-carboxylic acid (2-piperidin-1-yl-ethyl)-amide;
4-Methoxy-benzo[a]phenazine-11-carboxylic acid[1-dimethylamino-1-(2-hydroxyethyl)]-ethylamide
10-Amino-4-methoxy-benzo[a]phenazine-11-carboxylic acid (2-dimethylamino-ethyl)-amide;
4-Methoxy-benzo[a]phenazine-11-carboxylic acid (2-morpholin-4-yl-ethyl)-amide;
4-Methoxy-benzo[a]phenazine-11-carboxylic acid (2-pyrrolidin-1-yl-ethyl)-amide;
4-Methoxy-benzo[a]phenazine-11-carboxylic acid{2-[bis-(2-hydroxy-ethyl)-amino]-ethyl}-amide;
4-Methoxy-benzo[a]phenazine-11-carboxylic acid (2-diethylamino-ethyl)-amide;
4-Methoxy-9-methylsulfanyl-benzo[a]phenazine-11-carboxylic acid (2-dimethylamino-ethyl)-amide;
4,9-Dimethoxy-benzo[a]phenazine-11-carboxylic acid (2-dimethylamino-ethyl)-amide;
4,10-Dimethoxy-benzo[a]phenazine-11-carboxylic acid (2-dimethylamino-1(S)-hydroxymethyl-ethyl)-amide;
4-Methoxy-benzo[a]phenazine-11-carboxylic acid (2-methylamino-ethyl)-amide;
10-Hydroxy-4-methoxy-benzo[a]phenazine-11-carboxylic acid (2-dimethylamino-1(S)-hydroxymethyl-ethyl)-amide;
(R)-4-Methoxy-benzo[a]phenazine-11-carboxylic acid (1-dimethylaminomethyl-2-methyl-propyl)-amide;
4-Methoxy-benzo[a]phenazine-11-carboxylic acid (1-methyl-pyrrolidin-3-(R)-yl)-amide;
4-Methoxy-benzo[a]phenazine-11-carboxylic acid (2,3-(bis)-dimethylamino-propyl) amide;

and the pharmaceutically acceptable salts thereof.

6. A pharmaceutical composition which comprises a pharmaceutically acceptable carrier or diluent and, as an active ingredient, a compound as defined in claim 1.

7. A process for producing a compound as defined in claim 1, which process comprises:
(a) treating an activated derivative of a compound of formula (II):

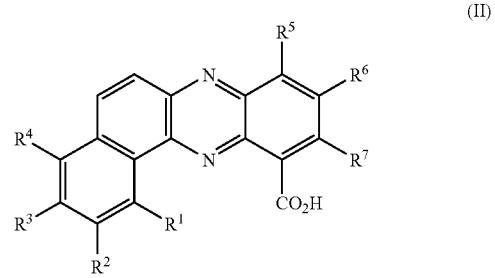

wherein $R^1$ to $R^7$ are as defined, with an amine of formula (III):

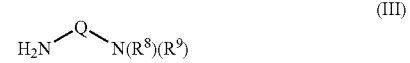

wherein Q, $R^8$ and $R^9$ are as defined in claim 1; or
(a) treating a compound of formula (IV):

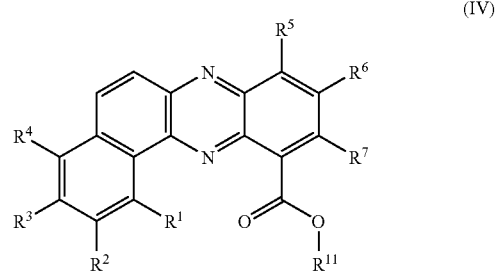

wherein $R^1$ to $R^7$ and $R^{11}$ are as defined, with a compound of formula (III) as defined above, either in an organic solvent or neat, and at an elevated temperature; and
(c) if desired, converting the resulting benzo(a)phenazine-11-carboxamide derivative into a pharmaceutically acceptable salt thereof.

8. A compound of formula (II):

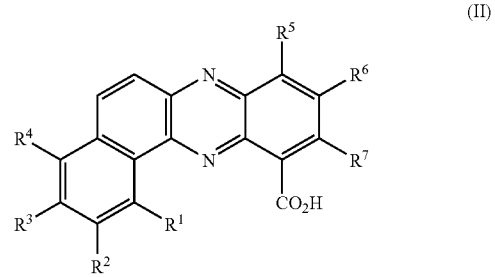

wherein each of $R^1$ to $R^3$ is hydrogen and $R^4$ is selected from halogen, hydroxyl, $C_{1-C6}$ alkoxy which is unsubstituted or substituted, heteroaryloxy, nitro, cyano, azido, amidoxime, $CO_2R^{10}$, $CON(R^{12})_2$, $OCON(R^{12})$, $SR^{10}$, $SOR^{11}$, $SO_2R^{11}$, $SO_2N(R^{12})_2$, $N(R^{12})_2$, $NR^{10}SO_2R^{11}$, $N(SO_2R_{11})_2$ $NR^{10}(CH_2)_nCN$, $NR^{10}COR^{11}$, $OCOR^{11}$ or $COR^{10}$;

each of $R^5$ to $R^7$, which are the same or different, is selected from hydrogen, halogen, hydroxy, $C_1-C_6$ alkoxy, $C_1-C_6$ alkyl, $SR^{10}$ and $N(R^{12})_2$;

$R^{10}$ is hydrogen, $C_1-C_6$ alkyl, $C_3-C_6$ cycloalkyl, benzyl or phenyl;

$R^{11}$ is $C_1C_6$ alkyl, $C_3-C_6$ cycloalkyl, benzyl or phenyl;

each $R^{12}$, which are the same or different, is hydrogen, $C_1-C_6$ alkyl, cycloalkyl, benzyl or phenyl, or the two $R^{12}$ groups form, together with the nitrogen atom to which they are attached a 5- or 6-membered saturated N-containing heterocyclic ring which may include 1 or 2 additional heteroatoms selected from O, N and S; and n is 1, 2 or 3, or a salt or ester thereof.

9. A process for producing a compound of formula (II) as defined in claim 8, which process comprises:

(a) treating a 1,2-naphthoquinone of formula (V):

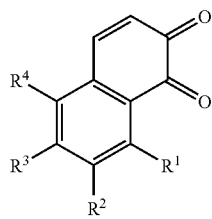

(V)

wherein $R^1$ to $R^4$ are as defined, with a benzoic acid of formula (VI):

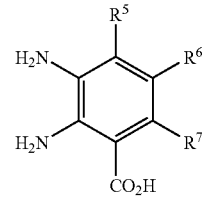

(VI)

or an ester or salt thereof, wherein $R^5$, $R^6$ and $R^7$ are as defined in an organic solvent.

10. A process according to claim 9 which is conducted in the presence of from 1 to 5 equivalents of a mineral acid.

11. A method of treating a patient in need of an antibacterial or antifungal agent, which method comprises administering thereto a therapeutically effective amount of a compound as defined in claim 1.

\* \* \* \* \*

UNITED STATES PATENT AND TRADEMARK OFFICE
CERTIFICATE OF CORRECTION

PATENT NO. : 7,132,419 B2  
APPLICATION NO. : 11/024759  
DATED : November 7, 2006  
INVENTOR(S) : Milton et al.

It is certified that error appears in the above-identified patent and that said Letters Patent is hereby corrected as shown below:

On Title page item (63) Continuation of application Serial No. 10/148,601 filed September 18, 2002, which application is a 371 of PCT/GB00/04609 filed December 1, 2000 item 30 omitted please add Dec. 2, 1999–GB 9928542.1

Signed and Sealed this

Twenty-seventh Day of March, 2007

JON W. DUDAS  
*Director of the United States Patent and Trademark Office*